United States Patent [19]

Vakharia et al.

[11] Patent Number: 5,595,912

[45] Date of Patent: Jan. 21, 1997

[54] SPECIFIC DNA AND RNA SEQUENCES ASSOCIATED WITH US IBDV VARIANTS, VECTOR CARRYING DNA SEQUENCES, HOST CARRYING CLONED VECTOR, DEDUCED AMINO ACID SEQUENCES, VACCINE AND METHOD OF VACCINATION

[75] Inventors: Vikram Vakharia, Bowie; David Snyder, deceased, late of Bowie, both of Md., by Nancy Snyder, legal representative.

[73] Assignee: University of Maryland College Park, College Park, Md.

[21] Appl. No.: 216,276

[22] Filed: Mar. 23, 1994

Related U.S. Application Data

[63] Continuation-in-part of Ser. No. 83,784, Jun. 28, 1993, abandoned, which is a continuation of Ser. No. 519,202, May 4, 1990, abandoned.

[51] Int. Cl.[6] ............................ C12N 15/85; C12N 15/40
[52] U.S. Cl. .................................. 435/320.1; 536/23.72
[58] Field of Search ...................... 536/23.72; 435/320.1

[56] References Cited

U.S. PATENT DOCUMENTS 5,064,646  11/1991  Snyder ........................................ 424/89

OTHER PUBLICATIONS

Hudson et al. (1986), Nucl. Acids Res. 14(12):5001–5012.
Snyder et al. (1988), Proc. 23rd Nat. Meeting Poultry Health Condemnation, Ocean City, MD. pp. 119–129.
Boyle et al. (1988), Virus Res. 10:343–356.

*Primary Examiner*—Mindy Fleisher
*Assistant Examiner*—Philip W. Carter
*Attorney, Agent, or Firm*—Oblon, Spivak, McClelland, Maier & Neustadt, P.C.

[57] ABSTRACT

The isolated DNA sequence for the VP2 antigenic region of IBDV, GLS strain, is expressed by incorporation in a virus carrier. Four variant DNA sequences encoding the VP2 region are provided, each of which may be used in the preparation of a vaccine to prevent IBDV in poultry.

16 Claims, No Drawings

SPECIFIC DNA AND RNA SEQUENCES ASSOCIATED WITH US IBDV VARIANTS, VECTOR CARRYING DNA SEQUENCES, HOST CARRYING CLONED VECTOR, DEDUCED AMINO ACID SEQUENCES, VACCINE AND METHOD OF VACCINATION

This application is a CIP application of U.S. patent application Ser. No. 08/083,784 filed Jun. 28, 1993, abandoned, which in turn is a continuation application of U.S. patent application Ser. No. 07/519,202 filed May 4, 1990, also abandoned.

TECHNICAL FIELD

This invention relates to the infectious bursal disease virus (IBDV) that is associated with Gumboro disease of young chickens. More particularly, this invention relates to biologically pure DNA, RNA and polypeptide sequences associated with the VP2 protein of the virus, a broad spectrum IBDV vaccine and other related technologies. The present technology may be applied to a vaccine for the in vivo production of conformational epitopes which elicit an immunological response to the virus. In this manner, the administration of the vaccine affords protection against IBDV not only to a subject, e.g., poultry, that is being inoculated, but also to its progeny.

DESCRIPTION OF THE BACKGROUND

Infectious bursal disease (IBD) or Gumboro disease is a highly contagious viral disease of young chickens which is characterized by the destruction of lymphoid follicles in the bursa of Fabricius. In a fully susceptible chicken flock of 3–6 weeks of age the clinical disease causes severe immunosuppression, and is responsible for losses due to impaired growth, decreased feed efficiency, and death. Susceptible chickens less than 3 weeks old do not exhibit outward clinical signs of the disease but have a marked infection characterized by gross lesions of the bursa.

The virus associated with the symptoms of the disease was called infectious bursal disease virus (IBDV). IBDV is a pathogen of major economic importance to the nation and world's poultry industries. It causes severe immunodeficiency in young chickens by destruction of precursors of antibody-producing B cells in the bursa of Fabricius. Immunosuppression causes increased susceptibility to other diseases, and interferes with the effective vaccination against Newcastle-disease, Marek's disease and infectious bronchitis disease viruses.

There are two known serotypes of IBDV. Serotype I viruses are pathogenic to chickens whereas serotype II viruses infect chickens and turkeys. The infection of turkeys is presently of unknown clinical significance.

Up until recently, the principal methods of controlling IBD in young chickens were by vaccination with an avirulent strain of IBDV or by transferring high levels of maternal antibody induced by the administration of live and killed IBD vaccines to breeder hens (Wyeth, P. J. and Cullen, G. A., Vet. Rec. 10–4, 188–193, (1979)).

In recent years field outbreaks of IBD, particularly in the eastern United States, have shown infection of poultry with variant viruses which are not completely neutralized by antibodies against standard serotype I IBDV (Rosenberger, J. K. et al, Proc. of the 20th National Meeting on Poultry Health and Condemnations, (1985); Snyder, D. B. et al, Proc. 23rd National Meeting on Poultry Health and Condemnations, Ocean City, Md. (1988)).

IBDV belongs to a group of viruses called Birnaviridae which includes other bisegmented RNA viruses such as infectious pancreatic necrosis virus (fish), tellina virus and oyster virus (bivalve molluscs) and drosophila X virus (fruit fly). These viruses all contain high molecular weight (MW) double stranded RNA genomes.

The capsid of the IBDV virion consists of at least four structural proteins. As many as nine structural proteins have been reported but there is evidence that some of these may have a precursor-product relationship. The designation and molecular weights of the four viral proteins (VP) are as shown in Table 1 below.

TABLE 1

| Viral Proteins of IBDV | |
|---|---|
| Viral Protein | Molecular Weight |
| VP1 | 90 kDa |
| VP2 | 41 kDa |
| VP3 | 32 kDa |
| VP4 | 28 kDa |

An additional protein, VPX, of 47 kDa was determined to be a precursor of the VP2 protein.

The nucleotide sequences of IBDV serotype I (ST-C, standard challenge virus and attenuated virus BB) and serotype II obtained from turkeys (OH, Ohio strain) have been compared and have provided preliminary information thereof (Jackwood, D. J. et al, 69th Annual Meeting of the Conference of Research Workers in Animal Disease, Abs. no. 346, Chicago, Ill. (1988)).

Two segments of double stranded RNA were identified in the genome of IBDV. One contains 3400 base pairs and has a molecular weight of $2.06 \times 10^6$, and the other contains 2900 base pairs and has a molecular weight of $1.76 \times 10^6$. In vitro translation of the denatured genomic RNA of the virus has shown that the larger RNA segment encodes three structural proteins, i.e., VP2, VP3 and VP4, and the smaller RNA segment encodes only one protein, i.e., VP1.

Both genomic segments of an Australian strain of IBDV, that is different from the U.S. strains, were recently cloned and sequenced (Hudson, P. J. et al, Nucleic Acids Res. 14, 5001–5012, (1986); Morgan, M. M. et al, Virology 163, 240–243, (1988)). The complete nucleotide sequence of the larger segment has shown that these proteins are encoded in the order VP2, VP4 and VP3, and that they are contained in one open reading frame. In addition, further nucleotide sequence data confirmed that the smaller RNA segment encodes only the VP1 protein (Morgan, M. M. et al, Virology 163, 240–243, (1988)). This protein is a minor component of the virion and it is presumed to be the viral RNA polymerase. In IBDV, the VP1 protein binds tightly to both ends of the two genomic segments, and it effectively circularizes the molecule.

It has been recently demonstrated that the VP2 protein is the major host protective immunogen of IBDV, and that it contains the antigenic region responsible for the induction of neutralizing antibodies. The region containing the neutralization site has been shown to be highly conformation-dependent. The VP3 protein has been considered to be a group-specific antigen because it is recognized by monoclonal antibodies directed against it from strains of both serotype I and II viruses. The VP4 protein appears to be a virus-coded protease that is involved in the processing of a precursor polyprotein of the VP2, VP3 and VP4 proteins. However, the precise manner in which the proteolytic break up takes place is not yet clear.

The occurrence of antigenic variations among IBDV isolates has been repeatedly reported. The use of monoclonal antibodies (MCA) B29, R63, B69, 179, BK9 and 57 raised against different strains of IBDV led to the recognition of the occurrence of three distinct antigenic types of IBDV in the field in the U.S. These data are shown in Table 2 below.

The new GLS variant was recently discovered on the basis of antigen-capture ELISA tests (Snyder, D. B. et al, Proc. 23rd Nat. Meeting Poultry Health and Condem., Ocean City, Md. (1988)). This strain of IBDV is presently replacing the Delaware variant and has already become the most predominant IBDV type occurring in the Delmarva Peninsula. Data on IBDV types obtained with the monoclonal antibodies (MCAs) R63, B29, above are shown in Table 3 below.

TABLE 2

AC-ELISA characterization of banked field isolates, laboratory/reference and vaccine strains of IBDV.

| IBDV Source | Capture MCA | | | | | | No. Tested | Virus Type |
|---|---|---|---|---|---|---|---|---|
| | B29 | R63[a] | B69[a] | 179[a] | BK9 | 57[a] | | |
| Banked Isolates: | | | | | | | | |
| Pure Classic | + | + | + | + | − | − | 60 | Classic |
| Pure DEL | + | + | − | + | + | − | 76 | Delaware |
| Pure GLS | + | − | − | + | − | + | 70 | Pure GLS |
| Laboratory virus: | | | | | | | | |
| IM | + | + | + | + | − | − | 1 | Classic |
| STC | + | + | + | + | − | − | 1 | Classic |
| Edgar | + | + | + | + | − | − | 1 | Classic |
| 2512 | + | + | + | + | − | − | 1 | Classic |
| LUK | + | + | + | + | − | − | 1 | Classic |
| F52/70 | + | + | + | + | − | − | 1 | Classic |
| MD | + | + | + | + | − | − | 1 | Classic |
| A/DEL | + | + | − | + | + | − | 1 | Delaware |
| D/DEL | + | + | − | + | + | − | 1 | Delaware |
| E/DEL | + | + | − | + | + | − | 1 | Delaware |
| G/DEL | + | + | − | + | + | − | 1 | Delaware |
| Vaccines: | | | | | | | | |
| D78 | + | + | + | + | − | − | 1 | Classic |
| Univax | + | + | + | + | − | − | 1 | Classic |
| Bursine | + | + | + | + | − | − | 1 | Classic |
| Bio-Burs | + | + | + | + | − | − | 1 | Classic |
| Bio-Burs I | + | + | + | + | − | − | 1 | Classic |
| IBD Blend | + | + | + | + | − | − | 1 | Classic |
| Bursa-vac | + | + | + | + | − | − | 1 | Classic |
| VI-Bur-G | + | + | + | + | − | − | 1 | Classic |
| S706 | + | + | + | + | − | − | 1 | Classic |

[a]MCA neutralizes.

Two of the MCAs discussed above, B69 and 57, made specifically against the Classic D78 and GLS strains of IBDV have been found by virus neutralization tests to neutralize only the parent virus. The third MCA, R63, also made against the IBDV Classic strain was shown to neutralize all serotype I IBDVs except the GLS variant virus. Two other MCAs, 179 and BK44, have been shown to be potent neutralizers of all serotype I IBDVs studied so far.

All serotype I IBDVs bind to MCA B29 in an antigen-capture enzyme-linked immunosorbens assay (AC-ELISA). However, the B29 MCA is not a neutralizing MCA. On the other hand, the B69 and R63 MCAs are both neutralizing MCAs. Predictions on new variants can be made on the basis of their reactivities with the B69 MCA. A virus that does not bind to this MCA in an AC-ELISA is very likely antigenically different from the standard type ("classic"), and would be termed as a variant virus. Neither the Delaware type E (E/DEL) nor the GLS variants of IBDV react with the B69 MCA. In addition, the E/DEL variant can be distinguished from the GLS variant virus on the basis of its reactivity with the R63 MCA. The GLS variant virus does not bind to the R63 MCA in AC-ELISA assay as is shown in Table 2 above.

TABLE 3

Geographic Distribution of IBDV Types as Determined With an MCA R63, B69 and B29 Based AC-ELISA.

| | % IBDV Type | | | Total # of Isolates |
|---|---|---|---|---|
| State | Classic | Delaware | GLS | |
| Delmarva | 8 | 42 | 50 | 319 |
| AL | 15 | 67 | 18 | 52 |
| NC | 19 | 52 | 29 | 67 |
| MS | 20 | 70 | 10 | 10 |
| GA | 22 | 52 | 26 | 27 |
| AR | 36 | 45 | 19 | 53 |
| TN | 50 | 50 | 0 | 2 |
| MO | 50 | 50 | 0 | 2 |
| IN | 57 | 43 | 0 | 7 |
| FL | 73 | 20 | 7 | 15 |
| CA | 84 | 8 | 8 | 25 |
| OK | 87 | 0 | 13 | 8 |

TABLE 3-continued

Geographic Distribution of IBDV Types as Determined With an MCA R63, B69 and B29 Based AC-ELISA.

| | % IBDV Type | | | |
|---|---|---|---|---|
| State | Classic | Delaware | GLS | Total # of Isolates |
| TX | 100 | 0 | 0 | 10 |
| OR | 100 | 0 | 0 | 7 |
| MN | 100 | 0 | 0 | 7 |
| WA | 100 | 0 | 0 | 3 |
| VA | 0 | 100 | 0 | 8 |
| PA | 0 | 100 | 0 | 5 |
| | | | Total #: | 627 |

There are currently 9 "live" attenuated avirulent vaccines available in the market. All the vaccine strains react with the B29, B69 and R63 in MCAs AC-ELISA tests. These viruses, therefore, are classified as the "Classic" type, as shown in Table 2 above. The brand name of these vaccines and their sources are given in Table 4 below.

TABLE 4

Vaccines for IBDV

| Vaccine | Company |
|---|---|
| Clone-vac D78 | Intervet America |
| Univax | American Sci. Lab. |
| Bursine | Salisbury |
| Bio-Burs | KeeVet |
| Bio-Burs I | KeeVet |
| IBD Blend | Ceva |
| Bursa-vac | Sterwin |
| VI-Bur-G | Vineland |
| S706 | Select |

The above vaccine strains are not virulent like the variant viruses and they may be given "live". Thus, they do not have to be inactivated or "killed" in order to be used as vaccines. However, these vaccines are not fully effective in protecting against infection with variant viruses. A limited number of chickens immunized with the above vaccine strains are actually protected against challenge with Delaware (about 60%) and GLS (about 30%) variant viruses.

In addition, the immunization with the "Classic" strains of IBDV (see, Table 4) that is routinely conducted nowadays renders the immunized birds partially protected only against the Delaware (DEL) and the GLS variant viruses.

A "killed" IBDV vaccine is also available from Intervet Co. in Millsboro, Del. This vaccine is called "Breeder-vac" and contains standard ("classic"), Delaware and GLS variant virus types. The use of the above "live" and "killed" vaccines has the following disadvantages, among others.

The viruses have to be propagated in tissue culture, which is time-consuming and expensive.

In "killed" vaccines, the viruses have to be inactivated prior to use, which requires an additional expensive step.

If the "killed" vaccines are not properly inactivated, a risk of an outbreak of the disease exists and does not provide broad protection to birds against the virus variants and the ensuing disease.

Thus, there is a palpable need for an improved vaccine which is effective in the treatment of IBD caused by various pathogenic IBDV strains.

DISCLOSURE OF THE INVENTION

This invention relates to a biologically pure RNA segment that comprises at least one and up to 20 copies of an RNA sequence encoding at least one copy of a polypeptide of about 30 to 1012 amino acids, the polypeptide having the antibody binding characteristics of at least one US variant of the IBDV VP2 protein selected from the group consisting of E/DEL and GLS.

This invention also relates to a biologically pure DNA segment that comprises a single stranded DNA sequence corresponding to the RNA sequence described above. This DNA segment is also provided as a double stranded DNA segment.

Still part of this invention is a recombinant vector that comprises a vector capable of growing and expressing in a host structural DNA sequences attached thereto; and at least one and up to 20 copies of the DNA segment described above attached in reading frame to the vector. The tandem attachment of a plurality of copies of the DNA segment is also be provided as part of this invention.

Also provided herein is a host transformed with a recombinant vector comprising a vector capable of growing and expressing in a host structural DNA sequences attached thereto and at least one copy of the DNA segment of the invention attached in reading frame to the vector.

This invention also relates to a broad spectrum IBD poultry vaccine that comprises a poultry protecting amount of the recombinant vector described above; and a physiologically acceptable carrier.

Encompassed by this invention is also a biologically pure polypeptide that comprises at least one and up to 20 copies of an amino acid sequence of about 30 to 1012 amino acids encoded by the RNA segment of the invention.

A method of protecting poultry and its progeny from IBD is also part of this invention, the method comprising administering to the poultry an amount of the recombinant vector of the invention that is effective to attain an immunological response that will protect the poultry against the symptoms of IBD.

Other objects, advantages and features of the present invention will become apparent to those skilled in the art from the following discussion.

BEST MODE FOR CARRYING OUT THE INVENTION

This invention arose from a desire to improve on prior art technology relating to the protection of poultry against the newly appearing variants of IBDV in the United States.

This was attempted by studying the structural organization of the IBDV genome, and particularly that of the VP2, VP3 and VP4 proteins of the virus. This invention thus provides a DNA vaccine representative of more than one IBDV VP2 US variant. When this DNA is utilized for vaccinating poultry it conveys a broad protection against subsequent infection by known IBDV variants as well as, it is postulated, subsequently appearing variants. The breadth of protection afforded poultry by this DNA vaccine also extends to other strains of IBDV which are known to diverge to a greater extent from the U.S. strain(s) than the variants amongst themselves.

Thus, it is provided herein a biologically pure RNA segment that comprises at least one and up to 20 copies of an RNA sequence encoding at least one copy of a polypeptide about 30 to 1012 amino acids long, the polypeptide having the antibody binding characteristics of at least one of the U.S. variants of the IBDV VP2 protein. Examples are the GLS and E/DEL variants. The layer segments encode more than sequences belonging to the VP2 protein. Each segment encoding at least about 1012 amino acid sequence comprises the binding capability of the VP2 protein, and sequences corresponding to the VP3 and VP4 IBDV proteins.

Such RNA sequence may encode only one copy of the polypeptide having the antibody binding characteristics of at least one of the U.S. IBDV variants or up to about 20 copies thereof, preferably about 1 to 5 copies thereof, an antibody binding functional fragment thereof, a functional precursor thereof, or combinations thereof. The RNA sequence may further encode at least one copy of a polypeptide having the antibody binding characteristics of the VP2 protein of another U.S. IBDV variant, e.g., the E/DEL, "classic" or GLS variant. The RNA sequence may encode either one of these polypeptides, functional fragments thereof, functional precursors thereof or functional analogs thereof as defined below. In addition, the RNA sequence may further encode the antibody binding activity of the VP2 protein of other IBDV strains, e.g., the Australian IBDV variant (WO88/10298 published Dec. 29, 1988; Hudson et al, Nucleic Acids Res. 14(12):5001–5012 (1986)) or the European IBDV strain (Spies et al, Nucleic Acids Res. 17(19):7982 (1989), the entire texts of which are incorporated herein by reference insofar as they are necessary for the enablement of the German Cu-I (European) and Australian DNA, RNA, polypeptide and related sequences of the VP2 protein.

In one preferred embodiment, the polypeptide encoded by the RNA sequence comprises the antibody binding characteristics of amino acids 200 to 330 of at least one US variant of the VP2 protein (e.g., SEQ ID NO: 34). In another preferred embodiment of the invention the RNA segment comprises about 90 to 9000 bases, more preferably about 150 to 5000 bases, and still more preferably about 300 to 750 bases. One particular clone obtained in the examples of this application is about 3.2 kilobases long.

The RNA sequence may preferably encode at least one copy of a polypeptide fragment of an amino acid sequence such as that of Table 6, 7, and/or 8, analogs thereof having at least one amino acid being different at a position such as positions 5, 74, 84, 213, 222, 239, 249, 253, 254, 258, 264, 269, 270, 272, 279, 280, 284, 286, 297, 299, 305, 318, 321, 323, 326, 328, 330, 332, 433 and combinations thereof, and up to 29 different amino acids, functional fragments thereof, functional precursors thereof and combinations thereof.

The functional precursors of the polypeptides having the antibody binding of the different IBDV VP2 US variants may be about 30 to 1012 amino acids long, and in some circumstances about 100 to 350 amino acids long. However, other polypeptide sizes are also considered to be within the definition of precursors as long as they contain a number greater than the final number of amino acids contained in the corresponding polypeptide having the antibody binding characteristics of at least one of the US variants of the VP2 protein.

The functional fragments of the polypeptide may be about 5 to 450 amino acids long, and more preferably about 10 to 30 amino acids long. These fragments comprise the binding characteristics and/or the amino acid sequence of an epitope that makes the polypeptide antigenic with respect to antibodies raised against IBDV as is known in the art.

The functional polypeptide analogs of the IBDV VP2 protein from the E/DEL and the GLS variants may have the size of the VP2 viral protein, or they may be larger or shorter as was described above for the precursors and fragments thereof. The analogs may have about 1 to 80 variations in the amino acid sequence, preferably about 1 to 30 variations, and more preferably at positions 5, 74, 84, 213, 222, 239, 249, 253, 254, 258, 264, 269, 270, 272, 279, 280, 284, 286, 297, 299, 305, 318, 321, 323, 326, 328, 330, 332, 433 or combinations thereof. However, other positions may be varied by themselves as long as the antigenic binding ability of the polypeptide is not destroyed.

In another embodiment of the invention, the RNA sequence encodes at least one copy of a VP2 protein selected from the group consisting of the GLS IBDV VP2 protein, the E/DEL IBDV VP2 protein, functional analogs thereof, functional fragments thereof, functional precursors thereof and combinations thereof. In a particularly preferred embodiment, the RNA sequence encodes at least one copy of the GLS and one copy of the E/DEL IBDV VP2 proteins, and up to 20 copies, and more preferably 5 to 10 copies thereof.

In still another embodiment, the RNA sequence encodes 1 to 20 copies of the entire sequence of the VP2, VP3 and VP4 proteins or the VP2 and VP4 proteins of IBDV E/DEL, GLS or both.

Also provided herein is a biologically pure DNA segment, comprising a single stranded DNA sequence corresponding to the RNA segment described above. In a particularly preferred embodiment of the invention the DNA segment is double stranded. This DNA sequence encodes the antibody binding characteristics of at least one of the US variants of the IBDV VP2 protein selected from GLS and E/DEL. The isolation and deposit of the GLS virus, as well as its characterization and testing, is disclosed in U.S. Pat. No. 5,064,646, from which this application claims priority. The entire disclosure thereof is incorporated herein by reference.

Because of the degeneracy of the genetic code it is possible to have numerous RNA and DNA sequences that encode a specified amino acid sequence. Thus, all RNA and DNA sequences which result in the expression of a polypeptide having the antibody binding characteristics described herein are encompassed by this invention.

In a particularly preferred embodiment of the invention, the DNA sequence comprises the DNA sequences shown in Tables 6, 7, and/or 8, functional fragments thereof about 10 to 750 base pairs long, and more preferably about 20 to 350 base pairs long, functional precursors thereof about 100 to 1350 base pairs long, and more preferably about 200 to 1000 base pairs long, and analogs thereof about 30 to 1012 base pairs long, and more preferably about 15 to 450 base pairs long, corresponding to the amino acid variations described above for the polypeptide.

A suitable proportion for variations: total number of the DNA, RNA and amino acid sequences is about 0.1 to 10%, and more preferably about 1 to 5%. However, other percentages are also contemplated as long as the functionality of the product as described above is preserved.

Also provided herein is a recombinant vector that comprises a vector capable of growing and expressing in a host structural DNA sequences attached thereto; and at least one and up to about 20 copies of the DNA segment of the invention, the segment being operatively linked to the vector.

The recombinant vector may also comprise other necessary sequences such as expression control sequences, markers, amplifying genes, signal sequences, promoters, and the like, as is known in the art.

Useful vectors for this purpose are plasmids, and viruses such as baculoviruses, herpes viruses (HVT) and pox viruses, e.g., fowl pox virus, and the like. A particularly preferred vector comprises a known recombinant fowl pox virus system (Boyle and Coupar, Virus Research 10:343–356 (1988); Taylor, J. et al., J. Virology 64:1441–1450 (1990), the entire texts of which are incorporated herein by reference to the extent necessary to enable the preparation and use of the pox virus vector and its utilization in a poultry vaccine).

In a particularly preferred embodiment of the invention, the recombinant vector comprises a further DNA sequence encoding at least one polypeptide affording protection against other diseases produced by agents such as bronchitis virus, avian reo virus, chicken anemia agent or Newcastle disease virus (NDV), among others. These DNA sequences are operatively attached to the recombinant vector in reading frame so they can be expressed in a host. The different structural DNA sequences carried by the vector may be separated by termination and start sequences so that the proteins will be expressed separately or they may be part of a single reading frame and therefore be produced as a fusion protein by methods known in the art (Taylor et al., supra).

Also provided herein is a host transformed with the recombinant vector of the invention. The host may be a eukaryotic or a prokaryotic host. Suitable examples are *E coli*, insect cell lines such as Sf-9, chicken embryo fibroblast (CEF) cells, chicken embryo kidney (CEK) cells, and the like. The latter two cell lines are useful in propagating the HVT and pox viruses. For combination vaccines, inactivated antigens can be added to the IBDV of the present invention in a dosage which fulfills the requirements or inactivated vaccines according to 99 C.F.R. 113–120, in particular, for combined vaccines containing New Castle Disease Virus (NDV), the requirements of 9 C.F.R. 113–125. However, other hosts and vectors may also be utilized as is known in the art.

Also part of this invention is a broad spectrum IBDV poultry vaccine comprising a poultry protecting amount of a recombinant vector comprising a vector that grows and expresses in a host structural DNA sequences attached thereto and at least one copy of a DNA segment in accordance with this invention attached in reading frame to the vector; and a physiologically acceptable carrier.

The vaccine according to the invention is administered in amounts sufficient to stimulate the immune system and confer resistance to IBD. The vaccine is preferably administered in a dosage ranging from about log 2 to about log 5 $EID_{50}$ (Embryo Infective $Dose_{50}$), and more preferably about log 3 to about log 4 $EID_{50}$. The amounts used when the vaccine is administered to poultry may thus be varied. Suitable amounts are about $10^2$ to $10^6$ plaque forming units (pfu) of the recombinant vector, and more preferably about $10^3$ to $10^4$ pfu units thereof. The animals, 6 weeks or older, may be administered about 0.01 to 2 ml of the vaccine, and more preferably about 0.1 to 1 ml of the vaccine with a needle by the, e.g., wing-web method. Suitably, the virus titre may be about $10^4$ to $10^7$ pfu/ml when reconstituted in a pharmaceutically-acceptable sterile carrier. The vaccine may be provided in powder form as a unit form, or in about 1–1000 doses of vaccine per sealed container, and more preferably about 10 to 100 doses.

Physiologically acceptable carriers for vaccination of poultry are known in the art and need not be further described herein. In addition to being physiologically acceptable to the poultry the carrier must not interfere with the immunological response elicited by the vaccine and/or with the expression of its polypeptide product.

Other additives, such as adjuvants and stabilizers, among others, may also be contained in the vaccine in amounts known in the art. Preferably, adjuvants such as aluminum hydroxide, aluminum phosphate, plant and animal oils, and the like, are administered with the vaccine in amounts sufficient to enhance the immune response to the IBDV. The amount of adjuvant added to the vaccine will vary depending on the nature of the adjuvant, generally ranging from about 0.1 to about 100 times the weight of the IBDV, preferably from about 1 to about 10 times the weight of the IBDV.

The vaccine of the present invention may also contain various stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization.

The attenuated vaccine can be administered by any suitable known method of inoculating poultry including nasally, ophthalmically, by injection, in drinking water, in the feed, by exposure, and the like. Preferably, the vaccine is administered by mass administration techniques such as by placing the vaccine in drinking water or by spraying the animals' environment. A vaccine according to the present invention can be administered by injection. When administered by injection, the vaccines are preferably administered parenterally. Parenteral administration as used herein means administration by intravenous, subcutaneous, intramuscular, or intraperitoneal injection. Known techniques such as Beak-o-Vac administration are preferred.

The vaccine of the present invention is administered to poultry to prevent IBD anytime before or after hatching. Preferably, the vaccine is administered prior to the time of birth and after the animal is about 6 weeks of age. Poultry is defined to include chickens, roosters, hens, broilers, roasters, breeders, layers, turkeys and ducks.

The vaccine may be provided in a sterile container in unit form or in other amounts. It is preferably stored frozen, below $-20°$ C., and more preferably below $-70°$ C. It is thawed prior to use, and may be refrozen immediately thereafter. For administration to poultry the recombinant DNA material or the vector may be suspended in a carrier in an amount of about $10^4$ to $10^7$ pfu/ml, and more preferably about $10^5$ to $10^6$ pfu/ml of a carrier such as a saline solution. Other carriers may also be utilized as is known in the art. Examples of pharmaceutically acceptable carriers are diluents and inert pharmaceutical carriers known in the art. Preferably, the carrier or diluent is one compatible with the administration of the vaccine by mass administration techniques. However, the carrier or diluent may also be compatible with other administration methods such as injection, eye drops, nose drops, and the like.

Also provided herein is a biologically pure polypeptide that comprises at least one copy of an amino acid sequence of about 30 to 1012 amino acids encoded by the DNA segment described above. The amino acid sequence of the polypeptide is also that encoded by the RNA segment of this invention.

As in the case of the RNA and DNA segments described above, the amino acid sequence may comprise at least one and up to 20 copies of the about 30 to 1012 amino acids long polypeptide, the polypeptide having the antibody binding characteristics of at least one U.S. variant of the IBDV VP2 protein, functional precursors thereof, functional fragments thereof, functional analogs thereof and functional combinations thereof as described above.

Each amino acid sequence of the polypeptide may be about 30 to 1012 amino acids long, and more preferably about 100 to 800 amino acids long; each sequence of the functional precursors thereof may be about 40 to 2000 amino acids long, and more preferably about 50 to 1500 amino acids long; each sequence of the functional fragments thereof may be about 5 to 500 amino acids long, and more preferably about 10 to 350 amino acids long; and each sequence of the functional analogs may be about 30 to 1012 amino acids long, and more preferably about 100 to 800 amino acids long. The number and type of point variations the polypeptide has remains within that described above for the RNA and DNA segments.

In particularly preferred embodiments, the polypeptide comprises the amino acid sequence shown in Tables 6, 7 and/or 8. In another preferred embodiment it comprises the amino acid sequence shown in Tables 6, 7, and 8. In yet another preferred embodiment the polypeptide comprises the binding characteristics of amino acids 200 to 330 of the VP2 protein. However, the polypeptide may also comprise other sequences such as those of the VP2 proteins of other IBDV variants or functional fragments thereof.

Also provided herein is a method of protecting poultry and its progeny from IBD comprising administering to the poultry an amount of the recombinant vector of this invention effective to attain the desired effect.

Although other amounts may also be administered, each animal may suitably be provided with about $10^2$ to $10^6$ pfu of the DNA, preferably in a carrier, and more preferably about $10^3$ to $10^4$ pfu of DNA per dose. The vaccine may be administered once to afford a certain degree of protection against IBD or it may be repeated at preset intervals. Or the vaccine may suitably be readministered at anytime after hatching. A typical interval for revaccination is about 1 day to 6 months, and more preferably about 10 days to 4 months. However, the vaccine may be administered as a booster at other times as well.

The various products provided herein as part of this invention can be obtained by implementing standard technology available and known to the artisan and materials that are commercially available.

Having now generally described this invention, the same will be better understood by reference to certain specific examples, which are included herein for purposes of illustration only and are not intended to be limiting of the invention or any embodiment thereof, unless so specified.

EXAMPLES

Example 1

IBDV Propagation in Chicken Bursae and its Purification

Two naturally occurring variants of serotype I IBDV were used that are prevalent in the Delmarva Peninsula, the Delaware strain (E/DEL or DEL) J.K. et al, Proc. 20th Nat. Meeting Poultry Health Condemn. (1985)) and the GLS-5 strain (Snyder, D. B. et al, Proc. 23rd Nat. Meeting Poultry Health Condemn., Ocean City, Md. (1988).

The GLS and E/DEL strains of IBDV were propagated in the bursae of pathogen free white Leghorn chickens. Two to three week old chickens were orally inoculated with GLS or E/DEL stock virus (Snyder, D. B. et al, Vet. Immunol. Immunopathol. 9:303–317 (1985)).

Four to five days after infection, the bursae was excised and homogenized in a buffer containing 10 mM Tris-HCl (pH 7.5) and 150 mM NaCl (TNB buffer). An equal volume of TNB buffer was added to facilitate complete emulsification of the tissue.

The homogenate was freeze-thawed three times and sonicated with a large size probe with two 30 second bursts. Cellular debris from virus suspensions was pelleted by centrifugation at 15,000× g for 10 minutes. The supernate was then passed through a 0.8 µ filter and the filtrate separated. The virus present in the filtrate was then pelleted by centrifugation at 50,000× g for 1.5 hours at 4° C.

The pelleted virus was resuspended in 10 ml phosphate buffered saline (PBS) solution, pH 7.2, and then further purified by centrifugation at 90,000× g for 3 hours at 4° C. on discontinuous sucrose gradients (30% to 55% sucrose) (Snyder et al (1985), supra).

The virus band was recovered, diluted with PBS, and repelleted by centrifugation at 50,000× g for 1.5 hours at 4° C.

Example 2

Isolation and Purification of Viral RNA

Total viral RNA was isolated from the virus by treating with proteinase K as follows. The pelleted virus was suspended in a reaction buffer containing 100 mM Tris-HCl, pH 7.5, 12 mM EDTA and 150 mM NaCl, and digested with proteinase K (200 ug/ml final concentration) for 1 hour at 37° C.

The mixture was extracted twice with water-saturated phenol, and twice with a chloroform:isoamyl alcohol mixture (24:1). The RNA present in the aqueous phase was then precipitated by addition of 2.5 volumes of ethanol at –20° C., and recovered by centrifugation.

The extracted viral RNA was purified by fractionation on a low-melting temperature agarose gel (Maniatis, T. et al, Molecular Cloning: A Laboratory Manual. Cold Spring Harbor Laboratory, N.Y. (1982)). The RNA sample was loaded onto a 1% agarose gel and the gel was electrophoresed using a buffer containing 89 mM Tris-borate, 1 mM EDTA and 0.05% ethidium bromide, pH 8.3. Lambda DNA standards digested with Bst EII were also applied to the gel and used as size markers.

The DNA and RNA fragments were stained with ethidium bromide under the above conditions and visualized under a UV light. Electrophoresis was carried out until a large and a small RNA segments of IBDV were well separated. The larger RNA segment of approximately 3400 base pairs was excised from the gel and recovered by phenol extraction as described above.

Example 3

Synthesis of First Strand cDNA and Complementary Strand DNA of Large Genomic Segment of E/DEL and GLS Strains Viral RNAs were denatured as follows prior to cDNA synthesis. About 5 ug of the larger segment of IBDV RNA were placed in 9 ul of 5 mM phosphate buffer, pH 6.8, heated at 100° C. for 2 minutes and then snap-frozen. After thawing the RNA, 1 ul 100 mM methylmercury hydroxide was added thereto, and the mixture was left at room temperature for 10 minutes.

Any methylmercury hydroxide excess was quenched by addition of 2 ul 700 mM 2-mercaptoethanol and further incubation for 5 minutes at room temperature.

Selected primers binding specifically the 3' end of the VP2 gene sequence and the 3' end of the large genomic segment sequence were synthesized and used to prime the cDNA synthesis on the basis of the published sequence of an Australian strain of IBDV (Hudson, P. J. et al, Nucleic Acids Res. 14, 5001–5012, (1986)), and the published sequence of the German Cu-I IBDV strain (Spies et al, Nucleic Acids Res. 17(19):7982 (1989)), respectively.

VP2 primer (SEQ ID NO: 1): 5'-CAATTG-CATGGGCTAG-3'

3' end primer (SEQ ID NO: 2): 5'-AACGATC-CAATTTGGGAT-3'

Random primers were also employed for use if, and when, the synthesized oligonucleotide failed to prime cDNA synthesis. Double stranded cDNA was synthesized according to the method of Gubler and Hoffman (Gubler, U. and Hoffman, B. J. Gene 25, 263–269 (1983)).

The synthesis of first-strand cDNA was carried out in a reaction volume of 50 ul containing 50 mM Tris-HCl, pH8.3, 10 mM $MgCl_2$, 10 mM dithiothreitol, 4 mM sodium pyrophosphate, 1.25 mM dGTP, 1.25 mM dATP, 0.5 mM dCTP, 20 uCi $^{32}$P-dCTP, 5 ug primer, 5 ug RNA and 100 units reverse transcriptase for 1 hour at 42° C. The reaction was terminated by adding 2 ul of 0.5M EDTA, pH 8.0. The reaction products were then extracted with phenol/chloroform (1:1) and precipitated with ethanol out of 2M ammonium acetate.

The synthesis of the second strand of DNA and the formation of double stranded DNA fragments were carried out in a reaction volume of 100 ul containing 20 mM Tris-HCl (pH 7.5), 5 mM $MgCl_2$, 10 mM $(NH_4)_2SO_4$, 100 mM KCl, 0.15 mM β-NAD, 5 ug BSA, 40 uM dNTPs, 1 unit *E. coli* RNase H, 25 units DNA polymerase I and 1 unit *E. coli* DNA ligase. The reaction mixture was sequentially incubated at 12° C. for 1 hour, and at 22° C. for 1 hour, and terminated by addition of 10 ul of 0.5M EDTA, pH 8.0. The reaction products were phenol-extracted and ethanol-precipitated as described above.

Example 4

Ligation of DNA Fragments to a Vector

The double stranded cDNA was blunt-ended with T4 DNA polymerase and then fractionated on a low-melting agarose gel (Maniatis, T. et al, Molecular Cloning: A Laboratory Manual. Cold Spring Harbor Laboratory, N.Y. (1982)).

Large size fragments, e.g., greater than 500 base pairs were recovered from the gel by phenol extraction as described above. EcoRI adapters (Promega Biotech) were ligated to the blunt-ended cDNAs by incubating the mixture at 14° C. overnight in the presence of T4 DNA ligase (Maniatis, T. et al, Molecular Cloning: A Laboratory Manual. Cold Spring Harbor Laboratory, N.Y. (1982)).

EcoRI-ended cDNAs were then phosphorylated in the presence of T4 polynucleotide kinase, ligated with dephosphorylated EcoRI cut pGEM-7Z vector (Promega Biotech), and then used for transformation.

Example 5

Transformation of Bacterial Host With the Recombinant Vector

*E. coli* JM 109 cells were made competent as follows. An overnight culture of *E. coli* JM 109 in 5 ml of Luria-Bertani (LB) broth were used to inoculate 40 ml LB broth (1:100) in a 250 ml Erlenmeyer flask which was gently shaken at 37° C. When the $OD_{550nm}$ reached about 0.5 the flask was chilled in ice and the cells pelleted by centrifugation at 4000× g for 5 minutes at 4° C. The supernate was discarded, and the cells suspended in 20 ml of transformation buffer containing 50 mM $CaCl_2$, 250 mM KCl, 5 mM Tris-HCl, pH 7.5 and 5 mM $MgCl_2$. The cells were then incubated on ice for 20 minutes, pelleted once again by centrifugation, resuspended in 2 ml transformation buffer and left overnight at 4° C.

0.2 ml competent cells were added to the ligated cDNAs and the mixture was first incubated on ice for 1 hour and then at 42° C. for 2 minutes. One ml LB broth was then added and the mixture was incubated at 37° C. for 1 hour.

Example 6

Selection of Hosts Carrying Viral DNA Inserts

The pGEM-7Z plasmid contains a beta-galactosidase gene marker. The transformed mixture was thus plated on culture plates containing ampicillin, isopropylthio-β-D-galactopyranoside (IPTG) and a chromogenic substrate, 5-bromo-4-chloro-3-indolyl-β-D-galactoside (X-Gal) for selection of the recombinants.

Ampicillin resistant white colonies with inserts were selected, propagated and stored in 15% glycerol at −70° C.

Example 7

Screening of Recombinant Clones

The ampicillin resistant white colonies obtained in Example 8 above were screened for the presence of viral-specific sequences by Southern hybridization (Southern, E. M., J. Mol. Biol. 98, 503–517 (1975)).

Briefly, recombinant bacteria harboring the plasmid DNA were propagated in 2 ml of LB broth and plasmid DNA was isolated by an established method (Birnboim, H. C. and Doly, J., Nucleic Acids Res. 7, 1513–1520 (1979)). The purified plasmid DNA was then digested with EcoRI enzyme and separated on 1% agarose gel to determine the size of the inserts. Fragments of Lamda DNA digested with Hind III and Eco RI were used as size markers. The identity of the released inserts was determined by transferring the DNA to a Gene screen plus membrane (DuPont, Inc.) and hybridizing with a $^{32}$P labeled probe.

The probe was prepared by 5'-end labeling the base-hydrolyzed larger segment of the viral RNA with γ-$^{32}$P-ATP and polynucleotide kinase (Richardson, C. C., Proc. Nucleic Acid Res. 2,815–819 (1971)) and denatured by heating at 100° C. for 2 minutes, and then fast cooling to 0° C.

The membrane was pre-hybridized for at least 15 minutes at 42° C. with a pre-hybridization mixture containing 50% formamide, 1M NaCl, 1% SDS and 20% dextran sulfate. 100 ug/ml of denatured salmon sperm DNA and a denatured radioactive probe were then added to the pre-hybridization mixture. The hybridization was carried out for 16 hours at 42° C. with constant agitation.

After hybridization, the membrane was washed twice successively with a buffer containing 0.3M NaCl, 0.03M sodium citrate, pH 7.0 (2×SSC), and 1% SDS at 65° C. for 20 minutes and with 0.1 SSC buffer at room temperature for 20 minutes. Hybridization was detected by autoradiography and positive cDNA clones were then selected with the largest inserts.

The overlapping clones were identified both by hybridization and restriction enzyme mapping.

The different clones mapped as shown in Table 5 below.

Example 8

Mapping of GLS and E/DEL cDNA clones.

The GLS-1, GLS-2 and GLS-4 and E.DEL-2 cDNA clones were completely sequenced and their sequences were compared with the DNA sequence of the Australian strain of IBDV using the "Microgenie" computer program.

On the basis of the sequence homology, the above clones were mapped on the IBDV genomes as shown in Table 5 below.

TABLE 5

IBDV-Large Seqment cDNA Clones
(GLS-1, GLS-2, GLS-3, GLS-4 and E/DEL-2)

```
         1 kb       2 kb      3 kb
5' |------|---------|---------|------| 3'

|-VP2-|| VP4 || VP3 |

|----- GLS-4 -----|

|GLS-1|                |------------|

|-- GLS-2 --|
                                GLS-3
       |-- E.Del-2 --|
```

Example 9

Sequencing of VP2 Gene Fragments of E/Del and GLS IBDV Strains

Recombinant bacteria, each harboring a cDNA segment of the E/DEL and GLS strains of IBDV, were propagated in LB broth containing 100 ug/ml/ampicillin. The large-scale isolation of plasmid DNA was carried out by the alkali lysis method (Birnboim, H. C. and Doly, J., Nucleic Acids Res. 7, 1513–1520, (1979)). The plasmid DNA was then purified by cesium chloride gradient centrifugation (Maniatis, T. et al, Molecular Cloning: A Laboratory Manual. Cold Spring Harbor Laboratory, New York (1982)).

The nucleotide sequence of these cDNA clones was determined by a modification of the dideoxy chain termination method (Sanger, F. et al, Proc. Natl. Acad. Sci. 74, 5463–5467 (1977)) using a Sequenase$^R$ System kit (U.S. Biochemical Corp.) with SP6 and T7 promoter primers (Promega Biotech).

A set of selected oligonucleotides, corresponding to the VP2 region of the large genomic segment of IBDV, was synthesized and used as primers in the sequencing reactions. Examples are as follows (5' to 3' end).

(1) TATTCTGTAACCAGGTT (SEQ ID NO: 3)
(2) CACTATCTCCAGTTTGAT (SEQ ID NO: 4)
(3) TACGAGGACTGACGGGTCTT (SEQ ID NO: 5)

The labeled fragments were fractionated on 45 or 60 cm 8% polyacrylamide-urea gels and detected by autoradiography.

Example 10

Sequencing of VP3 and VP4 Gene Fragments of GLS IBDV Strain

The nucleotide sequence of the cDNA clones, GLS-3 and GLS-4, was determined by a modification of the dideoxy chain termination method (for reference, see Example 9) using a "Sequenase" System kit (U.S. Biochemical Corp.) with SP6 and T7 promoter primers (Promega Biotech).

A set of selected oligonucleotides corresponding to the VP3 and VP4 region of the large genomic segment of IBDV, was synthesized and used as primers in the sequencing reactions. Examples are as follows (5' to 3' end).

(1) TTCAAAGACATAATCCGG (SEQ ID NO: 6)
(2) GGGTGAAGCAAGAATCCC (SEQ ID NO: 7)
(3) GTGCGAGAGGACCTCCAA (SEQ ID NO: 8)
(4) GTATGGAAGGTTGAGGTA (SEQ ID NO: 9)
(5) GGGATTCTTGCTTCACCC (SEQ ID NO 10)
(6) ACGTTCATCAAACGTTTCCC (SEQ ID NO: 11)
(7) TTGCAAACGCACCACAAGCA (SEQ ID NO: 12)
(8) CGGATCCAATTTGGGAT (SEQ ID NO: 13)
(9) GTGTCGGGAGACTCCCA (SEQ ID NO: 14)

Sequences were obtained for several fragments and the information put together in accordance with the information obtained from overlapping segments. The DNA sequence obtained for the E/DEL viral fragment (SEQ ID NO: 15) is shown in Table 6 below and for the GLS fragments (SEQ ID NO: 18) in Table 7 below.

Example 11

Comparison of DNA Sequences with Computerized Program

Nucleotide sequence data were entered into an IBM computer with the aid of a gel reader and analyzed with a "Microgenie" software program (Beckman). This program provides information of the following characteristics of the strains of IBDV.

(1) The presence of an open reading frame from a major initiation site within the consensus eukaryotic initiation site sequences (Kozak, M., Microbiol. Rev. 47, 1–49, (1983)).

(2) The complete predicted (deduced) amino acid sequences.

(3) Comparisons and homology alignments of obtained sequences with the published sequence data of an Australian strain of IBDV (Hudson, P. J. et al, Nucleic Acids Res. 14, 5001–5012, (1986)) and the German Cu-I IBDV strain (Spies et al (1989), supra).

Example 12

DNA and Deduced Amino Acid Sequences of E/DEL-2 Clone

The following Table 6 shows the DNA sequence obtained for an E/Del-2 clone containing 1471 nucleotides (SEQ ID NO: 15). Table 6 also shows the corresponding amino acid sequence (SEQ ID NO: 16–17) deduced from the DNA sequence as discussed above.

TABLE 6

DNA and Deduced Amino Acid Sequences of E/DEL-2 Clone

```
                              30                                                60
CTA CAA TGC TAT CAT TGA TGG TTA GTA GAG ATC AGA CAA ACG ATC GCA GCG ATG ACA AAC
Leu Gln Cys Tyr His End Trp Leu Val Glu Ile Arg Gln Thr Ile Ala Ala Met Thr Asn
                              90                                               120
CTG CAA GAT CAA ACC CAA CAG ATT GTT GGG TTT ATA CGG AGC CTT TTG ATG CCA ACA ACC
Leu Gln Asp Gln Thr Gln Gln Ile Val Pro Phe Ile Arg Ser Leu Leu Met Pro Thr Thr
                             150                                               180
GGA CCG GCG TCC ATT CCG GAC GAC ACC CTG GAG AAG CAC ACT CTC AGG TCA GAG ACC TGG
Gly Pro Ala Ser Ile Pro Asp Asp Thr Leu Glu Lys His Thr Leu Arg Ser Glu Thr Ser
                             210                                               240
ACC TAC AAT TTG ACT GTG GGG GAC ACA GGG TCA GGG CTA ATT GTC TTT TTT CCT GGA TTC
Thr Tyr Asn Leu Thr Val Gly Asp Thr Gly Ser Gly Leu Ile Val Phe Phe Pro Gly Phe
                             270                                               300
CCT GGC TCA ATT GTG GGT GCT CAC TAC ACA CTG CAG AGC AAT GGG AAC TAC AAG TTC GAT
Pro Gly Ser Ile Val Gly Ala His Tyr Thr Leu Gln Ser Asn Gly Asn Tyr Lys Phe Asp
                             330                                               360
CAG ATG CTC CTG ACT GCC CAG AAC CTA CCG GCC AGC TAC AAC TAC TGC AGG CTA GTG AGT
Gln Met Leu Leu Thr Ala Gln Asn Leu Pro Ala Ser Tyr Asn Tyr Cys Arg Leu Val Ser
                             390                                               420
TGG AGT CTC ACA GTA AGG TCA AGC ACA CTC CCT GGT GGC GTT TAT GCA CTA AAC GGG ACC
Arg Ser Leu Thr Val Arg Ser Ser Thr Leu Pro Gly Gly Val Tyr Ala Leu Asn Gly Thr
                             450                                               480
ATA AAC GCC GTG ACC TTC CAA GGA AGC CTG AGT GAA CTG ACA GAT GTT AGC TAC AAC GGG
Ile Asn Ala Val Thr Phe Gln Gly Ser Leu Ser Glu Leu Thr Asp Val Ser Tyr Asn Gly
                             510                                               540
TTG ATG TGT GCA ACA GCC AAC ATC AAC GAC AAA ATT GGG AAC GTC CTA GTA GGG GAA GGG
Leu Met Ser Ala Thr Ala Asn Ile Asn Asp Lys Ile Gly Asn Val Leu Val Gly Glu Gly
                             570                                               600
GTA ACC GTC CTC AGC TTA CCC ACA TCA TAT GAT CTT GGG TAT GTG AGG CTT GGT GAC CCC
Val Thr Val Leu Ser Leu Pro Thr Ser Tyr Asp Leu Gly Tyr Val Arg Leu Gly Asp Pro
                             630                                               660
ATA CCC GGT ATA GGG CTT GAC CCA AAA ATG GTA GGA ACA TGT GAC AGC AGT GAC AGG CCC
Ile Pro Ala Ile Gly Leu Asp Pro Lys Met Val Ala Thr Cys Asp Ser Ser Asp Arg Pro
                             690                                               720
AGA GTC TAC ACC ATA ACT GCA GCC GAT AAT TAC CAA TTC TCA TCA CAG TAC CAA ACA GGT
Arg Val Tyr Thr Ile Thr Ala Ala Asp Asn Tyr Gln Phe Ser Ser Gln Tyr Gln Thr Gly
                             750                                               780
GGG GTA ACA ATC ACA CTG TTC TCA GCC AAC ATT GAT GCC ATC ACA AGT CTC AGC GTT GGG
Gly Val Thr Ile Thr Leu Phe Ser Ala Asn Ile Asp Ala Ile Thr Ser Leu Ser Val Gly
                             810                                               840
GGA GAG CTC GTG TTC AAA ACA AGC GTC CAA AGC CTT GTA CTG GGC GCC ACC ATC TAC CTT
Gly Glu Leu Val Phe Lys Thr Ser Val Gln Ser Leu Val Leu Gly Ala Thr Ile Tyr Leu
                             870                                               900
ATA GGC TTT GAT GGG ACT GCG GTA ATC ACC AGA GCT GTG GCC GCA AAC AAT GGG CTG ACG
Ile Gly Phe Asp Gly Thr Ala Val Ile Thr Arg Ala Val Ala Ala Asn Asn Gly Leu Thr
                             930                                               960
GCC GGC ATC GAC AAT CTT ATG CCA TTC AAT CTT GTG ATT CCA ACC AAT GAG ATA ACC CAG
Ala Gly Ile Asp Asn Leu Met Pro Phe Asn Leu Val Ile Pro Thr Asn Glu Ile Thr Gln
                             990                                              1020
CCA ATC ACA TCC ATC AAA CTG GAG ATA GTG ACC TCC AAA AGT GAT GGT CAG GCA GGG GAA
Pro Ile Thr Ser Ile Lys Leu Glu Ile Val Thr Ser Lys Ser Asp Gly Gln Ala Gly Glu
                            1050                                              1080
CAG ATG TCA TGG TCG GCA AGT GGG AGC CTA GCA GTG ACG ATC CAT GGT GGC AAC TAT CCA
Gln Met Ser Trp Ser Ala Ser Gly Ser Leu Ala Val Thr Ile His Gly Gly Asn Tyr Pro
                            1110                                              1140
GGA GCC CTC CGT CCC GTC ACA CTA GTG GCC TAC GAA AGA GTG GCA ACA GGA TCT GTC GTT
Gly Ala Leu Arg Pro Val Thr Leu Val Ala Tyr Glu Arg Val Ala Thr Gly Ser Val Val
                            1170                                              1200
ACG GTC GCT GGG GTG AGC AAC TTC GAG CTG ATC CCA AAT CCT GAA CTA GCA AAG AAC CTG
Thr Val Ala Gly Val Ser Asn Phe Glu Leu Ile Pro Asn Pro Glu Leu Ala Lys Asn Leu
```

TABLE 6-continued

DNA and Deduced Amino Acid Sequences of E/DEL-2 Clone

```
                             1230                                                    1260
GTT ACA GAA TAT GGC CGA TTT GAC CCA GGA GCC ATG AAC TAC ACG AAA TTG ATA CTG AGT
Val Thr Glu Tyr Gly Arg Phe Asp Pro Gly Ala Met Asn Tyr Thr Lys Leu Ile Leu Ser
                             1290                                                    1320
GAG AGG GAC CGC CTT GGC ATC AAG ACC GTC TGG CCA ACA AGG GAG TAC ACT GAC TTT CGT
Gln Arg Asp Arg Leu Gly Ile Lys Thr Val Trp Pro Thr Arg Glu Tyr Thr Asp Phe Arg
                             1350                                                    1380
GAG TAC TTC ATG GAG GTG GCC GAC CTC AAC TCT CCC CTG AAG ATT GCA GGA GCA TTT GGC
Gln Tyr Phe Met Glu Val Ala Asp Leu Asn Ser Pro Leu Lys Ile Ala Gly Ala Phe Gly
                             1410                                                    1440
TTC AAA GAC ATA ATC CGG GCC ATA AGG AGG ATA GCT GTA CCG GTG GTC TCT ACA TTG TTC
Phe Lys Asp Ile Ile Arg Ala Ile Arg Arg Ile Ala Val Pro Val Val Ser Thr Leu Phe
                             1470
CCA CCT GCC GCT CCT GTA GCC CAT GCA ATT G
Pro Pro Ala Ala Pro Val Ala His Ala Ile
```

Example 13

DNA and Deduced Amino Acid Sequences for GLS-1, GLS-2, GLS-3 and GLS-4 Clones

The following Table 7 provides the DNA sequence (SEQ ID NO: 18) of the GLS-1, GLS-2, GLS-3 and GLS-4 clone obtained above and the amino acid sequence (SEQ ID NO: 19) deduced therefrom obtained from the DNA sequences with the aid of a computerized program.

TABLE 7

DNA Sequence and Deduced Amino Acid Sequence for GLS-1, GLS-2, GLS-3 and GLS-4 Clones

```
                                                                                      CC
                             32                                                       62
CCG GGG GAG TCA CCC GGG GAC AGG CCG TCA AGG CCT TGT TCC AGG ATG GAA CTC CCC CTT
                             92                                                       122
CTA CAA TGC TAT CAT TGA TGG TTA GTA GAG ATC GGA CAA ACG ATC GCA GCG ATG ACA AAC
                                                                         Met Thr Asn
                             152                                                      182
CTG CAA GAT CAA ACC CAA CAG ATT GTT CCG TTC ATA CGG AGC CTT CTG ATG CCA ACA ACC
Leu Gln Asp Gln Thr Gln Gln Ile Val Pro Phe Ile Arg Ser Leu Leu Met Pro Thr Thr
                             212                                                      242
GGA CCG GCG TCC ATT CCG GAC GAC ACC CTG GAG AAG CAC ACT CTC AGG TCA GAG ACC TCG
Gly Pro Ala Ser Ile Pro Asp Asp Thr Leu Glu Lys His Thr Leu Arg Ser Glu Thr Ser
                             272                                                      302
ACC TAC AAT TTG ACT GTG GGG GAC ACA GGG TCA GGG CTA ATT GTC TTT TTC CCT GGA TTC
Thr Tyr Asn Leu Thr Val Gly Asp Thr Gly Ser Gly Leu Ile Val Phe Phe Pro Gly Phe
                             332                                                      362
CCT GGC TCA ATT GTG GGT GCT CAC TAC ACA CTG CAG AGC AAT GGG AAC TAC AAG TTC GAT
Pro Gly Ser Ile Val Gly Ala His Tyr Thr Leu Gln Ser Asn Gly Asn Tyr Lys Phe Asp
                             392                                                      422
CAG ATG CTC CTG ACT GCC CAG AAC CTA CCG GCC AGC TAC AAC TAC TGC AGG CTA GTG AGT
Gln Met Leu Leu Thr Ala Gln Asn Leu Pro Ala Ser Tyr Asn Tyr Cys Arg Leu Val Ser
                             452                                                      482
CGG AGT CTC ACA GTA AGG TCA AGC ACA CTC CCT GGT GGC GTT TAT GCA CTA AAC GGC ACC
Arg Ser Leu Thr Val Arg Ser Ser Thr Leu Pro Gly Gly Val Tyr Ala Leu Asn Gly Thr
                             512                                                      542
ATA AAC GCC GTG ACC TTC CAA GGA AGC CTG AGT GAA CTG ACA GAT GTT AGC TAC AAT GGG
Ile Asn Ala Val Thr Phe Gln Gly Ser Leu Ser Glu Leu Thr Asp Val Ser Tyr Asn Gly
                             572                                                      602
TTG ATG TCT GCA ACA GCC AAC ATC AAC GAC AAA ATT GGG AAC GTC CTA GTA GGG GAA GGG
Leu Met Ser Ala Thr Ala Asn Ile Asn Asp Lys Ile Gly Asn Val Leu Val Gly Glu Gly
```

TABLE 7-continued

DNA Sequence and Deduced Amino Acid Sequence for GLS-1, GLS-2, GLS-3 and GLS-4 Clones

```
                            632                                                           662
GTT ACT GTC GTC AGC TTA CCC ACA TCA TAT GAT CTT GGG TAT GTG AGG CTT GGT GAC CCC
Val Thr Val Val Ser Leu Pro Thr Ser Tyr Asp Leu Gly Tyr Val Arg Leu Gly Asp pro 692                                                           722
ATA CCC GCT ATA GGG CTT GAC CCA AAA ATG GTA GCA ACA TGT GAC AGC AGT GAC AGG CCC
Ile Pro Ala Ile Gly Leu Asp Pro Lys Met Val Ala Thr Cys Asp Ser Ser Asp Arg Pro 752                                                           782
AGA GTC TAC ACC ATA ACT GCA GCT GAT GAT TAC CAA TTC TCA TCA CAG TAC CAA ACA GGT
Arg Val Tyr Thr Ile Thr Ala Ala Asp Asp Tyr Gln Phe Ser Ser Gln Tyr Gln Thr Gly 812                                                           842
GGG GTA ACA ATC ACC CTG TTC TCA GCC AAC ATT GAT GCC ATC ACA AGC CTC AGC GTT GGG
Gly Val Thr Ile Thr Leu Phe Ser Ala Asn Ile Asp Ala Ile Thr Ser Leu Ser Val Gly 872                                                           902
GGA GAG CTC GTG TTT AAA ACA AGC GTC CAC AGC CTT GTA CTG GGC GCC ACC ATC TAC CTT
Gly Glu Leu Val Phe Lys Thr Ser Val His Ser Leu Val Leu Gly Ala Thr Ile Tyr Leu 932                                                           962
ATA GGC TTT GAT GGG TCT GCG GTA ATC ACT AGA GCT GTG GCC GCA AAC AAT GGG CTG ACG
Ile Gly Phe Asp Gly Ser Ala Val Ile Thr Arg Ala Val Ala Ala Asn Asn Gly Leu Thr 992                                                          1022
ACC GGC ACC GAC AAT CTT ATG CCA TTC AAT CTT GTG ATT CCA ACC AAC GAG ATA ACC CAG
Thr Gly Thr Asp Asn Leu Met Pro Phe Asn Leu Val Ile Pro Thr Asn Glu Ile Thr Gln 1052                                                          1082
CCA ATC ACA TCC ATC AAA CTG GAG ATA GTG ACC TCC AAA AGT GGT GGT CAG GAA GGG GAC
Pro Ile Thr Ser Ile Lys Leu Glu Ile Val Thr Ser Lys Ser Gly Gly Gln Glu Gly Asp 1112                                                          1142
CAG ATG TCA TGG TCG GCA AGT GGG AGC CTA GCA GTG ACG ATT CAT GGT GGC AAC TAT CCA
Gln Met Ser Trp Ser Ala Ser Gly Ser Leu Ala Val Thr Ile His Gly Gly Asn Tyr Pro 1172                                                          1202
GGG GCC CTC CGT CCC GTC ACA CTA GTA GCC TAC GAA AGA GTG GCA ACA GGA TCT GTC GTT
Gly Ala Leu Arg Pro Val Thr Leu Val Ala Tyr Glu Arg Val Ala Thr Gly Ser Val Val 1232                                                          1262
ACG GTC GCT GGG GTG AGC AAC TTC GAG CTG ATC CCA AAT CCT GAA CTA GCA AAG AAC CTG
Thr Val Ala Gly Val Ser Asn Phe Glu Leu Ile Pro Adn Pro Glu Leu Ala Lys Asn Leu 1292                                                          1322
GTT ACA GAA TAC GGC CGA TTT GAC CCA GGA GCC ATG AAC TAC ACA AAA TTG ATA CTG AGT
Val Thr Glu Tyr Gly Arg Phe Asp Pro Gly Ala Met Asn Tyr Thr Lys Leu Ile Leu Ser 1352                                                          1382
GAG AGG GAC CGC CTT GGC ATC AAG ACA GTC TGG CCG ACA ACA GAG TAC ACC GAC TTT CGT
Glu Arg Asp Arg Leu Gly Ile Lys Thr Val Trp Pro Thr Arg Glu Tyr Thr Asp Phe Arg 1412                                                          1442
GAG TAC TTC ATG GAG GTG GCC GAC CTC AGC TCT CCC CTG AAG ATT GCA GGA GCA TTT GGC
Glu Tyr Phe Met Glu Val Ala Asp Leu Ser Ser Pro Leu Lys Ile Ala Gly Ala Phe Gly 1472                                                          1502
TTC AAA GAC ATA ATC CGG GCC ATA AGG AGG ATA GCT GTG CCG GTG GTC TCC ACA TTG TTC
Phe Lys Asp Ile Ile Arg Ala Ile Arg Arg Ile Ala Val Pro Val Val Ser Thr Leu Phe 1532                                                          1562
CCA CCT GCC GCT CCC CTG GCC CAT GCA ATT GGG GAA GGT GTA GAC TAC CTG CTG GGT GAT
Pro Pro Ala Ala Pro Leu Ala His Ala Ile Gly Glu Gly Val Asp Tyr Leu Leu Gly Asp 1592                                                          1622
GAG GCA CAG GCT GCT TCA GGA ACT GCT CGA GCC GCG TCA GGA AAA GCA AGG GCT GCC TCA
Glu Ala Gln Ala Ala Ser Gly Thr Ala Arg Ala Ala Ser Gly Lys Ala Arg Ala Ala Ser 1652                                                          1682
GGC CGC ATA AGG CAG CTG ACT CTC GCC GCC GAC AAG GGG TAC GAG GTA GTC GCG AAT CTA
Gly Arg Ile Arg Gln Leu Thr Leu Ala Ala Asp Lys Gly Tyr Glu Val Val Ala Asn Leu 1712                                                          1742
TTC CAG GTG CCC CAG AAT CCC GTA GTC GAC GGG ATT CTT GCT TCA CCC GGG ATA CTC CGC
Phe Gln Val Pro Gln Asn Pro Val Val Asp Gly Ile Leu Ala Ser Pro Gly Ile Leu Arg 1772                                                          1802
GGT GCA CAC AAC CTC GAC TGC GTG TTA AGA GAG GGC GCC ACG CTA TTC CCT GTG GTC ATC
Gly Ala His Asn Leu Asp Cys Val Leu Arg Glu Gly Ala Thr Leu Phe Pro Val Val Ile
```

TABLE 7-continued

DNA Sequence and Deduced Amino Acid Sequence for GLS-1, GLS-2, GLS-3 and GLS-4 Clones

```
                                    1832                                                              1862
ACG ACA GTG GAA GAC GCC ATG ACA CCC AAA GCA CTA AAC AGC AAA ATG TTT GCT GTC ATT
Thr Thr Val Glu Asp Ala Met Thr Pro Lys Ala Leu Asn Ser Lys Met Phe Ala Val Ile 1892                                                              1922
GAA GGC GTG CGA GAG GAC CTC CAA CCT CCA TCT CAA AGA GGA TCC TTC ATA CGA ACT CTC
Glu Gly Val Arg Glu Asp Leu Gln Pro Pro Ser Gln Arg Gly Ser Phe Ile Arg Thr Leu 1952                                                              1982
TCC GGA CAC AGA GTC TAT GGA TAT GCT CCA GAT GGG GTA CTT CCA CTG GAG ACT GGG AGA
Ser Gly His Arg Val Tyr Gly Tyr Ala Pro Asp Gly Val Leu Pro Leu Glu Thr Gly Arg 2012                                                              2042
GAC TAC ACC GTT GTC CCA ATA GAT GAT GTC TGG GAC GAC AGC ATT ATG CTG TCC AAA GAC
Asp Tyr Thr Val Val Pro Ile Asp Asp Val Trp Asp Asp Ser Ile Met Leu Ser Lys Asp 2072                                                              2102
CCC ATA CCT CCT ATT GTG GGA AAC AGT GGA AAC CTA GCC ATA GCT TAC ATG GAT GTG TTT
Pro Ile Pro Pro Ile Val Gly Asn Ser Gly Asn Leu Ala Ile Ala Tyr Met Asp Val Phe 2132                                                              2162
CGA CCC AAA GTC CCC ATC CAT GTG GCC ATG ACG GGA GCC CTC AAC GCT TGT GGC GAG ATT
Arg Pro Lys Val Pro Ile His Val Ala Met Thr Gly Ala Leu Asn Ala Cys Gly Glu Ile 2192                                                              2222
GAG AAA ATA AGC TTT AGA AGC ACC AAG CTC GCC ACC GCA CAC CGG CTT GGC CTC AAG TTG
Glu Lys Ile Ser Phe Arg Ser Thr Lys Leu Ala Thr Ala His Arg Leu Gly Leu Lys Leu 2252                                                              2282
GCT GGT CCC GGA GCA TTT GAT GTA AAC ACC GGG CCC AAC TGG GCA ACG TTC ATC AAA CGT
Ala Gly Pro Gly Ala Phe Asp Val Asn Thr Gly Pro Asn Trp Ala Thr Phe Ile Lys Arg 2312                                                              2342
TTC CCT CAC AAT CCA CGC GAC TGG GAC AGG CTC CCC TAC CTC AAC CTT CCA TAC CTT CCA
Phe Pro His Asn Pro Arg Asp Trp Asp Arg Leu Pro Tyr Leu Asn Leu Pro Tyr Leu Pro 2372                                                              2402
CCC AAT GCA GGA CGC CAG TAC CAC CTC GCC ATG GCC GCA TCA GAG TTC AAG GAG ACC CCT
Pro Asn Ala Gly Arg Gln Tyr His Leu Ala Met Ala Ala Ser Glu Phe Lys Glu Thr Pro 2432                                                              2462
GAA CTC GAG AGC GCC GTC AGG GCC ATG GAA GCA GCA GCC AGT GTA GAC CCA CTG TTC CAA
Glu Leu Glu Ser Ala Val Arg Ala Met Glu Ala Ala Ala Ser Val Asp Pro Leu Phe Gln 2492                                                              2522
TCT GCA CTC AGT GTG TTC ATG TGG CTG GAA GAG AAT GGG ATT GTG ACT GAC ATG GCC AAC
Ser Ala Leu Ser Val Phe Met Trp Leu Glu Glu Asn Gly Ile Val Thr Asp Met Ala Asn 2552                                                              2582
TTC GCA CTC AGC GAC CCG AAC GCC CAT CGG ATG CGA AAC TTT CTT GCA AAC GCA CCA CAA
Phe Ala Leu Ser Asp Pro Asn Ala His Arg Met Arg Asn Phe Leu Ala Asn Ala Pro Gln 2612                                                              2642
GCA GGT AGC AAG TCT CAA AGG GCC AAA TAC GGG ACA GCA GGC TAC GGA GTG GAG GCC CGG
Ala Gly Ser Lys Ser Gln Arg Ala Lys Tyr Gly Thr Ala Gly Tyr Gly Val Glu Ala Arg 2672                                                              2702
GGC CCC ACA CCA GAA GAA GCA CAG AGG GAA AAA GAC ACA CGG ATC TCA AAG AAG ATG GAG
Gly Pro Thr Pro Glu Glu Ala Gln Arg Glu Lys Asp Thr Arg Ile Ser Lys Lys Met Glu 2732                                                              2762
ACC ATG GGC ATC TAC TTT GCA ACA CCA GAA TGG GTA GCA CTC AAT GGG CAC CGA GGG CCA
Thr Met Gly Ile Tyr Phe Ala Thr Pro Glu Trp Val Ala Leu Asn Gly His Arg Gly Pro 2792                                                              2822
AGC CCC GGC CAG CTA AAG TAC TGG CAG AAC ACA CGA GAA ATA CCG GAC CCA AAC GAG GAC
Ser Pro Gly Gln Leu Lys Tyr Trp Gln Asn Thr Arg Glu Ile Pro Asp Pro Asn Glu Asp 2852                                                              2882
TAT CTA GAC TAC GTG CAT GCA GAG AAG AGC CGG TTG GCA TCA GAA GAA CAA ATC CTA AGG
Tyr Leu Asp Tyr Val His Ala Glu Lys Ser Arg Leu Ala Ser Glu Glu Gln Ile Leu Arg 2912                                                              2942
GCA GCT ACG TCG ATC TAC GGG GCT CCA GGA CAG GCA GAG CCA CCC CAA GCT TTC ATA GAC
Ala Ala Thr Ser Ile Tyr Gly Ala Pro Gly Gln Ala Glu Pro Pro Gln Ala Phe Ile Asp
```

TABLE 7-continued

DNA Sequence and Deduced Amino Acid Sequence for GLS-1, GLS-2, GLS-3 and GLS-4 Clones

```
                                                                      2972                                                        3002
GAA GTT GCC AAA GTC TAT GAA ATC AAC CAT GGA CGT GGC CCA AAC CAA GAA CAG ATG AAA
Glu Val Ala Lys Val Tyr Glu Ile Asn His Gly Arg Gly Pro Asn Gln Glu Gln Met Lys 3032                                                                3062
GAT CTG CTC TTG ACT GCG ATG GAG ATG AAG CAT CGC AAT CCC AGG CGG GCT CCA CCA AAG
Asp Leu Leu Leu Thr Ala Met Glu Met Lys His Arg Asn Pro Arg Aeg Ala Pro Pro Lys 3092                                                                3122
CCC AAG CCA AGA CCC AAC GCT CCA ACG CAG AGA CCC CCT GGT CGG CTG GGC CGC TGG ATC
Pro Lys Pro Arg Pro Asn Ala Pro Thr Gln Arg Pro Pro Gly Arg Leu Gly Arg Trp Ile 3152                                                                3182
AGG ACT GTC TCT GAT GAG GAC CTT GAG TGA GGC TCC TGG GAG TCT CCC GAC ACC ACC CGC
Arg Thr Val Ser Asp Glu Asp Leu Glu End

3212
GCA GGC GTG GAC ACC AAT TCG GCC TTA CAA CAT CCC AAA TTG GAT CCG
```

The DNA sequence of the GLS-1 clone starts at nucleotide 1 and ends at nucleotide 348, and is therefore 348 (SEQ ID NO: 26) base pairs long. The sequence of the GLS-2 clone starts at nucleotide 283 and ends at nucleotide 1252 (SEQ ID NO: 28), and is 970 base pairs long. The sequence of the GLS-4 clone starts at nucleotide 999 and ends at nucleotide 2620 (SEQ ID NO: 30), and is 1622 base pairs long. The sequence of the GLS-3 clone starts at nucleotide 1722 and ends at nucleotide 3230, and is 1509 (SEQ ID NO: 32) base pairs long.

Example 14

Localization of Virus Neutralizing Epitopes of IBDV

A panel of three monoclonal antibodies (MCAs) generated against IBDV is used to localize antigenic determinant(s) responsible for the induction of neutralizing antibodies. Two of the MCAs, B69 and 57, were raised specifically against the Classic D78 and GLS IBDV strains respectively, and both of them neutralize only the parent IBDV strain. The second MCA, R63, was raised against the D78 IBDV strain and neutralizes all serotype I IBDVs, except for the GLS variant of the virus. All of these neutralizing antibodies bind to the VP2 (41 kDa) structural protein of IBDV in the radioimmunoprecipitation assay (unpublished data).

The MCAs thus recognize a region of epitopes located on the VP2 protein. Some sites have been found to be of importance for binding and are therefore considered associated with the epitopes. Examples are the sites corresponding to amino acids 74, 84, 213, 222, 249, 253, 254, 258, 264, 269, 270, 272, 279, 280, 284, 286, 297, 299, 305, 318, 321, 323, 326, 328, 330, 332 and 433, among others, of the VP2 protein. Information on these amino acid sites is provided in Table 12 below.

These sites are, individually or in groups, responsible for or associated with the binding of specific MCAs. Variations of the complementary DNA sequences (or viral RNAs) at the sites encoding these amino acids may provide a basis for genetic drift leading to failure of specific vaccines raised against known viral strains.

Example 15

VP2 DNA and Amino Acid Homologies and Specific Amino Acid Variations of GLS-5 and E/DEL IBDV The DNA sequences and the amino acid sequences deduced therefrom by the computerized method described above were examined, and a comparison of the GLS-5 clone and the E/DEL clone. Table 8 below shows the homology found for these US variants of the virus both at the DNA and the amino acid level.

TABLE 8

Comparison of VP2 Gene and Protein
Sequences of GLS-5 and E/DEL
Variant Viruses
Percent Homology

| | |
|---|---|
| At Nucleotide Level | 98.1% |
| Of Deduced Amino Acids | 98.0% |

Tables 9 and 10 below show variations of amino acids found between the VP2 sequences of GLS-5 and E/DEL clones.

TABLE 9

Comparison of VP2 Protein Sequences of GLS-5 and E/DEL Variant Viruses Differences in Amino Acids

| | | | | | | | | | | 9 |
|---|---|---|---|---|---|---|---|---|---|---|
| GLS-5 | (SEQ ID NO: 20) | Asp | His | Ser | Thr | Thr | Gly | Glu | Asp | Ser |
| E. DEL | (SEQ ID NO: 21) | Asn | Gln | Thr | Ala | Ile | Asp | Ala | Glu | Asn |

TABLE 10

Amino Acid Changes for IBDV VP2 Variants
AMINO ACID RESIDUE NUMBERS IN VP2

| | 94 | 213 | 222 | 249 | 253 | 254 | 269 | 270 | 280 | 284 | 286 | 318 | 321 | 323 | 326 | 330 | 443 |
|---|---|---|---|---|---|---|---|---|---|---|---|---|---|---|---|---|---|
| GLS-5 | Gln | Asp | Thr | Lys | His | Ser | Ser | Ala | Asn | Thr | Thr | Gly | Glu | Asp | Ser | Ser | Ser |
| E. Delaware | Gln | Asn | Thr | Lys | Gln | Ser | Thr | Ala | Asn | Ala | Ile | Asp | Ala | Glu | Ser | Ser | Asn |

Example 16

IBDV VP2 DNA and Amino Acid Homologies Found Between the Australian Variant and GLS and The Australian Variant and E/DEL The homologies found for the VP2 DNA of the Australian strain (002–783) and the GLS-5 viral DNA segment as well as for the Australian and E/DEL segment are shown in Table 11 below. Also shown are amino acid homologies found between the Australian and U.S. GLS-5 variants as well as between the Australian and E/DEL variants.

TABLE 11

Comparison of VP2 Gene and Protein Sequences of Australian and American Isolates of IBDV

| Percent Homology at Nucleotide Level | |
|---|---|
| GLS-5 | 91.9% |
| E. DEL | 92.1% |
| Percent Homology of Deduced Amino Acids | |
| GLS-5 | 96.2% |
| E. DEL | 95.6% |

Example 17

Changes in the Amino Acid Residues for VP2 Protein among U.S. GLS-5 and E/DEL variants, and Australian and German Cu-I IBDV Strains Comparisons of the deduced amino acid sequences between two U.S. variants, GLS-5 and E/DEL, and the Australian and the German CuI strains of IBDV showed various differences in the amino acids occupying specific positions of the VP2 protein. Changes in the amino acid residues in specific region of the VP2 protein for two U.S. variants, GLS-5 and E/DEL, the Australian strain and the German CuI strain of IBDV are shown in Table 12 below.

TABLE 12

Amino Acid Changes in VP2 of IHDV US Varients and Australian and German Viruses

| VARIANT VIRUSES | 5 | 74 | 84 | 213 | 222 | 239 | 249 | 253 | 254 | 258 | 264 | 269 | 270 | 272 | 279 |
|---|---|---|---|---|---|---|---|---|---|---|---|---|---|---|---|
| Australian | Ser | Met | Gln | Asp | Pro | Asn | Gln | Gln | Gly | Asn | Val | Thr | Thr | Thr | Gly |
| GLS-5 | Gln | Leu | Gln | Asp | Thr | Ser | Lys | His | Ser | Gly | Ile | Ser | Ala | Ile | Asn |
| E. Delaware | Gln | Leu | Gln | Asn | Thr | Ser | Lys | Gln | Ser | Gly | Ile | Thr | Ala | Ile | Asn |
| German Cu-I | Gln | Leu | Gln | Asp | Pro | Ser | Gln | His | Gly | Gly | Ile | Thr | Thr | Ile | Asn |

| VARIANT VIRUSES | 280 | 284 | 286 | 297 | 299 | 305 | 318 | 321 | 323 | 326 | 328 | 330 | 332 | 433 |
|---|---|---|---|---|---|---|---|---|---|---|---|---|---|---|
| Australian | Asn | Ala | Thr | Pro | Ser | Val | Gly | Ala | Asp | Ser | Leu | Ser | Asn | Asn |
| GLS-5 | Asn | Thr | Thr | Pro | Asn | Ile | Gly | Glu | Asp | Ser | Ser | Ser | Ser | Ser |
| E. Delaware | Asn | Ala | Ile | Pro | Asn | Ile | Asp | Ala | Glu | Ser | Ser | Ser | Ser | Asn |
| German Cu-I | Asn | Thr | Thr | Ser | Asn | Ile | Gly | Ala | Asp | Ser | Ser | Lys | Ser | Asn |

Example 18

Preparation of Synthetic Peptides

The nucleotide sequences of the genes encoding the structural protein VP2 for three IBDV strains GLS-5, E/Delaware, and German Cu-I are compared. On the basis of nucleotide sequence-predicted amino acid change(s), selected polypeptides are synthesized on an automated peptide synthesizer according to the manufacturer's instructions (Biosearch). The peptides are purified by reverse phase (C18) high performance liquid chromatography using acetonitrile gradients in 0.1% trifluoroacetic acid, and are analyzed for amino acid content in an Amino Quant analyzer (Hewlett Packard).

Synthetic peptides are dissolved in a 0.05M Tris/0.25M NaCl, pH 7.5 buffer if freely water soluble, or otherwise in a 8M urea, 1% 2-mercaptoethanol/0.05M Tris, pH 8.3, buffer, and stored at −70° C. until used.

Example 19

Competitive Antigen Binding Assays

Radiolabeling of the IBDV proteins is carried out as described (Muller, H. and Becht, H., J. Virol. 44, 384–392(1982)). Monolayers of CEF cells are infected with IBDV at a multiplicity of infection of 10 PFU/cell and incubated at 37° C. After 1 hour, the cells are washed twice and incubated for 1 hour with Eagle's minimum essential medium (MEM) without methionine. Two hours after infection the above media are removed and replaced with MEM containing 100 uCi of $^{35}$S-methionine. After a pulse with $^{35}$S-methionine for 12 hours, labeled virus particles are sedimented from the culture medium and purified further by sucrose gradient centrifugation as described above.

Competitive binding assays are performed as described by Robertson et al (Robertson, B. H. et al, virus Res. 1, 489–500, (1984)) except that purified $^{35}$S-labeled virus particle antigen is used as the assay antigen.

Briefly, MCAs are pretitrated against labeled virus to bind 70–80% of input virus in the absence of inhibitor. Synthetic peptides are added into dilution sets immediately before the assays are performed. Titration endpoints are determined at the 50% inhibition of the maximum binding ($I_{50}$ dose) by logit-log transformed linear regression analysis (Trautman, R. and Harris, W. F., Scand. J. Immunol. 6, 831–841(1977)).

The results are plotted as percent inhibition v. $\log_{10}$ molar quantity of inhibitor added.

Example 20

Some Predicted IBDV Epitopes for IBDV MCA Binding

A number of neutralizing MCAs against various strains of IBDV were used to test their reactivity with different IBDV antigenic variants. Table 13 below shows the reactivity pattern of some MCAs with different antigenic variants of IBDV in an AC-ELISA system. (Snyder, D. B., et al., Proc. 23rd Nat. Meeting Poultry Health Condemn., Ocean City, Md. (1988)).

TABLE 13

Antigenic variants of IBDV reacting with Neutralizing MCAs in AC-ELISA systems.

| IBDV VARIANT | B69 | R63 | BK44 | 179 | 8 | 42 | 57 |
|---|---|---|---|---|---|---|---|
| "Classic" | + | + | + | + | + | + | − |
| Delaware | − | + | + | + | + | − | − |
| GLS | − | − | + | + | + | + | + |

The MCAs are all neutralizing MCAs.

On the basis of the available nucleotide sequences and the corresponding deduced amino acid sequences a prediction of regions of amino acids that may be involved in the binding with these MCAs can be made. In other words, these amino acids may be part of the neutralizing epitopes of IBDV and the base pairs encoding them may be part of a special sequence (conformational epitope) minimizing the outer binding area of the protein.

Since the BK44, BK179 and BK8 MCAs react with all the IBDVs, they must recognize a region(s) of amino acids that are almost identical in all viruses. Therefore, the binding region(s) for these MCAs cannot be predicted.

However, on the basis of radioimmunoprecipitation assays it is known that all these MCAs bind to the VP2 protein of IBDV. These MCAs, thus, may recognize either a linear continuous epitope(s) or a conformational epitope(s).

Binding of the above four MCAs to VP2 amino acid residues can be predicted on the basis of the available nucleotide sequences as shown in Table 14 below.

TABLE 14

Some Predicted Epitopic Sites in The Amino Acid Sequence of IBDV

MCA B69 (SEQ ID NO: 22)

| Residue # | 314 | 315 | 316 | 317 | 318 | 319 | 320 | 321 | 322 | 323 | 324 |
|---|---|---|---|---|---|---|---|---|---|---|---|
| | Thr | Ser | Lys | Ser | Gly | Gly | Gln | Ala | Gly | Asp | Gln |

MCA 42 (SEQ ID NO: 23)

| Residue # | 279 | 280 | 281 | 282 | 283 | 284 | 285 | 286 | 287 | 288 | 289 |
|---|---|---|---|---|---|---|---|---|---|---|---|
| | Asn | Asn | Gly | Leu | Thr | Thr | Gly | Thr | Asp | Asn | Leu |

MCA R63 (SEQ ID NO: 24)

| Residue # | 264 | 265 | 266 | 267 | 268 | 269 | 270 | 271 | 272 | 273 | 274 |
|---|---|---|---|---|---|---|---|---|---|---|---|
| | Ile | Gly | Phe | Asp | Gly | Thr | Thr | Val | Ile | Thr | Arg |

MCA 57 (SEQ ID NO: 25)

| Residue # | 318 | 319 | 320 | 321 | 322 | 323 | 324 | 325 | 326 | 327 | 328 |
|---|---|---|---|---|---|---|---|---|---|---|---|
| | Gly | Gly | Gln | Glu | Gly | Asp | Gln | Met | Ser | Thy | Ser |
| | 329 | 330 | | | | | | | | | |
| | Ala | Ser | | | | | | | | | |

These sequences are, therefore, considered to be present in all types of IBDVs and DNA segments encoding them may be utilized for the vaccination of birds.

The invention now being fully described, it will be apparent to one of ordinary skill in the art that many changes and modifications can be made thereto without departing from the spirit or scope of the invention as set forth herein.

It is claimed:

1. A biologically pure RNA encoding SEQ ID NO: 19 or a fragment thereof of from 30 to 1012 amino acids long, said fragment containing SEQ ID NO: 25; or a biologically pure DNA encoding to said biologically pure RNA.

2. The biologically pure RNA of claim 1, encoding SEQ ID NO: 29, SEQ ID NO: 31, or SEQ ID NO: 34; or biologically pure DNA encoding to said biologically pure RNA.

3. The biologically pure RNA of claim 1, encoding the protein of SEQ ID NO: 19; or biologically pure DNA encoding to said biologically pure RNA.

4. The biologically pure DNA of claim 1, consisting of SEQ ID NO: 18.

5. A biologically pure DNA, encoding SEQ ID NO: 27, SEQ ID NO: 29, SEQ ID NO: 31 or SEQ ID NO: 33.

6. The biologically pure DNA of claim 5, consisting of a sequence selected from the group consisting of SEQ ID NO: 26, SEQ ID NO: 28, SEQ ID NO: 30 and SEQ ID NO: 32.

7. The biologically pure DNA of claim 5, consisting of SEQ ID NO: 28.

8. The biologically pure DNA of claim 5, consisting of SEQ ID NO: 30.

9. A recombinant vector for transfection of a gene encoding a region of the VP2 protein of the GLS strain of infectious bursal disease virus, comprising a host selected from the group consisting of baculoviruses, herpes viruses and fowl pox viruses, and the DNA of claim 8 operably incorporated in the native DNA of said host.

10. The recombinant vector of claim 9, wherein said DNA encodes SEQ ID NO: 19.

11. The recombinant vector of claim 9, wherein said DNA consists of SEQ ID NO: 18.

12. The recombinant vector of claim 9, wherein said DNA encodes SEQ ID NO: 29 or SEQ ID NO: 31.

13. The recombinant vector of claim 12, wherein said DNA consists of SEQ ID NO: 28.

14. The recombinant vector of claim 9, wherein said DNA consists of SEQ ID NO: 30.

15. A recombinant vector for transfection of a gene encoding a region of the VP2 protein of the GLS strain of infectious bursal disease virus, comprising a host selected from the group consisting of baculoviruses, herpes viruses and fowl pox viruses, and the DNA of claim 5 operably incorporated in the native DNA of said host.

16. The recombinant vector of claim 15, wherein said DNA consists of a sequence selected from the group consisting of SEQ ID NO: 26, SEQ ID NO: 28, SEQ ID NO: 30 and SEQ ID NO: 32.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
( A ) LENGTH: 15 base pairs
( B ) TYPE: nucleic acid
( C ) STRANDEDNESS: unknown
( D ) TOPOLOGY: linear ( i i ) MOLECULE TYPE: DNA (genomic)

( v i ) ORIGINAL SOURCE:
( A ) ORGANISM: Infectious bursal disease virus
( B ) STRAIN: Cu-I ( x i ) SEQUENCE DESCRIPTION: SEQ ID NO:1:

CATTGCATGG GCTAG 15

( 2 ) INFORMATION FOR SEQ ID NO:2:

( i ) SEQUENCE CHARACTERISTICS:
( A ) LENGTH: 18 base pairs
( B ) TYPE: nucleic acid
( C ) STRANDEDNESS: unknown
( D ) TOPOLOGY: linear ( i i ) MOLECULE TYPE: DNA (genomic)

( v i ) ORIGINAL SOURCE:
( A ) ORGANISM: Infectious bursal disease virus
( B ) STRAIN: Cu-I ( x i ) SEQUENCE DESCRIPTION: SEQ ID NO:2:

AACGATCCAA TTTGGGAT 18

( 2 ) INFORMATION FOR SEQ ID NO:3:

( i ) SEQUENCE CHARACTERISTICS:
( A ) LENGTH: 17 base pairs
( B ) TYPE: nucleic acid
( C ) STRANDEDNESS: unknown
( D ) TOPOLOGY: linear ( i i ) MOLECULE TYPE: DNA (genomic)

( v i ) ORIGINAL SOURCE:
( A ) ORGANISM: Infectious bursal disease virus ( x i ) SEQUENCE DESCRIPTION: SEQ ID NO:3:

TATTCTGTAA CCAGGTT 17

( 2 ) INFORMATION FOR SEQ ID NO:4:

( i ) SEQUENCE CHARACTERISTICS:
( A ) LENGTH: 18 base pairs
( B ) TYPE: nucleic acid
( C ) STRANDEDNESS: unknown
( D ) TOPOLOGY: linear

```
        ( i i ) MOLECULE TYPE: DNA (genomic)

( v i ) ORIGINAL SOURCE:
                 ( A ) ORGANISM: Infectious bursal disease virus ( x i ) SEQUENCE DESCRIPTION: SEQ ID NO:4:

CACTATCTCC  AGTTTGAT                                                                    1 8
```

( 2 ) INFORMATION FOR SEQ ID NO:5:

```
        ( i ) SEQUENCE CHARACTERISTICS:
                 ( A ) LENGTH: 20 base pairs
                 ( B ) TYPE: nucleic acid
                 ( C ) STRANDEDNESS: unknown
                 ( D ) TOPOLOGY: linear ( i i ) MOLECULE TYPE: DNA (genomic)

( v i ) ORIGINAL SOURCE:
                 ( A ) ORGANISM: Infectious bursal disease virus ( x i ) SEQUENCE DESCRIPTION: SEQ ID NO:5:

TACGAGGACT  GACGGGTCTT                                                                  2 0
```

( 2 ) INFORMATION FOR SEQ ID NO:6:

```
        ( i ) SEQUENCE CHARACTERISTICS:
                 ( A ) LENGTH: 18 base pairs
                 ( B ) TYPE: nucleic acid
                 ( C ) STRANDEDNESS: unknown
                 ( D ) TOPOLOGY: linear ( i i ) MOLECULE TYPE: DNA (genomic)

( v i ) ORIGINAL SOURCE:
                 ( A ) ORGANISM: Infectious bursal disease virus ( x i ) SEQUENCE DESCRIPTION: SEQ ID NO:6:

TTCAAAGACA  TAATCCGG                                                                    1 8
```

( 2 ) INFORMATION FOR SEQ ID NO:7:

```
        ( i ) SEQUENCE CHARACTERISTICS:
                 ( A ) LENGTH: 18 base pairs
                 ( B ) TYPE: nucleic acid
                 ( C ) STRANDEDNESS: unknown
                 ( D ) TOPOLOGY: linear ( i i ) MOLECULE TYPE: DNA (genomic)

( v i ) ORIGINAL SOURCE:
                 ( A ) ORGANISM: Infectious bursal disease virus ( x i ) SEQUENCE DESCRIPTION: SEQ ID NO:7:

GGGTGAAGCA  AGAATCCC                                                                    1 8
```

( 2 ) INFORMATION FOR SEQ ID NO:8:

```
        ( i ) SEQUENCE CHARACTERISTICS:
                 ( A ) LENGTH: 18 base pairs
                 ( B ) TYPE: nucleic acid
                 ( C ) STRANDEDNESS: unknown
                 ( D ) TOPOLOGY: linear ( i i ) MOLECULE TYPE: DNA (genomic)

( v i ) ORIGINAL SOURCE:
                 ( A ) ORGANISM: Infectious bursal disease virus ( x i ) SEQUENCE DESCRIPTION: SEQ ID NO:8:

GTGCGAGAGG  ACCTCCAA                                                                    1 8
```

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: linear ( i i ) MOLECULE TYPE: DNA (genomic)

( v i ) ORIGINAL SOURCE:
        ( A ) ORGANISM: Infectious bursal disease virus ( x i ) SEQUENCE DESCRIPTION: SEQ ID NO:9:

GTATGGAAGG TTGAGGTA                                              18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: linear ( i i ) MOLECULE TYPE: DNA (genomic)

( v i ) ORIGINAL SOURCE:
        ( A ) ORGANISM: Infectious bursal disease virus ( x i ) SEQUENCE DESCRIPTION: SEQ ID NO:10:

GGGATTCTTG CTTCACCC                                              18

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: linear ( i i ) MOLECULE TYPE: DNA (genomic)

( v i ) ORIGINAL SOURCE:
        ( A ) ORGANISM: Infectious bursal disease virus ( x i ) SEQUENCE DESCRIPTION: SEQ ID NO:11:

ACGTTCATCA AACGTTTCCC                                          20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: linear ( i i ) MOLECULE TYPE: DNA (genomic)

( v i ) ORIGINAL SOURCE:
        ( A ) ORGANISM: Infectious bursal disease virus ( x i ) SEQUENCE DESCRIPTION: SEQ ID NO:12:

TTGCAAACGC ACCACAAGCA                                          20

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: unknown (D) TOPOLOGY: linear (ii) MOLECULE TYPE: DNA (genomic)

(vi) ORIGINAL SOURCE:
    (A) ORGANISM: Infectious bursal disease virus (xi) SEQUENCE DESCRIPTION: SEQ ID NO:13:

```
CGGATCCAAT TTGGGAT                                                    17
```

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: unknown
        (D) TOPOLOGY: linear (ii) MOLECULE TYPE: DNA (genomic)

(vi) ORIGINAL SOURCE:
        (A) ORGANISM: Infectious bursal disease virus (xi) SEQUENCE DESCRIPTION: SEQ ID NO:14:

```
GTGTCGGGAG ACTCCCA                                                    17
```

(2) INFORMATION FOR SEQ ID NO:15:

(i) SEQUENCE CHARACTERISTICS:
        (A) LENGTH: 1471 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: Infectious bursal disease virus
        (B) STRAIN: Delaware (ix) FEATURE:
        (A) NAME/KEY: CDS
        (B) LOCATION: 1..15

(ix) FEATURE:
        (A) NAME/KEY: CDS
        (B) LOCATION: 19..1470

(xi) SEQUENCE DESCRIPTION: SEQ ID NO:15:

```
CTA CAA TGC TAT CAT TGA TGG TTA GTA GAG ATC AGA CAA ACG ATC GCA        48
Leu Gln Cys Tyr His     Trp Leu Val Glu Ile Arg Gln Thr Ile Ala
 1            5          1            5                      10

GCG ATG ACA AAC CTG CAA GAT CAA ACC CAA CAG ATT GTT CCG TTT ATA        96
Ala Met Thr Asn Leu Gln Asp Gln Thr Gln Gln Ile Val Pro Phe Ile
             15                  20                  25

CGG AGC CTT CTG ATG CCA ACA ACC GGA CCG GCG TCC ATT CCG GAC GAC       144
Arg Ser Leu Leu Met Pro Thr Thr Gly Pro Ala Ser Ile Pro Asp Asp
         30                  35                  40

ACC CTG GAG AAG CAC ACT CTC AGG TCA GAG ACC TCG ACC TAC AAT TTG       192
Thr Leu Glu Lys His Thr Leu Arg Ser Glu Thr Ser Thr Tyr Asn Leu
             45                  50                  55

ACT GTG GGG GAC ACA GGG TCA GGG CTA ATT GTC TTT TTC CCT GGA TTC       240
Thr Val Gly Asp Thr Gly Ser Gly Leu Ile Val Phe Phe Pro Gly Phe
         60                  65                  70

CCT GGC TCA ATT GTG GGT GCT CAC TAC ACA CTG CAG AGC AAT GGG AAC       288
Pro Gly Ser Ile Val Gly Ala His Tyr Thr Leu Gln Ser Asn Gly Asn
 75                  80                  85                  90

TAC AAG TTC GAT CAG ATG CTC CTG ACT GCC CAG AAC CTA CCG GCC AGC       336
Tyr Lys Phe Asp Gln Met Leu Leu Thr Ala Gln Asn Leu Pro Ala Ser
```

|     |     |     |     |     | 95  |     |     |     |     | 100 |     |     |     |     | 105 |     |     |      |
|-----|-----|-----|-----|-----|-----|-----|-----|-----|-----|-----|-----|-----|-----|-----|-----|-----|-----|------|
| TAC | AAC | TAC | TGG | AGG | CTA | GTG | AGT | TGG | AGT | CTC | ACA | GTA | AGG | TCA | AGC |     |     | 384  |
| Tyr | Asn | Tyr | Trp | Arg | Leu | Val | Ser | Trp | Ser | Leu | Thr | Val | Arg | Ser | Ser |     |     |      |
|     |     |     | 110 |     |     |     | 115 |     |     |     |     | 120 |     |     |     |     |     |      |
| ACA | GTC | CCT | GGT | GGC | CTT | TAT | GCA | CTA | AAC | GGC | ACC | ATA | AAC | GCG | GTG |     |     | 432  |
| Thr | Val | Pro | Gly | Gly | Leu | Tyr | Ala | Leu | Asn | Gly | Thr | Ile | Asn | Ala | Val |     |     |      |
|     |     | 125 |     |     |     |     | 130 |     |     |     |     | 135 |     |     |     |     |     |      |
| ACC | TTC | CAA | GGA | AGC | CTG | AGT | GAA | CTG | ACA | GAT | GTT | AGC | TAC | AAC | GGG |     |     | 480  |
| Thr | Phe | Gln | Gly | Ser | Leu | Ser | Glu | Leu | Thr | Asp | Val | Ser | Tyr | Asn | Gly |     |     |      |
|     | 140 |     |     |     |     | 145 |     |     |     |     | 150 |     |     |     |     |     |     |      |
| TTG | ATG | TCT | GCA | ACA | GCC | AAC | ATC | AAC | GAC | AAA | ATT | GGG | AAC | GTC | CTA |     |     | 528  |
| Leu | Met | Ser | Ala | Thr | Ala | Asn | Ile | Asn | Asp | Lys | Ile | Gly | Asn | Val | Leu |     |     |      |
| 155 |     |     |     |     | 160 |     |     |     |     | 165 |     |     |     |     | 170 |     |     |      |
| GTA | GGG | GAA | GGG | GTA | ACC | GTC | CTC | AGC | TTA | CCC | ACA | TCA | TAT | GAT | GTT |     |     | 576  |
| Val | Gly | Glu | Gly | Val | Thr | Val | Leu | Ser | Leu | Pro | Thr | Ser | Tyr | Asp | Val |     |     |      |
|     |     |     |     | 175 |     |     |     |     | 180 |     |     |     |     | 185 |     |     |     |      |
| GGG | TAT | GTG | AGG | CTT | GGT | GAC | CCC | ATA | CCC | GCT | ATA | GGG | CTT | GAC | CCA |     |     | 624  |
| Gly | Tyr | Val | Arg | Leu | Gly | Asp | Pro | Ile | Pro | Ala | Ile | Gly | Leu | Asp | Pro |     |     |      |
|     |     |     | 190 |     |     |     |     | 195 |     |     |     |     | 200 |     |     |     |     |      |
| AAA | ATG | GTA | GCA | ACA | TGT | GAC | AGC | AGT | GAC | AGG | CCC | AGA | GTC | TAC | ACC |     |     | 672  |
| Lys | Met | Val | Ala | Thr | Cys | Asp | Ser | Ser | Asp | Arg | Pro | Arg | Val | Tyr | Thr |     |     |      |
|     |     | 205 |     |     |     |     | 210 |     |     |     |     | 215 |     |     |     |     |     |      |
| ATA | ACT | GCA | GCC | GAT | AAT | TAC | CAA | TTC | TCA | TCA | CAG | TAC | CAA | ACA | GGT |     |     | 720  |
| Ile | Thr | Ala | Ala | Asp | Asn | Tyr | Gln | Phe | Ser | Ser | Gln | Tyr | Gln | Thr | Gly |     |     |      |
|     | 220 |     |     |     |     | 225 |     |     |     |     | 230 |     |     |     |     |     |     |      |
| GGG | GTA | ACA | ATC | ACA | CTG | TTC | TCA | GCC | AAC | ATT | GAT | GCC | ATC | ACA | AGT |     |     | 768  |
| Gly | Val | Thr | Ile | Thr | Leu | Phe | Ser | Ala | Asn | Ile | Asp | Ala | Ile | Thr | Ser |     |     |      |
| 235 |     |     |     |     | 240 |     |     |     |     | 245 |     |     |     |     | 250 |     |     |      |
| CTC | AGC | GTT | GGG | GGA | GAG | CTC | GTG | TTC | AAA | ACA | AGC | GTC | CAA | AGC | CTT |     |     | 816  |
| Leu | Ser | Val | Gly | Gly | Glu | Leu | Val | Phe | Lys | Thr | Ser | Val | Gln | Ser | Leu |     |     |      |
|     |     |     |     | 255 |     |     |     |     | 260 |     |     |     |     | 265 |     |     |     |      |
| GTA | CTG | GGC | GCC | ACC | ATC | TAC | CTT | ATA | GGC | TTT | GAT | GGG | ACT | GCG | GTA |     |     | 864  |
| Val | Leu | Gly | Ala | Thr | Ile | Tyr | Leu | Ile | Gly | Phe | Asp | Gly | Thr | Ala | Val |     |     |      |
|     |     |     | 270 |     |     |     |     | 275 |     |     |     |     | 280 |     |     |     |     |      |
| ATC | ACC | AGA | GCT | GTG | GCC | GCA | AAC | AAT | GGG | CTG | ACG | GCC | GGC | ATC | GAC |     |     | 912  |
| Ile | Thr | Arg | Ala | Val | Ala | Ala | Asn | Asn | Gly | Leu | Thr | Ala | Gly | Ile | Asp |     |     |      |
|     |     | 285 |     |     |     |     | 290 |     |     |     |     | 295 |     |     |     |     |     |      |
| AAT | CTT | ATG | CCA | TTC | AAT | CTT | GTG | ATT | CCA | ACC | AAT | GAG | ATA | ACC | CAG |     |     | 960  |
| Asn | Leu | Met | Pro | Phe | Asn | Leu | Val | Ile | Pro | Thr | Asn | Glu | Ile | Thr | Gln |     |     |      |
|     | 300 |     |     |     |     | 305 |     |     |     |     | 310 |     |     |     |     |     |     |      |
| CCA | ATC | ACA | TCC | ATC | AAA | CTG | GAG | ATA | GTG | ACC | TCC | AAA | AGT | GAT | GGT |     |     | 1008 |
| Pro | Ile | Thr | Ser | Ile | Lys | Leu | Glu | Ile | Val | Thr | Ser | Lys | Ser | Asp | Gly |     |     |      |
| 315 |     |     |     |     | 320 |     |     |     |     | 325 |     |     |     |     | 330 |     |     |      |
| CAG | GCA | GGG | GAA | CAG | ATG | TCA | TGG | TCG | GCA | AGT | GGG | AGC | CTA | GCA | GTG |     |     | 1056 |
| Gln | Ala | Gly | Glu | Gln | Met | Ser | Trp | Ser | Ala | Ser | Gly | Ser | Leu | Ala | Val |     |     |      |
|     |     |     |     | 335 |     |     |     |     | 340 |     |     |     |     | 345 |     |     |     |      |
| ACG | ATC | CAT | GGT | GGC | AAC | TAT | CCA | GGA | GCC | CTC | CGT | CCC | GTC | ACA | CTA |     |     | 1104 |
| Thr | Ile | His | Gly | Gly | Asn | Tyr | Pro | Gly | Ala | Leu | Arg | Pro | Val | Thr | Leu |     |     |      |
|     |     |     | 350 |     |     |     |     | 355 |     |     |     |     | 360 |     |     |     |     |      |
| GTG | GCC | TAC | GAA | AGA | GTG | GCA | ACA | GGA | TCT | GTC | GTT | ACG | GTC | GCT | GGG |     |     | 1152 |
| Val | Ala | Tyr | Glu | Arg | Val | Ala | Thr | Gly | Ser | Val | Val | Thr | Val | Ala | Gly |     |     |      |
|     |     | 365 |     |     |     |     | 370 |     |     |     |     | 375 |     |     |     |     |     |      |
| GTG | AGC | AAC | TTC | GAG | CTG | ATC | CCA | AAT | CCT | GAA | CTA | GCA | AAG | AAC | CTG |     |     | 1200 |
| Val | Ser | Asn | Phe | Glu | Leu | Ile | Pro | Asn | Pro | Glu | Leu | Ala | Lys | Asn | Leu |     |     |      |
|     | 380 |     |     |     |     | 385 |     |     |     |     | 390 |     |     |     |     |     |     |      |
| GTT | ACA | GAA | TAT | GGC | CGA | TTT | GAC | CCA | GGA | GCC | ATG | AAC | TAC | ACG | AAA |     |     | 1248 |
| Val | Thr | Glu | Tyr | Gly | Arg | Phe | Asp | Pro | Gly | Ala | Met | Asn | Tyr | Thr | Lys |     |     |      |
| 395 |     |     |     |     | 400 |     |     |     |     | 405 |     |     |     |     | 410 |     |     |      |
| TTG | ATA | CTG | AGT | GAG | AGG | GAC | CGC | CTT | GGC | ATC | AAG | ACC | GTC | TGG | CCA |     |     | 1296 |
| Leu | Ile | Leu | Ser | Glu | Arg | Asp | Arg | Leu | Gly | Ile | Lys | Thr | Val | Trp | Pro |     |     |      |

|     |     |     |     | 415 |     |     |     |     | 420 |     |     |     |     | 425 |     |     |      |
|-----|-----|-----|-----|-----|-----|-----|-----|-----|-----|-----|-----|-----|-----|-----|-----|-----|------|
| ACA | AGG | GAG | TAC | ACT | GAC | TTT | CGT | GAG | TAC | TTC | ATG | GAG | GTG | GCC | GAC |     | 1344 |
| Thr | Arg | Glu | Tyr | Thr | Asp | Phe | Arg | Glu | Tyr | Phe | Met | Glu | Val | Ala | Asp |     |      |
|     |     |     | 430 |     |     |     |     | 435 |     |     |     |     | 440 |     |     |     |      |
| CTC | AAC | TCT | CCC | CTG | AAG | ATT | GCA | GGA | GCA | TTT | GGC | TTC | AAA | GAC | ATA |     | 1392 |
| Leu | Asn | Ser | Pro | Leu | Lys | Ile | Ala | Gly | Ala | Phe | Gly | Phe | Lys | Asp | Ile |     |      |
|     |     | 445 |     |     |     |     | 450 |     |     |     |     | 455 |     |     |     |     |      |
| ATC | CGG | GCC | ATA | AGG | AGG | ATA | GCT | GTA | CCG | GTG | GTC | TCT | ACA | TTG | TTC |     | 1440 |
| Ile | Arg | Ala | Ile | Arg | Arg | Ile | Ala | Val | Pro | Val | Val | Ser | Thr | Leu | Phe |     |      |
|     | 460 |     |     |     |     | 465 |     |     |     |     | 470 |     |     |     |     |     |      |
| CCA | CCT | GCC | GCT | CCT | GTA | GCC | CAT | GCA | ATT | G   |     |     |     |     |     |     | 1471 |
| Pro | Pro | Ala | Ala | Pro | Val | Ala | His | Ala | Ile |     |     |     |     |     |     |     |      |
| 475 |     |     |     |     | 480 |     |     |     |     |     |     |     |     |     |     |     |      |

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

Leu Gln Cys Tyr His
 1               5

( 2 ) INFORMATION FOR SEQ ID NO:17:

( i ) SEQUENCE CHARACTERISTICS:
        ( A ) LENGTH: 484 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| Trp | Leu | Val | Glu | Ile | Arg | Gln | Thr | Ile | Ala | Ala | Met | Thr | Asn | Leu | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Gln | Thr | Gln | Gln | Ile | Val | Pro | Phe | Ile | Arg | Ser | Leu | Leu | Met | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Thr | Gly | Pro | Ala | Ser | Ile | Pro | Asp | Asp | Thr | Leu | Glu | Lys | His | Thr |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Leu | Arg | Ser | Glu | Thr | Ser | Thr | Tyr | Asn | Leu | Thr | Val | Gly | Asp | Thr | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Gly | Leu | Ile | Val | Phe | Phe | Pro | Gly | Phe | Pro | Gly | Ser | Ile | Val | Gly |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | His | Tyr | Thr | Leu | Gln | Ser | Asn | Gly | Asn | Tyr | Lys | Phe | Asp | Gln | Met |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Leu | Thr | Ala | Gln | Asn | Leu | Pro | Ala | Ser | Tyr | Asn | Tyr | Trp | Arg | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Val | Ser | Trp | Ser | Leu | Thr | Val | Arg | Ser | Ser | Thr | Val | Pro | Gly | Gly | Leu |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Tyr | Ala | Leu | Asn | Gly | Thr | Ile | Asn | Ala | Val | Thr | Phe | Gln | Gly | Ser | Leu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ser | Glu | Leu | Thr | Asp | Val | Ser | Tyr | Asn | Gly | Leu | Met | Ser | Ala | Thr | Ala |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Asn | Ile | Asn | Asp | Lys | Ile | Gly | Asn | Val | Leu | Val | Gly | Glu | Gly | Val | Thr |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Val | Leu | Ser | Leu | Pro | Thr | Ser | Tyr | Asp | Val | Gly | Tyr | Val | Arg | Leu | Gly |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

Asp Pro Ile Pro Ala Ile Gly Leu Asp Pro Lys Met Val Ala Thr Cys
    195             200             205
Asp Ser Ser Asp Arg Pro Arg Val Tyr Thr Ile Thr Ala Ala Asp Asn
    210             215             220
Tyr Gln Phe Ser Ser Gln Tyr Gln Thr Gly Gly Val Thr Ile Thr Leu
225             230             235             240
Phe Ser Ala Asn Ile Asp Ala Ile Thr Ser Leu Ser Val Gly Gly Glu
            245             250             255
Leu Val Phe Lys Thr Ser Val Gln Ser Leu Val Leu Gly Ala Thr Ile
        260             265             270
Tyr Leu Ile Gly Phe Asp Gly Thr Ala Val Ile Thr Arg Ala Val Ala
    275             280             285
Ala Asn Asn Gly Leu Thr Ala Gly Ile Asp Asn Leu Met Pro Phe Asn
    290             295             300
Leu Val Ile Pro Thr Asn Glu Ile Thr Gln Pro Ile Thr Ser Ile Lys
305             310             315             320
Leu Glu Ile Val Thr Ser Lys Ser Asp Gly Gln Ala Gly Glu Gln Met
            325             330             335
Ser Trp Ser Ala Ser Gly Ser Leu Ala Val Thr Ile His Gly Gly Asn
        340             345             350
Tyr Pro Gly Ala Leu Arg Pro Val Thr Leu Val Ala Tyr Glu Arg Val
    355             360             365
Ala Thr Gly Ser Val Val Thr Val Ala Gly Val Ser Asn Phe Glu Leu
    370             375             380
Ile Pro Asn Pro Glu Leu Ala Lys Asn Leu Val Thr Glu Tyr Gly Arg
385             390             395             400
Phe Asp Pro Gly Ala Met Asn Tyr Thr Lys Leu Ile Leu Ser Glu Arg
            405             410             415
Asp Arg Leu Gly Ile Lys Thr Val Trp Pro Thr Arg Glu Tyr Thr Asp
        420             425             430
Phe Arg Glu Tyr Phe Met Glu Val Ala Asp Leu Asn Ser Pro Leu Lys
    435             440             445
Ile Ala Gly Ala Phe Gly Phe Lys Asp Ile Ile Arg Ala Ile Arg Arg
    450             455             460
Ile Ala Val Pro Val Val Ser Thr Leu Phe Pro Pro Ala Ala Pro Val
465             470             475             480
Ala His Ala Ile ( 2 ) INFORMATION FOR SEQ ID NO:18:

( i ) SEQUENCE CHARACTERISTICS:
        ( A ) LENGTH: 3230 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: Infectious bursal disease virus
        ( B ) STRAIN: GLS ( i x ) FEATURE:
        ( A ) NAME/KEY: CDS
        ( B ) LOCATION: 114..3149

( x i ) SEQUENCE DESCRIPTION: SEQ ID NO:18:

CCCCGGGGGA GTCACCCGGG GACAGGCCGT CAAGGCCTTG TTCCAGGATG GAACTCCCCC   60

-continued

| | | | | | | | | | | | | | | | | |
|---|---|---|---|---|---|---|---|---|---|---|---|---|---|---|---|---|
| TTCTACAATG | CTATCATTGA | TGGTTAGTAG | AGATCGGACA | AACGATCGCA | GCG | ATG | | | | | | | | | | 116 |
| | | | | | | Met 1 | | | | | | | | | | |
| ACA | AAC | CTG | CAA | GAT | CAA | ACC | CAA | CAG | ATT | GTT | CCG | TTC | ATA | CGG | AGC | 164 |
| Thr | Asn | Leu | Gln 5 | Asp | Gln | Thr | Gln | Gln 10 | Ile | Val | Pro | Phe | Ile 15 | Arg | Ser | |
| CTT | CTG | ATG | CCA | ACA | ACC | GGA | CCG | GCG | TCC | ATT | CCG | GAC | GAC | ACC | CTG | 212 |
| Leu | Leu | Met 20 | Pro | Thr | Thr | Gly | Pro 25 | Ala | Ser | Ile | Pro | Asp 30 | Asp | Thr | Leu | |
| GAG | AAG | CAC | ACT | CTC | AGG | TCA | GAG | ACC | TCG | ACC | TAC | AAT | TTG | ACT | GTG | 260 |
| Glu | Lys 35 | His | Thr | Leu | Arg | Ser 40 | Glu | Thr | Ser | Thr | Tyr 45 | Asn | Leu | Thr | Val | |
| GGG | GAC | ACA | GGG | TCA | GGG | CTA | ATT | GTC | TTT | TTC | CCT | GGA | TTC | CCT | GGC | 308 |
| Gly 50 | Asp | Thr | Gly | Ser | Gly 55 | Leu | Ile | Val | Phe | Phe 60 | Pro | Gly | Phe | Pro | Gly 65 | |
| TCA | ATT | GTG | GGT | GCT | CAC | TAC | ACA | CTG | CAG | AGC | AAT | GGG | AAC | TAC | AAG | 356 |
| Ser | Ile | Val | Gly | Ala 70 | His | Tyr | Thr | Leu | Gln 75 | Ser | Asn | Gly | Asn | Tyr 80 | Lys | |
| TTC | GAT | CAG | ATG | CTC | CTG | ACT | GCC | CAG | AAC | CTA | CCG | CCC | AGC | TAC | AAC | 404 |
| Phe | Asp | Gln | Met 85 | Leu | Leu | Thr | Ala | Gln 90 | Asn | Leu | Pro | Pro | Ser 95 | Tyr | Asn | |
| TAC | TGC | AGG | CTA | GTG | AGT | CGG | AGT | CTC | ACA | GTA | AGG | TCA | AGC | ACA | CTC | 452 |
| Tyr | Cys | Arg 100 | Leu | Val | Ser | Arg | Ser 105 | Leu | Thr | Val | Arg | Ser 110 | Ser | Thr | Leu | |
| CCT | GGT | GGC | GTT | TAT | GCA | CTA | AAC | GGC | ACC | ATA | AAC | GCC | GTG | ACC | TTC | 500 |
| Pro | Gly | Gly | Val | Tyr 115 | Ala | Leu | Asn | Gly | Thr 120 | Ile | Asn | Ala | Val | Thr 125 | Phe | |
| CAA | GGA | AGC | CTG | AGT | GAA | CTG | ACA | GAT | GTT | AGC | TAC | AAT | GGG | TTG | ATG | 548 |
| Gln | Gly | Ser | Leu 130 | Ser | Glu | Leu | Thr | Asp 135 | Val | Ser | Tyr | Asn | Gly 140 | Leu | Met 145 | |
| TCT | GCA | ACA | GCC | AAC | ATG | AAC | GAC | AAA | ATT | GGG | AAC | GTC | CTA | GTA | GGG | 596 |
| Ser | Ala | Thr | Ala | Asn 150 | Met | Asn | Asp | Lys | Ile 155 | Gly | Asn | Val | Leu | Val 160 | Gly | |
| GAA | GGG | GTT | ACT | GTC | CTC | AGC | TTA | CCC | ACA | TCA | TAT | GAT | CTT | GGG | TAT | 644 |
| Glu | Gly | Val | Thr 165 | Val | Leu | Ser | Leu | Pro 170 | Thr | Ser | Tyr | Asp | Leu 175 | Gly | Tyr | |
| GTG | AGG | CTT | GGT | GAC | CCC | ATA | CCC | GCT | ATA | GGG | CTT | GAC | CCA | AAA | ATG | 692 |
| Val | Arg | Leu 180 | Gly | Asp | Pro | Ile | Pro 185 | Ala | Ile | Gly | Leu | Asp 190 | Pro | Lys | Met | |
| GTA | GCA | ACA | TGT | GAC | AGC | AGT | GAC | AGG | CCC | AGA | GTC | TAC | ACC | ATA | ACT | 740 |
| Val | Ala | Thr | Cys 195 | Asp | Ser | Ser | Asp | Arg 200 | Pro | Arg | Val | Tyr | Thr 205 | Ile | Thr | |
| GCA | GCT | GAT | GAT | TAC | CAA | TTC | TCA | TCA | CAG | TAC | CAA | ACA | GGT | GGG | GTA | 788 |
| Ala | Ala | Asp 210 | Asp | Tyr | Gln | Phe | Ser 215 | Ser | Gln | Tyr | Gln | Thr 220 | Gly | Gly | Val 225 | |
| ACA | ATC | ACC | CTG | TTC | TCA | GCC | AAC | ATT | GAT | GCC | ATC | ACA | AGC | CTC | AGC | 836 |
| Thr | Ile | Thr | Leu | Phe 230 | Ser | Ala | Asn | Ile | Asp 235 | Ala | Ile | Thr | Ser | Leu 240 | Ser | |
| GTT | GGG | GGA | GAG | CTC | GTG | TTT | AAA | ACA | AGC | GTC | CAC | AGC | CTT | GTA | CTG | 884 |
| Val | Gly | Gly | Glu 245 | Leu | Val | Phe | Lys | Thr 250 | Ser | Val | His | Ser | Leu 255 | Val | Leu | |
| GGC | GCC | ACC | ATC | TAC | CTT | ATA | GGC | TTT | GAT | GGG | TCT | GCG | GTA | ATC | ACT | 932 |
| Gly | Ala | Thr 260 | Ile | Tyr | Leu | Ile | Gly 265 | Phe | Asp | Gly | Ser | Ala 270 | Val | Ile | Thr | |
| AGA | GCT | GTG | GCC | GCA | AAC | AAT | GGG | CTG | ACG | ACC | GGC | ACC | GAC | AAT | CTT | 980 |
| Arg | Ala | Val 275 | Ala | Ala | Asn | Asn | Gly 280 | Leu | Thr | Thr | Gly | Thr 285 | Asp | Asn | Leu | |
| ATG | CCA | TTC | AAT | CTT | GTG | ATT | CCA | ACC | AAC | GAG | ATA | ACC | CAG | CCA | ATC | 1028 |
| Met | Pro | Phe | Asn 290 | Leu | Val | Ile | Pro | Thr 295 | Asn | Glu | Ile | Thr 300 | Gln | Pro | Ile 305 | |

| | |
|---|---|
| ACA Thr  TCC Ser  ATC Ile  AAA Lys  CTG Leu 310  GAG Glu  ATA Ile  GTG Val  ACC Thr  TCC Ser 315  AAA Lys  AGT Ser  GGT Gly  GGT Gly  CAG Gln 320  GAA Glu | 1076 |
| GGG Gly  GAC Asp  CAG Gln  ATG Met 325  TCA Ser  TGG Trp  TCG Ser  GCA Ala  AGT Ser 330  GGG Gly  AGC Ser  CTA Leu  GCA Ala  GTG Val 335  ACG Thr  ATT Ile | 1124 |
| CAT His  GGT Gly  GGC Gly  AAC Asn 340  TAT Tyr  CCA Pro  GGG Gly  GCC Ala  CTC Leu 345  CGT Arg  CCC Pro  GTC Val  ACA Thr  CTA Leu 350  GTA Val  GCC Ala | 1172 |
| TAC Tyr  GAA Glu  AGA Arg 355  GTG Val  GCA Ala  ACA Thr  GGA Gly  TCT Ser 360  GTC Val  GTT Val  ACG Thr  GTC Val  GCT Ala 365  GGG Gly  GTG Val  AGC Ser | 1220 |
| AAC Asn 370  TTC Phe  GAG Glu  CTG Leu  ATC Ile  CCA Pro 375  AAT Asn  CCT Pro  GAA Glu  CTA Leu  GCA Ala 380  AAG Lys  AAC Asn  CTG Leu  GTT Val  ACA Thr 385 | 1268 |
| GAA Glu  TAC Tyr  GGC Gly  CGA Arg  TTT Phe 390  GAC Asp  CCA Pro  GGA Gly  GCC Ala  ATG Met 395  AAC Asn  TAC Tyr  ACA Thr  AAA Lys  TTG Leu 400  ATA Ile | 1316 |
| CTG Leu  AGT Ser  GAG Glu  AGG Arg 405  GAC Asp  CGC Arg  CTT Leu  GGC Gly  ATC Ile 410  AAG Lys  ACA Thr  GTC Val  TGG Trp  CCG Pro 415  ACA Thr  AGG Arg | 1364 |
| GAG Glu  TAC Tyr  ACC Thr 420  GAC Asp  TTT Phe  CGT Arg  GAG Glu  TAC Tyr 425  TTC Phe  ATG Met  GAG Glu  GTG Val  GCC Ala 430  GAC Asp  CTC Leu  AGC Ser | 1412 |
| TCT Ser  CCC Pro 435  CTG Leu  AAG Lys  ATT Ile  GCA Ala  GGA Gly 440  GCA Ala  TTT Phe  GGC Gly  TTC Phe  AAA Lys 445  GAC Asp  ATA Ile  ATC Ile  CGG Arg | 1460 |
| GCC Ala 450  ATA Ile  AGG Arg  AGG Arg  ATA Ile  GCT Ala 455  GTG Val  CCG Pro  GTG Val  GTC Val  TCC Ser 460  ACA Thr  TTG Leu  TTC Phe  CCA Pro  CCT Pro 465 | 1508 |
| GCC Ala  GCT Ala  CCC Pro  CTG Leu  GCC Ala 470  CAT His  GCA Ala  ATT Ile  GGG Gly  GAA Glu 475  GGT Gly  GTA Val  GAC Asp  TAC Tyr  CTG Leu 480  CTG Leu | 1556 |
| GGT Gly  GAT Asp  GAG Glu  GCA Ala  CAG Gln 485  GCT Ala  GCT Ala  TCA Ser  GGA Gly  ACT Thr 490  GCT Ala  CGA Arg  GCC Ala  GCG Ala  TCA Ser 495  GGA Gly | 1604 |
| AAA Lys  GCA Ala  AGG Arg  GCT Ala 500  GCC Ala  TCA Ser  GGC Gly  CGC Arg  ATA Ile 505  AGG Arg  CAG Gln  CTG Leu  ACT Thr  CTC Leu 510  GCC Ala  GCC Ala | 1652 |
| GAC Asp  AAG Lys  GGG Gly  TAC Tyr  GAG Glu 515  GTA Val  GTC Val  GCG Ala  AAT Asn  CTA Leu 520  TTC Phe  CAG Gln  GTG Val  CCC Pro  CAG Gln 525  AAT Asn | 1700 |
| CCC Pro 530  GTA Val  GTC Val  GAC Asp  GGG Gly  ATT Ile 535  CTT Leu  GCT Ala  TCA Ser  CCC Pro  GGG Gly 540  ATA Ile  CTC Leu  CGC Arg  GGT Gly  GCA Ala 545 | 1748 |
| CAC His  AAC Asn  CTC Leu  GAC Asp  TGC Cys 550  GTG Val  TTA Leu  AGA Arg  GAG Glu  GGC Gly 555  GCC Ala  ACG Thr  CTA Leu  TTC Phe  CCT Pro 560  GTG Val | 1796 |
| GTC Val  ATC Ile  ACG Thr  ACA Thr 565  GTG Val  GAA Glu  GAC Asp  GCC Ala  ATG Met 570  ACA Thr  CCC Pro  AAA Lys  GCA Ala  CTA Leu 575  AAC Asn  AGC Ser | 1844 |
| AAA Lys  ATG Met  TTT Phe  GCT Ala 580  GTC Val  ATT Ile  GAA Glu  GGC Gly  GTG Val 585  CGA Arg  GAG Glu  GAC Asp  CTC Leu  CAA Gln 590  CCT Pro  CCA Pro | 1892 |
| TCT Ser  CAA Gln  AGA Arg  GGA Gly 595  TCC Ser  TTC Phe  ATA Ile  CGA Arg  ACT Thr 600  CTC Leu  TCC Ser  GGA Gly  CAC His  AGA Arg 605  GTC Val  TAT Tyr | 1940 |
| GGA Gly  TAT Tyr 610  GCT Ala  CCA Pro  GAT Asp  GGG Gly  GTA Val 615  CTT Leu  CCA Pro  CTG Leu  GAG Glu  ACT Thr 620  GGG Gly  AGA Arg  GAC Asp  TAC Tyr 625 | 1988 |

| | | | | | | | | | | | | | | | | |
|---|---|---|---|---|---|---|---|---|---|---|---|---|---|---|---|---|
| ACC | GTT | GTC | CCA | ATA | GAT | GAT | GTC | TGG | GAC | GAC | AGC | ATT | ATG | CTG | TCC | 2036 |
| Thr | Val | Val | Pro | Ile | Asp | Asp | Val | Trp | Asp | Asp | Ser | Ile | Met | Leu | Ser | |
| | | | | 630 | | | | 635 | | | | | | 640 | | |
| AAA | GAC | CCC | ATA | CCT | CCT | ATT | GTG | GGA | AAC | AGT | GGA | AAC | CTA | GCC | ATA | 2084 |
| Lys | Asp | Pro | Ile | Pro | Pro | Ile | Val | Gly | Asn | Ser | Gly | Asn | Leu | Ala | Ile | |
| | | | 645 | | | | 650 | | | | | 655 | | | | |
| GCT | TAC | ATG | GAT | GTG | TTT | CGA | CCC | AAA | GTC | CCC | ATC | CAT | GTG | GCC | ATG | 2132 |
| Ala | Tyr | Met | Asp | Val | Phe | Arg | Pro | Lys | Val | Pro | Ile | His | Val | Ala | Met | |
| | | 660 | | | | | 665 | | | | | 670 | | | | |
| ACG | GGA | GCC | CTC | AAC | GCT | TGT | GGC | GAG | ATT | GAG | AAA | ATA | AGC | TTT | AGA | 2180 |
| Thr | Gly | Ala | Leu | Asn | Ala | Cys | Gly | Glu | Ile | Glu | Lys | Ile | Ser | Phe | Arg | |
| | 675 | | | | | 680 | | | | | 685 | | | | | |
| AGC | ACC | AAG | CTC | GCC | ACC | GCA | CAC | CGG | CTT | GGC | CTC | AAG | TTG | GCT | GGT | 2228 |
| Ser | Thr | Lys | Leu | Ala | Thr | Ala | His | Arg | Leu | Gly | Leu | Lys | Leu | Ala | Gly | |
| 690 | | | | | 695 | | | | | 700 | | | | | 705 | |
| CCC | GGA | GCA | TTT | GAT | GTA | AAC | ACC | GGG | CCC | AAC | TGG | GCA | ACG | TTC | ATC | 2276 |
| Pro | Gly | Ala | Phe | Asp | Val | Asn | Thr | Gly | Pro | Asn | Trp | Ala | Thr | Phe | Ile | |
| | | | | 710 | | | | | 715 | | | | | 720 | | |
| AAA | CGT | TTC | CCT | CAC | AAT | CCA | CGC | GAC | TGG | GAC | AGG | CTC | CCC | TAC | CTC | 2324 |
| Lys | Arg | Phe | Pro | His | Asn | Pro | Arg | Asp | Trp | Asp | Arg | Leu | Pro | Tyr | Leu | |
| | | | 725 | | | | | 730 | | | | | 735 | | | |
| AAC | CTT | CCA | TAC | CTT | CCA | CCC | AAT | GCA | GGA | CGC | CAG | TAC | CAC | CTC | GCC | 2372 |
| Asn | Leu | Pro | Tyr | Leu | Pro | Pro | Asn | Ala | Gly | Arg | Gln | Tyr | His | Leu | Ala | |
| | | 740 | | | | | 745 | | | | | 750 | | | | |
| ATG | GCC | GCA | TCA | GAG | TTC | AAG | GAG | ACC | CCT | GAA | CTC | GAG | AGC | GCC | GTC | 2420 |
| Met | Ala | Ala | Ser | Glu | Phe | Lys | Glu | Thr | Pro | Glu | Leu | Glu | Ser | Ala | Val | |
| | 755 | | | | | 760 | | | | | 765 | | | | | |
| AGG | GCC | ATG | GAA | GCA | GCA | GCC | AGT | GTA | GAC | CCA | CTG | TTC | CAA | TCT | GCA | 2468 |
| Arg | Ala | Met | Glu | Ala | Ala | Ala | Ser | Val | Asp | Pro | Leu | Phe | Gln | Ser | Ala | |
| 770 | | | | | 775 | | | | | 780 | | | | | 785 | |
| CTC | AGT | GTG | TTC | ATG | TGG | CTG | GAA | GAG | AAT | GGG | ATT | GTG | ACT | GAC | ATG | 2516 |
| Leu | Ser | Val | Phe | Met | Trp | Leu | Glu | Glu | Asn | Gly | Ile | Val | Thr | Asp | Met | |
| | | | | 790 | | | | | 795 | | | | | 800 | | |
| GCC | AAC | TTC | GCA | CTC | AGC | GAC | CCG | AAC | GCC | CAT | CGG | ATG | CGA | AAC | TTT | 2564 |
| Ala | Asn | Phe | Ala | Leu | Ser | Asp | Pro | Asn | Ala | His | Arg | Met | Arg | Asn | Phe | |
| | | | 805 | | | | | 810 | | | | | 815 | | | |
| CTT | GCA | AAC | GCA | CCA | CAA | GCA | GGT | AGC | AAG | TCT | CAA | AGG | GCC | AAA | TAC | 2612 |
| Leu | Ala | Asn | Ala | Pro | Gln | Ala | Gly | Ser | Lys | Ser | Gln | Arg | Ala | Lys | Tyr | |
| | | 820 | | | | | 825 | | | | | 830 | | | | |
| GGG | ACA | GCA | GGC | TAC | GGA | GTG | GAG | GCC | CGG | GGC | CCC | ACA | CCA | GAA | GAA | 2660 |
| Gly | Thr | Ala | Gly | Tyr | Gly | Val | Glu | Ala | Arg | Gly | Pro | Thr | Pro | Glu | Glu | |
| | 835 | | | | | 840 | | | | | 845 | | | | | |
| GCA | CAG | AGG | GAA | AAA | GAC | ACA | CGG | ATC | TCA | AAG | AAG | ATG | GAG | ACC | ATG | 2708 |
| Ala | Gln | Arg | Glu | Lys | Asp | Thr | Arg | Ile | Ser | Lys | Lys | Met | Glu | Thr | Met | |
| 850 | | | | | 855 | | | | | 860 | | | | | 865 | |
| GGC | ATC | TAC | TTT | GCA | ACA | CCA | GAA | TGG | GTA | GCA | CTC | AAT | GGG | CAC | CGA | 2756 |
| Gly | Ile | Tyr | Phe | Ala | Thr | Pro | Glu | Trp | Val | Ala | Leu | Asn | Gly | His | Arg | |
| | | | | 870 | | | | | 875 | | | | | 880 | | |
| GGG | CCA | AGC | CCC | GGC | CAG | CTA | AAG | TAC | TGG | CAG | AAC | ACA | CGA | GAA | ATA | 2804 |
| Gly | Pro | Ser | Pro | Gly | Gln | Leu | Lys | Tyr | Trp | Gln | Asn | Thr | Arg | Glu | Ile | |
| | | | 885 | | | | | 890 | | | | | 895 | | | |
| CCG | GAC | CCA | AAC | GAG | GAC | TAT | CTA | GAC | TAC | GTG | CAT | GCA | GAG | AAG | AGC | 2852 |
| Pro | Asp | Pro | Asn | Glu | Asp | Tyr | Leu | Asp | Tyr | Val | His | Ala | Glu | Lys | Ser | |
| | | 900 | | | | | 905 | | | | | 910 | | | | |
| CGG | TTG | GCA | TCA | GAA | GAA | CAA | ATC | CTA | AGG | GCA | GCT | ACG | TCG | ATC | TAC | 2900 |
| Arg | Leu | Ala | Ser | Glu | Glu | Gln | Ile | Leu | Arg | Ala | Ala | Thr | Ser | Ile | Tyr | |
| | 915 | | | | | 920 | | | | | 925 | | | | | |
| GGG | GCT | CCA | GGA | CAG | GCA | GAG | CCA | CCC | CAA | GCT | TTC | ATA | GAC | GAA | GTT | 2948 |
| Gly | Ala | Pro | Gly | Gln | Ala | Glu | Pro | Pro | Gln | Ala | Phe | Ile | Asp | Glu | Val | |
| 930 | | | | | 935 | | | | | 940 | | | | | 945 | |

| | | | | | | | | | | | | | | | | |
|---|---|---|---|---|---|---|---|---|---|---|---|---|---|---|---|---|
| GCC | AAA | GTC | TAT | GAA | ATC | AAC | CAT | GGA | CGT | GGC | CCA | AAC | CAA | GAA | CAG | 2996 |
| Ala | Lys | Val | Tyr | Glu | Ile | Asn | His | Gly | Arg | Gly | Pro | Asn | Gln | Glu | Gln | |
| | | | 950 | | | | | 955 | | | | | 960 | | | |
| ATG | AAA | GAT | CTG | CTC | TTG | ACT | GCG | ATG | GAG | ATG | AAG | CAT | CGC | AAT | CCC | 3044 |
| Met | Lys | Asp | Leu | Leu | Leu | Thr | Ala | Met | Glu | Met | Lys | His | Arg | Asn | Pro | |
| | | | 965 | | | | | 970 | | | | | 975 | | | |
| AGG | CGG | GCT | CCA | CCA | AAG | CCC | AAG | CCA | AGA | CCC | AAC | GCT | CCA | ACG | CAG | 3092 |
| Arg | Arg | Ala | Pro | Pro | Lys | Pro | Lys | Pro | Arg | Pro | Asn | Ala | Pro | Thr | Gln | |
| | | 980 | | | | | 985 | | | | | 990 | | | | |
| AGA | CCC | CCT | GGT | CGG | CTG | GGC | CGC | TGG | ATC | AGG | ACT | GTC | TCT | GAT | GAG | 3140 |
| Arg | Pro | Pro | Gly | Arg | Leu | Gly | Arg | Trp | Ile | Arg | Thr | Val | Ser | Asp | Glu | |
| | 995 | | | | | 1000 | | | | | 1005 | | | | | |
| GAC | CTT | GAG | TGAGGCTCCT | GGGAGTCTCC | CGACACCACC | CGCGCAGGCG | | | | | | | | | | 3189 |
| Asp | Leu | Glu | | | | | | | | | | | | | | |
| 1010 | | | | | | | | | | | | | | | | |

TGGACACCAA TTCGGCCTTA CAACATCCCA AATTGGATCC G         3230

( 2 ) INFORMATION FOR SEQ ID NO:19:

( i ) SEQUENCE CHARACTERISTICS:
        ( A ) LENGTH: 1012 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met Thr Asn Leu Gln Asp Gln Thr Gln Gln Ile Val Pro Phe Ile Arg
 1               5                  10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Pro Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Met Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val His Ser Leu Val
```

|     |     |     |     |     |     | 245 |     |     |     |     | 250 |     |     |     |     | 255 |     |
|---|---|---|---|---|---|---|---|---|---|---|---|---|---|---|---|---|---|

```
Leu  Gly  Ala  Thr  Ile  Tyr  Leu  Ile  Gly  Phe  Asp  Gly  Ser  Ala  Val  Ile
               260                      265                      270
Thr  Arg  Ala  Val  Ala  Ala  Asn  Asn  Gly  Leu  Thr  Thr  Gly  Thr  Asp  Asn
               275                 280                      285
Leu  Met  Pro  Phe  Asn  Leu  Val  Ile  Pro  Thr  Asn  Glu  Ile  Thr  Gln  Pro
          290                 295                 300
Ile  Thr  Ser  Ile  Lys  Leu  Glu  Ile  Val  Thr  Ser  Lys  Ser  Gly  Gly  Gln
305                      310                      315                      320
Glu  Gly  Asp  Gln  Met  Ser  Trp  Ser  Ala  Ser  Gly  Ser  Leu  Ala  Val  Thr
               325                      330                      335
Ile  His  Gly  Gly  Asn  Tyr  Pro  Gly  Ala  Leu  Arg  Pro  Val  Thr  Leu  Val
               340                 345                      350
Ala  Tyr  Glu  Arg  Val  Ala  Thr  Gly  Ser  Val  Val  Thr  Val  Ala  Gly  Val
               355                      360                      365
Ser  Asn  Phe  Glu  Leu  Ile  Pro  Asn  Pro  Glu  Leu  Ala  Lys  Asn  Leu  Val
     370                      375                      380
Thr  Glu  Tyr  Gly  Arg  Phe  Asp  Pro  Gly  Ala  Met  Asn  Tyr  Thr  Lys  Leu
385                           390                      395                 400
Ile  Leu  Ser  Glu  Arg  Asp  Arg  Leu  Gly  Ile  Lys  Thr  Val  Trp  Pro  Thr
                    405                      410                      415
Arg  Glu  Tyr  Thr  Asp  Phe  Arg  Glu  Tyr  Phe  Met  Glu  Val  Ala  Asp  Leu
               420                      425                      430
Ser  Ser  Pro  Leu  Lys  Ile  Ala  Gly  Ala  Phe  Gly  Phe  Lys  Asp  Ile  Ile
               435                      440                      445
Arg  Ala  Ile  Arg  Arg  Ile  Ala  Val  Pro  Val  Val  Ser  Thr  Leu  Phe  Pro
     450                      455                      460
Pro  Ala  Ala  Pro  Leu  Ala  His  Ala  Ile  Gly  Glu  Gly  Val  Asp  Tyr  Leu
465                      470                      475                      480
Leu  Gly  Asp  Glu  Ala  Gln  Ala  Ala  Ser  Gly  Thr  Ala  Arg  Ala  Ala  Ser
               485                      490                      495
Gly  Lys  Ala  Arg  Ala  Ala  Ser  Gly  Arg  Ile  Arg  Gln  Leu  Thr  Leu  Ala
               500                      505                      510
Ala  Asp  Lys  Gly  Tyr  Glu  Val  Val  Ala  Asn  Leu  Phe  Gln  Val  Pro  Gln
          515                      520                      525
Asn  Pro  Val  Val  Asp  Gly  Ile  Leu  Ala  Ser  Pro  Gly  Ile  Leu  Arg  Gly
     530                      535                      540
Ala  His  Asn  Leu  Asp  Cys  Val  Leu  Arg  Glu  Gly  Ala  Thr  Leu  Phe  Pro
545                      550                      555                      560
Val  Val  Ile  Thr  Thr  Val  Glu  Asp  Ala  Met  Thr  Pro  Lys  Ala  Leu  Asn
               565                      570                      575
Ser  Lys  Met  Phe  Ala  Val  Ile  Glu  Gly  Val  Arg  Glu  Asp  Leu  Gln  Pro
               580                      585                      590
Pro  Ser  Gln  Arg  Gly  Ser  Phe  Ile  Arg  Thr  Leu  Ser  Gly  His  Arg  Val
          595                      600                      605
Tyr  Gly  Tyr  Ala  Pro  Asp  Gly  Val  Leu  Pro  Leu  Glu  Thr  Gly  Arg  Asp
     610                      615                      620
Tyr  Thr  Val  Val  Pro  Ile  Asp  Asp  Val  Trp  Asp  Asp  Ser  Ile  Met  Leu
625                      630                      635                      640
Ser  Lys  Asp  Pro  Ile  Pro  Pro  Ile  Val  Gly  Asn  Ser  Gly  Asn  Leu  Ala
               645                      650                      655
Ile  Ala  Tyr  Met  Asp  Val  Phe  Arg  Pro  Lys  Val  Pro  Ile  His  Val  Ala
               660                      665                      670
```

| | | | | | | | | | | | | | |
|---|---|---|---|---|---|---|---|---|---|---|---|---|---|
|Met|Thr|Gly|Ala|Leu|Asn|Ala|Cys|Gly|Glu|Ile|Glu|Lys|Ile|Ser|Phe|
| |675| | | |680| | | |685| | | | |
|Arg|Ser|Thr|Lys|Leu|Ala|Thr|Ala|His|Arg|Leu|Gly|Leu|Lys|Leu|Ala|
| |690| | | |695| | | |700| | | | |
|Gly|Pro|Gly|Ala|Phe|Asp|Val|Asn|Thr|Gly|Pro|Asn|Trp|Ala|Thr|Phe|
|705| | | |710| | | |715| | | | |720|
|Ile|Lys|Arg|Phe|Pro|His|Asn|Pro|Arg|Asp|Trp|Asp|Arg|Leu|Pro|Tyr|
| | | |725| | | |730| | | | |735|
|Leu|Asn|Leu|Pro|Tyr|Leu|Pro|Pro|Asn|Ala|Gly|Arg|Gln|Tyr|His|Leu|
| | | |740| | | |745| | | | |750|
|Ala|Met|Ala|Ala|Ser|Glu|Phe|Lys|Glu|Thr|Pro|Glu|Leu|Glu|Ser|Ala|
| | |755| | | |760| | | |765|
|Val|Arg|Ala|Met|Glu|Ala|Ala|Ala|Ser|Val|Asp|Pro|Leu|Phe|Gln|Ser|
| |770| | | |775| | | |780|
|Ala|Leu|Ser|Val|Phe|Met|Trp|Leu|Glu|Glu|Asn|Gly|Ile|Val|Thr|Asp|
|785| | | |790| | | |795| | | | |800|
|Met|Ala|Asn|Phe|Ala|Leu|Ser|Asp|Pro|Asn|Ala|His|Arg|Met|Arg|Asn|
| | | |805| | | |810| | | | |815|
|Phe|Leu|Ala|Asn|Ala|Pro|Gln|Ala|Gly|Ser|Lys|Ser|Gln|Arg|Ala|Lys|
| | | |820| | | |825| | | | |830|
|Tyr|Gly|Thr|Ala|Gly|Tyr|Gly|Val|Glu|Ala|Arg|Gly|Pro|Thr|Pro|Glu|
| | |835| | | |840| | | |845|
|Glu|Ala|Gln|Arg|Glu|Lys|Asp|Thr|Arg|Ile|Ser|Lys|Lys|Met|Glu|Thr|
| |850| | | |855| | | |860|
|Met|Gly|Ile|Tyr|Phe|Ala|Thr|Pro|Glu|Trp|Val|Ala|Leu|Asn|Gly|His|
|865| | | |870| | | |875| | | | |880|
|Arg|Gly|Pro|Ser|Pro|Gly|Gln|Leu|Lys|Tyr|Trp|Gln|Asn|Thr|Arg|Glu|
| | | |885| | | |890| | | | |895|
|Ile|Pro|Asp|Pro|Asn|Glu|Asp|Tyr|Leu|Asp|Tyr|Val|His|Ala|Glu|Lys|
| | |900| | | |905| | | | |910|
|Ser|Arg|Leu|Ala|Ser|Glu|Glu|Gln|Ile|Leu|Arg|Ala|Ala|Thr|Ser|Ile|
| | |915| | | |920| | | | |925|
|Tyr|Gly|Ala|Pro|Gly|Gln|Ala|Glu|Pro|Pro|Gln|Ala|Phe|Ile|Asp|Glu|
| |930| | | |935| | | |940|
|Val|Ala|Lys|Val|Tyr|Glu|Ile|Asn|His|Gly|Arg|Gly|Pro|Asn|Gln|Glu|
|945| | | |950| | | |955| | | | |960|
|Gln|Met|Lys|Asp|Leu|Leu|Leu|Thr|Ala|Met|Glu|Met|Lys|His|Arg|Asn|
| | | |965| | | |970| | | | |975|
|Pro|Arg|Arg|Ala|Pro|Pro|Lys|Pro|Lys|Pro|Arg|Pro|Asn|Ala|Pro|Thr|
| | |980| | | |985| | | |990|
|Gln|Arg|Pro|Pro|Gly|Arg|Leu|Gly|Arg|Trp|Ile|Arg|Thr|Val|Ser|Asp|
| |995| | | |1000| | | |1005|
|Glu|Asp|Leu|Glu|
| |1010|

( 2 ) INFORMATION FOR SEQ ID NO:20:

( i ) SEQUENCE CHARACTERISTICS:
        ( A ) LENGTH: 9 amino acids
        ( B ) TYPE: amino acid
        ( D ) TOPOLOGY: unknown ( i i ) MOLECULE TYPE: peptide ( v i ) ORIGINAL SOURCE:
        ( A ) ORGANISM: Infectious bursal disease virus
        ( B ) STRAIN: GLS-5

( x i ) SEQUENCE DESCRIPTION: SEQ ID NO:20:

Asp His Ser Thr Thr Gly Glu Asp Ser
1               5

( 2 ) INFORMATION FOR SEQ ID NO:21:

( i ) SEQUENCE CHARACTERISTICS:
        ( A ) LENGTH: 9 amino acids
        ( B ) TYPE: amino acid
        ( D ) TOPOLOGY: unknown ( i i ) MOLECULE TYPE: peptide ( v i ) ORIGINAL SOURCE:
        ( A ) ORGANISM: Infectious bursal disease virus
        ( B ) STRAIN: E/Delaware ( x i ) SEQUENCE DESCRIPTION: SEQ ID NO:21:

Asn Gln Thr Ala Ile Asp Ala Glu Asn
1               5

( 2 ) INFORMATION FOR SEQ ID NO:22:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Thr Ser Lys Ser Gly Gly Gln Ala Gly Asp Gln
1               5                   1 0

( 2 ) INFORMATION FOR SEQ ID NO:23:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Asn Asn Gly Leu Thr Thr Gly Thr Asp Asn Leu
1               5                   1 0

( 2 ) INFORMATION FOR SEQ ID NO:24:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Ile Gly Phe Asp Gly Thr Thr Val Ile Thr Arg
1               5                   1 0

( 2 ) INFORMATION FOR SEQ ID NO:25:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
       Gly Gly Gln Glu Gly Asp Gln Met Ser Trp Ser Ala Ser
         1               5                   10
```

( 2 ) INFORMATION FOR SEQ ID NO:26:

( i ) SEQUENCE CHARACTERISTICS:
        ( A ) LENGTH: 348 base pairs
        ( B ) TYPE: nucleic acid
        ( C ) STRANDEDNESS: unknown
        ( D ) TOPOLOGY: linear ( i i ) MOLECULE TYPE: cDNA ( v i ) ORIGINAL SOURCE:
        ( A ) ORGANISM: Infectious bursal disease virus
        ( B ) STRAIN: GLS ( i x ) FEATURE:
        ( A ) NAME/KEY: CDS
        ( B ) LOCATION: 81..347

( x i ) SEQUENCE DESCRIPTION: SEQ ID NO:26:

```
CCCCGGGGGA GTCACCCGGG GACAGGCCGT CAAGGCCTTG TTCCAGGATG GAACTCCCCC      60

TTCTACAATG CTATCATTGA TGG TTA GTA GAG ATC GGA CAA ACG ATC GCA        110
                         Trp Leu Val Glu Ile Gly Gln Thr Ile Ala
                          1               5                   10

GCG ATG ACA AAC CTG CAA GAT CAA ACC CAA CAG ATT GTT CCG TTC ATA      158
Ala Met Thr Asn Leu Gln Asp Gln Thr Gln Gln Ile Val Pro Phe Ile
             15                  20                  25

CGG AGC CTT CTG ATG CCA ACA ACC GGA CCG GCG TCC ATT CCG GAC GAC      206
Arg Ser Leu Leu Met Pro Thr Thr Gly Pro Ala Ser Ile Pro Asp Asp
         30                  35                  40

ACC CTG GAG AAG CAC ACT CTC AGG TCA GAG ACC TCG ACC TAC AAT TTG      254
Thr Leu Glu Lys His Thr Leu Arg Ser Glu Thr Ser Thr Tyr Asn Leu
         45                  50                  55

ACT GTG GGG GAC ACA GGG TCA GGG CTA ATT GTC TTT TTC CCT GGA TTC      302
Thr Val Gly Asp Thr Gly Ser Gly Leu Ile Val Phe Phe Pro Gly Phe
         60                  65                  70

CCT GGC TCA ATT GTG GGT GCT CAC TAC ACA CTG CAG AGC AAT GGG          347
Pro Gly Ser Ile Val Gly Ala His Tyr Thr Leu Gln Ser Asn Gly
 75                  80                  85

A                                                                    348
```

( 2 ) INFORMATION FOR SEQ ID NO:27:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Trp Leu Val Glu Ile Gly Gln Thr Ile Ala Ala Met Thr Asn Leu Gln
 1               5                  10                  15

Asp Gln Thr Gln Gln Ile Val Pro Phe Ile Arg Ser Leu Leu Met Pro
             20                  25                  30

Thr Thr Gly Pro Ala Ser Ile Pro Asp Asp Thr Leu Glu Lys His Thr
         35                  40                  45

Leu Arg Ser Glu Thr Ser Thr Tyr Asn Leu Thr Val Gly Asp Thr Gly
         50                  55                  60

Ser Gly Leu Ile Val Phe Phe Pro Gly Phe Pro Gly Ser Ile Val Gly
 65                  70                  75                  80
```

Ala His Tyr Thr Leu Gln Ser Asn Gly
            85

( 2 ) INFORMATION FOR SEQ ID NO:28:

( i ) SEQUENCE CHARACTERISTICS:
        ( A ) LENGTH: 970 base pairs
        ( B ) TYPE: nucleic acid
        ( C ) STRANDEDNESS: unknown
        ( D ) TOPOLOGY: linear ( i i ) MOLECULE TYPE: cDNA ( v i ) ORIGINAL SOURCE:
        ( A ) ORGANISM: Infectious bursal disease virus
        ( B ) STRAIN: GLS ( i x ) FEATURE:
        ( A ) NAME/KEY: CDS
        ( B ) LOCATION: 3..968

( x i ) SEQUENCE DESCRIPTION: SEQ ID NO:28:

```
TT  GTC  TTT  TTC  CCT  GGA  TTC  CCT  GGC  TCA  ATT  GTG  GGT  GCT  CAC  TAC         47
    Val  Phe  Phe  Pro  Gly  Phe  Pro  Gly  Ser  Ile  Val  Gly  Ala  His  Tyr
     1              5                        10                        15

ACA  CTG  CAG  AGC  AAT  GGG  AAC  TAC  AAG  TTC  GAT  CAG  ATG  CTC  CTG  ACT         95
Thr  Leu  Gln  Ser  Asn  Gly  Asn  Tyr  Lys  Phe  Asp  Gln  Met  Leu  Leu  Thr
                    20                       25                        30

GCC  CAG  AAC  CTA  CCG  CCC  AGC  TAC  AAC  TAC  TGC  AGG  CTA  GTG  AGT  CGG        143
Ala  Gln  Asn  Leu  Pro  Pro  Ser  Tyr  Asn  Tyr  Cys  Arg  Leu  Val  Ser  Arg
               35                        40                        45

AGT  CTC  ACA  GTA  AGG  TCA  AGC  ACA  CTC  CCT  GGT  GGC  GTT  TAT  GCA  CTA        191
Ser  Leu  Thr  Val  Arg  Ser  Ser  Thr  Leu  Pro  Gly  Gly  Val  Tyr  Ala  Leu
          50                        55                        60

AAC  GGC  ACC  ATA  AAC  GCC  GTG  ACC  TTC  CAA  GGA  AGC  CTG  AGT  GAA  CTG        239
Asn  Gly  Thr  Ile  Asn  Ala  Val  Thr  Phe  Gln  Gly  Ser  Leu  Ser  Glu  Leu
     65                        70                        75

ACA  GAT  GTT  AGC  TAC  AAT  GGG  TTG  ATG  TCT  GCA  ACA  GCC  AAC  ATG  AAC        287
Thr  Asp  Val  Ser  Tyr  Asn  Gly  Leu  Met  Ser  Ala  Thr  Ala  Asn  Met  Asn
80                        85                        90                        95

GAC  AAA  ATT  GGG  AAC  GTC  CTA  GTA  GGG  GAA  GGG  GTT  ACT  GTC  CTC  AGC        335
Asp  Lys  Ile  Gly  Asn  Val  Leu  Val  Gly  Glu  Gly  Val  Thr  Val  Leu  Ser
                    100                      105                      110

TTA  CCC  ACA  TCA  TAT  GAT  CTT  GGG  TAT  GTG  AGG  CTT  GGT  GAC  CCC  ATA        383
Leu  Pro  Thr  Ser  Tyr  Asp  Leu  Gly  Tyr  Val  Arg  Leu  Gly  Asp  Pro  Ile
               115                       120                      125

CCC  GCT  ATA  GGG  CTT  GAC  CCA  AAA  ATG  GTA  GCA  ACA  TGT  GAC  AGC  AGT        431
Pro  Ala  Ile  Gly  Leu  Asp  Pro  Lys  Met  Val  Ala  Thr  Cys  Asp  Ser  Ser
          130                      135                       140

GAC  AGG  CCC  AGA  GTC  TAC  ACC  ATA  ACT  GCA  GCT  GAT  GAT  TAC  CAA  TTC        479
Asp  Arg  Pro  Arg  Val  Tyr  Thr  Ile  Thr  Ala  Ala  Asp  Asp  Tyr  Gln  Phe
     145                      150                       155

TCA  TCA  CAG  TAC  CAA  ACA  GGT  GGG  GTA  ACA  ATC  ACC  CTG  TTC  TCA  GCC        527
Ser  Ser  Gln  Tyr  Gln  Thr  Gly  Gly  Val  Thr  Ile  Thr  Leu  Phe  Ser  Ala
160                       165                      170                       175

AAC  ATT  GAT  GCC  ATC  ACA  AGC  CTC  AGC  GTT  GGG  GGA  GAG  CTC  GTG  TTT        575
Asn  Ile  Asp  Ala  Ile  Thr  Ser  Leu  Ser  Val  Gly  Gly  Glu  Leu  Val  Phe
                    180                      185                      190

AAA  ACA  AGC  GTC  CAC  AGC  CTT  GTA  CTG  GGC  GCC  ACC  ATC  TAC  CTT  ATA        623
Lys  Thr  Ser  Val  His  Ser  Leu  Val  Leu  Gly  Ala  Thr  Ile  Tyr  Leu  Ile
               195                      200                       205

GGC  TTT  GAT  GGG  TCT  GCG  GTA  ATC  ACT  AGA  GCT  GTG  GCC  GCA  AAC  AAT        671
Gly  Phe  Asp  Gly  Ser  Ala  Val  Ile  Thr  Arg  Ala  Val  Ala  Ala  Asn  Asn
          210                      215                      220
```

| | | | | | | | | | | | | | | | | |
|---|---|---|---|---|---|---|---|---|---|---|---|---|---|---|---|---|
| GGG | CTG | ACG | ACC | GGC | ACC | GAC | AAT | CTT | ATG | CCA | TTC | AAT | CTT | GTG | ATT | 719 |
| Gly | Leu | Thr | Thr | Gly | Thr | Asp | Asn | Leu | Met | Pro | Phe | Asn | Leu | Val | Ile | |
| | 225 | | | | 230 | | | | | 235 | | | | | | |
| CCA | ACC | AAC | GAG | ATA | ACC | CAG | CCA | ATC | ACA | TCC | ATC | AAA | CTG | GAG | ATA | 767 |
| Pro | Thr | Asn | Glu | Ile | Thr | Gln | Pro | Ile | Thr | Ser | Ile | Lys | Leu | Glu | Ile | |
| 240 | | | | | 245 | | | | | 250 | | | | | 255 | |
| GTG | ACC | TCC | AAA | AGT | GGT | GGT | CAG | GAA | GGG | GAC | CAG | ATG | TCA | TGG | TCG | 815 |
| Val | Thr | Ser | Lys | Ser | Gly | Gly | Gln | Glu | Gly | Asp | Gln | Met | Ser | Trp | Ser | |
| | | | | 260 | | | | | 265 | | | | | 270 | | |
| GCA | AGT | GGG | AGC | CTA | GCA | GTG | ACG | ATT | CAT | GGT | GGC | AAC | TAT | CCA | GGG | 863 |
| Ala | Ser | Gly | Ser | Leu | Ala | Val | Thr | Ile | His | Gly | Gly | Asn | Tyr | Pro | Gly | |
| | | | 275 | | | | 280 | | | | | 285 | | | | |
| GCC | CTC | CGT | CCC | GTC | ACA | CTA | GTA | GCC | TAC | GAA | AGA | GTG | GCA | ACA | GGA | 911 |
| Ala | Leu | Arg | Pro | Val | Thr | Leu | Val | Ala | Tyr | Glu | Arg | Val | Ala | Thr | Gly | |
| | | 290 | | | | 295 | | | | | 300 | | | | | |
| TCT | GTC | GTT | ACG | GTC | GCT | GGG | GTG | AGC | AAC | TTC | GAG | CTG | ATC | CCA | AAT | 959 |
| Ser | Val | Val | Thr | Val | Ala | Gly | Val | Ser | Asn | Phe | Glu | Leu | Ile | Pro | Asn | |
| | 305 | | | | | 310 | | | | | 315 | | | | | |
| CCT | GAA | CTA | GC | | | | | | | | | | | | | 970 |
| Pro | Glu | Leu | | | | | | | | | | | | | | |
| 320 | | | | | | | | | | | | | | | | |

( 2 ) INFORMATION FOR SEQ ID NO:29:

( i ) SEQUENCE CHARACTERISTICS:
( A ) LENGTH: 322 amino acids
( B ) TYPE: amino acid
( D ) TOPOLOGY: linear ( i i ) MOLECULE TYPE: protein ( x i ) SEQUENCE DESCRIPTION: SEQ ID NO:29:

| | | | | | | | | | | | | | | |
|---|---|---|---|---|---|---|---|---|---|---|---|---|---|---|
| Val | Phe | Phe | Pro | Gly | Phe | Pro | Gly | Ser | Ile | Val | Gly | Ala | His | Tyr | Thr |
| 1 | | | | 5 | | | | | 10 | | | | | 15 |
| Leu | Gln | Ser | Asn | Gly | Asn | Tyr | Lys | Phe | Asp | Gln | Met | Leu | Leu | Thr | Ala |
| | | | 20 | | | | | 25 | | | | | 30 | |
| Gln | Asn | Leu | Pro | Pro | Ser | Tyr | Asn | Tyr | Cys | Arg | Leu | Val | Ser | Arg | Ser |
| | | 35 | | | | | 40 | | | | | 45 | | |
| Leu | Thr | Val | Arg | Ser | Ser | Thr | Leu | Pro | Gly | Gly | Val | Tyr | Ala | Leu | Asn |
| | 50 | | | | | 55 | | | | | 60 | | | |
| Gly | Thr | Ile | Asn | Ala | Val | Thr | Phe | Gln | Gly | Ser | Leu | Ser | Glu | Leu | Thr |
| 65 | | | | | 70 | | | | | 75 | | | | | 80 |
| Asp | Val | Ser | Tyr | Asn | Gly | Leu | Met | Ser | Ala | Thr | Ala | Asn | Met | Asn | Asp |
| | | | | 85 | | | | | 90 | | | | | 95 |
| Lys | Ile | Gly | Asn | Val | Leu | Val | Gly | Glu | Gly | Val | Thr | Val | Leu | Ser | Leu |
| | | | 100 | | | | | 105 | | | | | 110 | |
| Pro | Thr | Ser | Tyr | Asp | Leu | Gly | Tyr | Val | Arg | Leu | Gly | Asp | Pro | Ile | Pro |
| | | 115 | | | | | 120 | | | | | 125 | | |
| Ala | Ile | Gly | Leu | Asp | Pro | Lys | Met | Val | Ala | Thr | Cys | Asp | Ser | Ser | Asp |
| | 130 | | | | | 135 | | | | | 140 | | | |
| Arg | Pro | Arg | Val | Tyr | Thr | Ile | Thr | Ala | Ala | Asp | Asp | Tyr | Gln | Phe | Ser |
| 145 | | | | | 150 | | | | | 155 | | | | | 160 |
| Ser | Gln | Tyr | Gln | Thr | Gly | Gly | Val | Thr | Ile | Thr | Leu | Phe | Ser | Ala | Asn |
| | | | | 165 | | | | | 170 | | | | | 175 |
| Ile | Asp | Ala | Ile | Thr | Ser | Leu | Ser | Val | Gly | Gly | Glu | Leu | Val | Phe | Lys |
| | | | 180 | | | | | 185 | | | | | 190 | |
| Thr | Ser | Val | His | Ser | Leu | Val | Leu | Gly | Ala | Thr | Ile | Tyr | Leu | Ile | Gly |
| | | 195 | | | | | 200 | | | | | 205 | | |
| Phe | Asp | Gly | Ser | Ala | Val | Ile | Thr | Arg | Ala | Val | Ala | Ala | Asn | Asn | Gly |

|     |     |     |     | 210 |     |     |     |     | 215 |     |     |     |     | 220 |     |
| --- | --- | --- | --- | --- | --- | --- | --- | --- | --- | --- | --- | --- | --- | --- | --- |
| Leu | Thr | Thr | Gly | Thr | Asp | Asn | Leu | Met | Pro | Phe | Asn | Leu | Val | Ile | Pro |
| 225 |     |     |     |     | 230 |     |     |     |     | 235 |     |     |     |     | 240 |
| Thr | Asn | Glu | Ile | Thr | Gln | Pro | Ile | Thr | Ser | Ile | Lys | Leu | Glu | Ile | Val |
|     |     |     |     | 245 |     |     |     |     | 250 |     |     |     |     | 255 |     |
| Thr | Ser | Lys | Ser | Gly | Gly | Gln | Glu | Gly | Asp | Gln | Met | Ser | Trp | Ser | Ala |
|     |     |     | 260 |     |     |     |     | 265 |     |     |     |     | 270 |     |     |
| Ser | Gly | Ser | Leu | Ala | Val | Thr | Ile | His | Gly | Gly | Asn | Tyr | Pro | Gly | Ala |
|     |     | 275 |     |     |     |     | 280 |     |     |     |     | 285 |     |     |     |
| Leu | Arg | Pro | Val | Thr | Leu | Val | Ala | Tyr | Glu | Arg | Val | Ala | Thr | Gly | Ser |
|     | 290 |     |     |     |     | 295 |     |     |     |     | 300 |     |     |     |     |
| Val | Val | Thr | Val | Ala | Gly | Val | Ser | Asn | Phe | Glu | Leu | Ile | Pro | Asn | Pro |
| 305 |     |     |     |     | 310 |     |     |     |     | 315 |     |     |     |     | 320 |
| Glu | Leu |     |     |     |     |     |     |     |     |     |     |     |     |     |     |

( 2 ) INFORMATION FOR SEQ ID NO:30:

( i ) SEQUENCE CHARACTERISTICS:
    ( A ) LENGTH: 1622 base pairs
    ( B ) TYPE: nucleic acid
    ( C ) STRANDEDNESS: unknown
    ( D ) TOPOLOGY: linear ( i i ) MOLECULE TYPE: cDNA ( v i ) ORIGINAL SOURCE:
    ( A ) ORGANISM: Infectious bursal disease virus
    ( B ) STRAIN: GLS ( i x ) FEATURE:
    ( A ) NAME/KEY: CDS
    ( B ) LOCATION: 1..1620

( x i ) SEQUENCE DESCRIPTION: SEQ ID NO:30:

| ATT | CCA | ACC | AAC | GAG | ATA | ACC | CAG | CCA | ATC | ACA | TCC | ATC | AAA | CTG | GAG | 48 |
| --- | --- | --- | --- | --- | --- | --- | --- | --- | --- | --- | --- | --- | --- | --- | --- | --- |
| Ile | Pro | Thr | Asn | Glu | Ile | Thr | Gln | Pro | Ile | Thr | Ser | Ile | Lys | Leu | Glu |    |
| 1   |     |     |     | 5   |     |     |     |     | 10  |     |     |     |     | 15  |     |    |
| ATA | GTG | ACC | TCC | AAA | AGT | GGT | GGT | CAG | GAA | GGG | GAC | CAG | ATG | TCA | TGG | 96 |
| Ile | Val | Thr | Ser | Lys | Ser | Gly | Gly | Gln | Glu | Gly | Asp | Gln | Met | Ser | Trp |    |
|     |     |     | 20  |     |     |     |     | 25  |     |     |     |     | 30  |     |     |    |
| TCG | GCA | AGT | GGG | AGC | CTA | GCA | GTG | ACG | ATT | CAT | GGT | GGC | AAC | TAT | CCA | 144 |
| Ser | Ala | Ser | Gly | Ser | Leu | Ala | Val | Thr | Ile | His | Gly | Gly | Asn | Tyr | Pro |    |
|     |     | 35  |     |     |     |     | 40  |     |     |     |     | 45  |     |     |     |    |
| GGG | GCC | CTC | CGT | CCC | GTC | ACA | CTA | GTA | GCC | TAC | GAA | AGA | GTG | GCA | ACA | 192 |
| Gly | Ala | Leu | Arg | Pro | Val | Thr | Leu | Val | Ala | Tyr | Glu | Arg | Val | Ala | Thr |    |
|     | 50  |     |     |     |     | 55  |     |     |     |     | 60  |     |     |     |     |    |
| GGA | TCT | GTC | GTT | ACG | GTC | GCT | GGG | GTG | AGC | AAC | TTC | GAG | CTG | ATC | CCA | 240 |
| Gly | Ser | Val | Val | Thr | Val | Ala | Gly | Val | Ser | Asn | Phe | Glu | Leu | Ile | Pro |    |
| 65  |     |     |     |     | 70  |     |     |     |     | 75  |     |     |     |     | 80  |    |
| AAT | CCT | GAA | CTA | GCA | AAG | AAC | CTG | GTT | ACA | GAA | TAC | GGC | CGA | TTT | GAC | 288 |
| Asn | Pro | Glu | Leu | Ala | Lys | Asn | Leu | Val | Thr | Glu | Tyr | Gly | Arg | Phe | Asp |    |
|     |     |     |     | 85  |     |     |     |     | 90  |     |     |     |     | 95  |     |    |
| CCA | GGA | GCC | ATG | AAC | TAC | ACA | AAA | TTG | ATA | CTG | AGT | GAG | AGG | GAC | CGC | 336 |
| Pro | Gly | Ala | Met | Asn | Tyr | Thr | Lys | Leu | Ile | Leu | Ser | Glu | Arg | Asp | Arg |    |
|     |     |     |     | 100 |     |     |     |     | 105 |     |     |     |     | 110 |     |    |
| CTT | GGC | ATC | AAG | ACA | GTC | TGG | CCG | ACA | AGG | GAG | TAC | ACC | GAC | TTT | CGT | 384 |
| Leu | Gly | Ile | Lys | Thr | Val | Trp | Pro | Thr | Arg | Glu | Tyr | Thr | Asp | Phe | Arg |    |
|     |     | 115 |     |     |     |     | 120 |     |     |     |     | 125 |     |     |     |    |
| GAG | TAC | TTC | ATG | GAG | GTG | GCC | GAC | CTC | AGC | TCT | CCC | CTG | AAG | ATT | GCA | 432 |
| Glu | Tyr | Phe | Met | Glu | Val | Ala | Asp | Leu | Ser | Ser | Pro | Leu | Lys | Ile | Ala |    |
|     | 130 |     |     |     |     | 135 |     |     |     |     | 140 |     |     |     |     |    |
| GGA | GCA | TTT | GGC | TTC | AAA | GAC | ATA | ATC | CGG | GCC | ATA | AGG | AGG | ATA | GCT | 480 |

|     |     |     |     |     |     |     |     |     |     |     |     |     |     |     |      |
| --- | --- | --- | --- | --- | --- | --- | --- | --- | --- | --- | --- | --- | --- | --- | ---- |
| Gly | Ala | Phe | Gly | Phe | Lys | Asp | Ile | Ile | Arg | Ala | Ile | Arg | Arg | Ile | Ala  |
| 145 |     |     |     | 150 |     |     |     |     | 155 |     |     |     |     | 160 |      |
| GTG | CCG | GTG | GTC | TCC | ACA | TTG | TTC | CCA | CCT | GCC | GCT | CCC | CTG | GCC | CAT  | 528 |
| Val | Pro | Val | Val | Ser | Thr | Leu | Phe | Pro | Pro | Ala | Ala | Pro | Leu | Ala | His  |
|     |     |     |     | 165 |     |     |     |     | 170 |     |     |     |     | 175 |      |
| GCA | ATT | GGG | GAA | GGT | GTA | GAC | TAC | CTG | CTG | GGT | GAT | GAG | GCA | CAG | GCT  | 576 |
| Ala | Ile | Gly | Glu | Gly | Val | Asp | Tyr | Leu | Leu | Gly | Asp | Glu | Ala | Gln | Ala  |
|     |     |     |     | 180 |     |     |     |     | 185 |     |     |     |     | 190 |      |
| GCT | TCA | GGA | ACT | GCT | CGA | GCC | GCG | TCA | GGA | AAA | GCA | AGG | GCT | GCC | TCA  | 624 |
| Ala | Ser | Gly | Thr | Ala | Arg | Ala | Ala | Ser | Gly | Lys | Ala | Arg | Ala | Ala | Ser  |
|     |     | 195 |     |     |     |     | 200 |     |     |     |     | 205 |     |     |      |
| GGC | CGC | ATA | AGG | CAG | CTG | ACT | CTC | GCC | GCC | GAC | AAG | GGG | TAC | GAG | GTA  | 672 |
| Gly | Arg | Ile | Arg | Gln | Leu | Thr | Leu | Ala | Ala | Asp | Lys | Gly | Tyr | Glu | Val  |
|     |     | 210 |     |     |     |     | 215 |     |     |     |     | 220 |     |     |      |
| GTC | GCG | AAT | CTA | TTC | CAG | GTG | CCC | CAG | AAT | CCC | GTA | GTC | GAC | GGG | ATT  | 720 |
| Val | Ala | Asn | Leu | Phe | Gln | Val | Pro | Gln | Asn | Pro | Val | Val | Asp | Gly | Ile  |
| 225 |     |     |     |     | 230 |     |     |     |     | 235 |     |     |     |     | 240  |
| CTT | GCT | TCA | CCC | GGG | ATA | CTC | CGC | GGT | GCA | CAC | AAC | CTC | GAC | TGC | GTG  | 768 |
| Leu | Ala | Ser | Pro | Gly | Ile | Leu | Arg | Gly | Ala | His | Asn | Leu | Asp | Cys | Val  |
|     |     |     |     | 245 |     |     |     |     | 250 |     |     |     |     | 255 |      |
| TTA | AGA | GAG | GGC | GCC | ACG | CTA | TTC | CCT | GTG | GTC | ATC | ACG | ACA | GTG | GAA  | 816 |
| Leu | Arg | Glu | Gly | Ala | Thr | Leu | Phe | Pro | Val | Val | Ile | Thr | Thr | Val | Glu  |
|     |     |     | 260 |     |     |     |     | 265 |     |     |     |     | 270 |     |      |
| GAC | GCC | ATG | ACA | CCC | AAA | GCA | CTA | AAC | AGC | AAA | ATG | TTT | GCT | GTC | ATT  | 864 |
| Asp | Ala | Met | Thr | Pro | Lys | Ala | Leu | Asn | Ser | Lys | Met | Phe | Ala | Val | Ile  |
|     |     | 275 |     |     |     |     | 280 |     |     |     |     | 285 |     |     |      |
| GAA | GGC | GTG | CGA | GAG | GAC | CTC | CAA | CCT | CCA | TCT | CAA | AGA | GGA | TCC | TTC  | 912 |
| Glu | Gly | Val | Arg | Glu | Asp | Leu | Gln | Pro | Pro | Ser | Gln | Arg | Gly | Ser | Phe  |
|     | 290 |     |     |     |     | 295 |     |     |     |     | 300 |     |     |     |      |
| ATA | CGA | ACT | CTC | TCC | GGA | CAC | AGA | GTC | TAT | GGA | TAT | GCT | CCA | GAT | GGG  | 960 |
| Ile | Arg | Thr | Leu | Ser | Gly | His | Arg | Val | Tyr | Gly | Tyr | Ala | Pro | Asp | Gly  |
| 305 |     |     |     |     | 310 |     |     |     |     | 315 |     |     |     |     | 320  |
| GTA | CTT | CCA | CTG | GAG | ACT | GGG | AGA | GAC | TAC | ACC | GTT | GTC | CCA | ATA | GAT  | 1008 |
| Val | Leu | Pro | Leu | Glu | Thr | Gly | Arg | Asp | Tyr | Thr | Val | Val | Pro | Ile | Asp  |
|     |     |     |     | 325 |     |     |     |     | 330 |     |     |     |     | 335 |      |
| GAT | GTC | TGG | GAC | GAC | AGC | ATT | ATG | CTG | TCC | AAA | GAC | CCC | ATA | CCT | CCT  | 1056 |
| Asp | Val | Trp | Asp | Asp | Ser | Ile | Met | Leu | Ser | Lys | Asp | Pro | Ile | Pro | Pro  |
|     |     |     | 340 |     |     |     |     | 345 |     |     |     |     | 350 |     |      |
| ATT | GTG | GGA | AAC | AGT | GGA | AAC | CTA | GCC | ATA | GCT | TAC | ATG | GAT | GTG | TTT  | 1104 |
| Ile | Val | Gly | Asn | Ser | Gly | Asn | Leu | Ala | Ile | Ala | Tyr | Met | Asp | Val | Phe  |
|     |     | 355 |     |     |     |     | 360 |     |     |     |     | 365 |     |     |      |
| CGA | CCC | AAA | GTC | CCC | ATC | CAT | GTG | GCC | ATG | ACG | GGA | GCC | CTC | AAC | GCT  | 1152 |
| Arg | Pro | Lys | Val | Pro | Ile | His | Val | Ala | Met | Thr | Gly | Ala | Leu | Asn | Ala  |
|     | 370 |     |     |     |     | 375 |     |     |     |     | 380 |     |     |     |      |
| TGT | GGC | GAG | ATT | GAG | AAA | ATA | AGC | TTT | AGA | AGC | ACC | AAG | CTC | GCC | ACC  | 1200 |
| Cys | Gly | Glu | Ile | Glu | Lys | Ile | Ser | Phe | Arg | Ser | Thr | Lys | Leu | Ala | Thr  |
| 385 |     |     |     |     | 390 |     |     |     |     | 395 |     |     |     |     | 400  |
| GCA | CAC | CGG | CTT | GGC | CTC | AAG | TTG | GCT | GGT | CCC | GGA | GCA | TTT | GAT | GTA  | 1248 |
| Ala | His | Arg | Leu | Gly | Leu | Lys | Leu | Ala | Gly | Pro | Gly | Ala | Phe | Asp | Val  |
|     |     |     |     | 405 |     |     |     |     | 410 |     |     |     |     | 415 |      |
| AAC | ACC | GGG | CCC | AAC | TGG | GCA | ACG | TTC | ATC | AAA | CGT | TTC | CCT | CAC | AAT  | 1296 |
| Asn | Thr | Gly | Pro | Asn | Trp | Ala | Thr | Phe | Ile | Lys | Arg | Phe | Pro | His | Asn  |
|     |     |     | 420 |     |     |     |     | 425 |     |     |     |     | 430 |     |      |
| CCA | CGC | GAC | TGG | GAC | AGG | CTC | CCC | TAC | CTC | AAC | CTT | CCA | TAC | CTT | CCA  | 1344 |
| Pro | Arg | Asp | Trp | Asp | Arg | Leu | Pro | Tyr | Leu | Asn | Leu | Pro | Tyr | Leu | Pro  |
|     |     | 435 |     |     |     |     | 440 |     |     |     |     | 445 |     |     |      |
| CCC | AAT | GCA | GGA | CGC | CAG | TAC | CAC | CTC | GCC | ATG | GCC | GCA | TCA | GAG | TTC  | 1392 |
| Pro | Asn | Ala | Gly | Arg | Gln | Tyr | His | Leu | Ala | Met | Ala | Ala | Ser | Glu | Phe  |
|     | 450 |     |     |     |     | 455 |     |     |     |     | 460 |     |     |     |      |
| AAG | GAG | ACC | CCT | GAA | CTC | GAG | AGC | GCC | GTC | AGG | GCC | ATG | GAA | GCA | GCA  | 1440 |

```
Lys Glu Thr Pro Glu Leu Glu Ser Ala Val Arg Ala Met Glu Ala Ala
465                 470                 475                 480

GCC AGT GTA GAC CCA CTG TTC CAA TCT GCA CTC AGT GTG TTC ATG TGG        1488
Ala Ser Val Asp Pro Leu Phe Gln Ser Ala Leu Ser Val Phe Met Trp
                485                 490                 495

CTG GAA GAG AAT GGG ATT GTG ACT GAC ATG GCC AAC TTC GCA CTC AGC        1536
Leu Glu Glu Asn Gly Ile Val Thr Asp Met Ala Asn Phe Ala Leu Ser
            500                 505                 510

GAC CCG AAC GCC CAT CGG ATG CGA AAC TTT CTT GCA AAC GCA CCA CAA        1584
Asp Pro Asn Ala His Arg Met Arg Asn Phe Leu Ala Asn Ala Pro Gln
        515                 520                 525

GCA GGT AGC AAG TCT CAA AGG GCC AAA TAC GGG ACA GC                     1622
Ala Gly Ser Lys Ser Gln Arg Ala Lys Tyr Gly Thr
    530                 535                 540
```

( 2 ) INFORMATION FOR SEQ ID NO:31:

( i ) SEQUENCE CHARACTERISTICS:
        ( A ) LENGTH: 540 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

```
Ile Pro Thr Asn Glu Ile Thr Gln Pro Ile Thr Ser Ile Lys Leu Glu
1               5                   10                  15

Ile Val Thr Ser Lys Ser Gly Gln Glu Gly Asp Gln Met Ser Trp
            20                  25                  30

Ser Ala Ser Gly Ser Leu Ala Val Thr Ile His Gly Gly Asn Tyr Pro
        35                  40                  45

Gly Ala Leu Arg Pro Val Thr Leu Val Ala Tyr Glu Arg Val Ala Thr
    50                  55                  60

Gly Ser Val Val Thr Val Ala Gly Val Ser Asn Phe Glu Leu Ile Pro
65                  70                  75                  80

Asn Pro Glu Leu Ala Lys Asn Leu Val Thr Glu Tyr Gly Arg Phe Asp
                85                  90                  95

Pro Gly Ala Met Asn Tyr Thr Lys Leu Ile Leu Ser Glu Arg Asp Arg
            100                 105                 110

Leu Gly Ile Lys Thr Val Trp Pro Thr Arg Glu Tyr Thr Asp Phe Arg
        115                 120                 125

Glu Tyr Phe Met Glu Val Ala Asp Leu Ser Ser Pro Leu Lys Ile Ala
    130                 135                 140

Gly Ala Phe Gly Phe Lys Asp Ile Ile Arg Ala Ile Arg Arg Ile Ala
145                 150                 155                 160

Val Pro Val Val Ser Thr Leu Phe Pro Pro Ala Ala Pro Leu Ala His
                165                 170                 175

Ala Ile Gly Glu Gly Val Asp Tyr Leu Leu Gly Asp Glu Ala Gln Ala
            180                 185                 190

Ala Ser Gly Thr Ala Arg Ala Ala Ser Gly Lys Ala Arg Ala Ala Ser
        195                 200                 205

Gly Arg Ile Arg Gln Leu Thr Leu Ala Ala Asp Lys Gly Tyr Glu Val
    210                 215                 220

Val Ala Asn Leu Phe Gln Val Pro Gln Asn Pro Val Val Asp Gly Ile
225                 230                 235                 240

Leu Ala Ser Pro Gly Ile Leu Arg Gly Ala His Asn Leu Asp Cys Val
                245                 250                 255

Leu Arg Glu Gly Ala Thr Leu Phe Pro Val Val Ile Thr Thr Val Glu
```

|             |             |             |
|-------------|-------------|-------------|
| 260         | 265         | 270         |

Asp Ala Met Thr Pro Lys Ala Leu Asn Ser Lys Met Phe Ala Val Ile
        275             280             285

Glu Gly Val Arg Glu Asp Leu Gln Pro Pro Ser Gln Arg Gly Ser Phe
        290             295             300

Ile Arg Thr Leu Ser Gly His Arg Val Tyr Gly Tyr Ala Pro Asp Gly
305             310             315             320

Val Leu Pro Leu Glu Thr Gly Arg Asp Tyr Thr Val Val Pro Ile Asp
        325             330             335

Asp Val Trp Asp Asp Ser Ile Met Leu Ser Lys Asp Pro Ile Pro Pro
        340             345             350

Ile Val Gly Asn Ser Gly Asn Leu Ala Ile Ala Tyr Met Asp Val Phe
        355             360             365

Arg Pro Lys Val Pro Ile His Val Ala Met Thr Gly Ala Leu Asn Ala
    370             375             380

Cys Gly Glu Ile Glu Lys Ile Ser Phe Arg Ser Thr Lys Leu Ala Thr
385             390             395             400

Ala His Arg Leu Gly Leu Lys Leu Ala Gly Pro Gly Ala Phe Asp Val
            405             410             415

Asn Thr Gly Pro Asn Trp Ala Thr Phe Ile Lys Arg Phe Pro His Asn
            420             425             430

Pro Arg Asp Trp Asp Arg Leu Pro Tyr Leu Asn Leu Pro Tyr Leu Pro
        435             440             445

Pro Asn Ala Gly Arg Gln Tyr His Leu Ala Met Ala Ala Ser Glu Phe
    450             455             460

Lys Glu Thr Pro Glu Leu Glu Ser Ala Val Arg Ala Met Glu Ala Ala
465             470             475             480

Ala Ser Val Asp Pro Leu Phe Gln Ser Ala Leu Ser Val Phe Met Trp
            485             490             495

Leu Glu Glu Asn Gly Ile Val Thr Asp Met Ala Asn Phe Ala Leu Ser
        500             505             510

Asp Pro Asn Ala His Arg Met Arg Asn Phe Leu Ala Asn Ala Pro Gln
        515             520             525

Ala Gly Ser Lys Ser Gln Arg Ala Lys Tyr Gly Thr
    530             535             540

( 2 ) INFORMATION FOR SEQ ID NO:32:

( i ) SEQUENCE CHARACTERISTICS:
        ( A ) LENGTH: 1509 base pairs
        ( B ) TYPE: nucleic acid
        ( C ) STRANDEDNESS: unknown
        ( D ) TOPOLOGY: linear ( i i ) MOLECULE TYPE: cDNA ( v i ) ORIGINAL SOURCE:
        ( A ) ORGANISM: Infectious bursal disease virus
        ( B ) STRAIN: GLS ( i x ) FEATURE:
        ( A ) NAME/KEY: CDS
        ( B ) LOCATION: 1..1428

( x i ) SEQUENCE DESCRIPTION: SEQ ID NO:32:

GCT TCA CCC GGG ATA CTC CGC GGT GCA CAC AAC CTC GAC TGC GTG TTA      48
Ala Ser Pro Gly Ile Leu Arg Gly Ala His Asn Leu Asp Cys Val Leu
 1               5                  10                  15

AGA GAG GGC GCC ACG CTA TTC CCT GTG GTC ATC ACG ACA GTG GAA GAC      96
Arg Glu Gly Ala Thr Leu Phe Pro Val Val Ile Thr Thr Val Glu Asp

|       |       |       |       |       |       |       |       |       |       |       |       |       |       |       |       |      |
|-------|-------|-------|-------|-------|-------|-------|-------|-------|-------|-------|-------|-------|-------|-------|-------|------|
|       |       | 20    |       |       |       |       | 25    |       |       |       |       | 30    |       |       |       |      |
| GCC   | ATG   | ACA   | CCC   | AAA   | GCA   | CTA   | AAC   | AGC   | AAA   | ATG   | TTT   | GCT   | GTC   | ATT   | GAA   | 144  |
| Ala   | Met   | Thr   | Pro   | Lys   | Ala   | Leu   | Asn   | Ser   | Lys   | Met   | Phe   | Ala   | Val   | Ile   | Glu   |      |
|       |       | 35    |       |       |       |       | 40    |       |       |       |       | 45    |       |       |       |      |
| GGC   | GTG   | CGA   | GAG   | GAC   | CTC   | CAA   | CCT   | CCA   | TCT   | CAA   | AGA   | GGA   | TCC   | TTC   | ATA   | 192  |
| Gly   | Val   | Arg   | Glu   | Asp   | Leu   | Gln   | Pro   | Pro   | Ser   | Gln   | Arg   | Gly   | Ser   | Phe   | Ile   |      |
|       | 50    |       |       |       |       | 55    |       |       |       |       | 60    |       |       |       |       |      |
| CGA   | ACT   | CTC   | TCC   | GGA   | CAC   | AGA   | GTC   | TAT   | GGA   | TAT   | GCT   | CCA   | GAT   | GGG   | GTA   | 240  |
| Arg   | Thr   | Leu   | Ser   | Gly   | His   | Arg   | Val   | Tyr   | Gly   | Tyr   | Ala   | Pro   | Asp   | Gly   | Val   |      |
| 65    |       |       |       |       | 70    |       |       |       |       | 75    |       |       |       |       | 80    |      |
| CTT   | CCA   | CTG   | GAG   | ACT   | GGG   | AGA   | GAC   | TAC   | ACC   | GTT   | GTC   | CCA   | ATA   | GAT   | GAT   | 288  |
| Leu   | Pro   | Leu   | Glu   | Thr   | Gly   | Arg   | Asp   | Tyr   | Thr   | Val   | Val   | Pro   | Ile   | Asp   | Asp   |      |
|       |       |       |       | 85    |       |       |       |       | 90    |       |       |       |       | 95    |       |      |
| GTC   | TGG   | GAC   | GAC   | AGC   | ATT   | ATG   | CTG   | TCC   | AAA   | GAC   | CCC   | ATA   | CCT   | CCT   | ATT   | 336  |
| Val   | Trp   | Asp   | Asp   | Ser   | Ile   | Met   | Leu   | Ser   | Lys   | Asp   | Pro   | Ile   | Pro   | Pro   | Ile   |      |
|       |       |       |       | 100   |       |       |       |       | 105   |       |       |       |       | 110   |       |      |
| GTG   | GGA   | AAC   | AGT   | GGA   | AAC   | CTA   | GCC   | ATA   | GCT   | TAC   | ATG   | GAT   | GTG   | TTT   | CGA   | 384  |
| Val   | Gly   | Asn   | Ser   | Gly   | Asn   | Leu   | Ala   | Ile   | Ala   | Tyr   | Met   | Asp   | Val   | Phe   | Arg   |      |
|       |       | 115   |       |       |       |       | 120   |       |       |       |       | 125   |       |       |       |      |
| CCC   | AAA   | GTC   | CCC   | ATC   | CAT   | GTG   | GCC   | ATG   | ACG   | GGA   | GCC   | CTC   | AAC   | GCT   | TGT   | 432  |
| Pro   | Lys   | Val   | Pro   | Ile   | His   | Val   | Ala   | Met   | Thr   | Gly   | Ala   | Leu   | Asn   | Ala   | Cys   |      |
|       | 130   |       |       |       |       | 135   |       |       |       |       | 140   |       |       |       |       |      |
| GGC   | GAG   | ATT   | GAG   | AAA   | ATA   | AGC   | TTT   | AGA   | AGC   | ACC   | AAG   | CTC   | GCC   | ACC   | GCA   | 480  |
| Gly   | Glu   | Ile   | Glu   | Lys   | Ile   | Ser   | Phe   | Arg   | Ser   | Thr   | Lys   | Leu   | Ala   | Thr   | Ala   |      |
| 145   |       |       |       |       | 150   |       |       |       |       | 155   |       |       |       |       | 160   |      |
| CAC   | CGG   | CTT   | GGC   | CTC   | AAG   | TTG   | GCT   | GGT   | CCC   | GGA   | GCA   | TTT   | GAT   | GTA   | AAC   | 528  |
| His   | Arg   | Leu   | Gly   | Leu   | Lys   | Leu   | Ala   | Gly   | Pro   | Gly   | Ala   | Phe   | Asp   | Val   | Asn   |      |
|       |       |       |       | 165   |       |       |       |       | 170   |       |       |       |       | 175   |       |      |
| ACC   | GGG   | CCC   | AAC   | TGG   | GCA   | ACG   | TTC   | ATC   | AAA   | CGT   | TTC   | CCT   | CAC   | AAT   | CCA   | 576  |
| Thr   | Gly   | Pro   | Asn   | Trp   | Ala   | Thr   | Phe   | Ile   | Lys   | Arg   | Phe   | Pro   | His   | Asn   | Pro   |      |
|       |       |       | 180   |       |       |       |       | 185   |       |       |       |       | 190   |       |       |      |
| CGC   | GAC   | TGG   | GAC   | AGG   | CTC   | CCC   | TAC   | CTC   | AAC   | CTT   | CCA   | TAC   | CTT   | CCA   | CCC   | 624  |
| Arg   | Asp   | Trp   | Asp   | Arg   | Leu   | Pro   | Tyr   | Leu   | Asn   | Leu   | Pro   | Tyr   | Leu   | Pro   | Pro   |      |
|       |       | 195   |       |       |       |       | 200   |       |       |       |       | 205   |       |       |       |      |
| AAT   | GCA   | GGA   | CGC   | CAG   | TAC   | CAC   | CTC   | GCC   | ATG   | GCC   | GCA   | TCA   | GAG   | TTC   | AAG   | 672  |
| Asn   | Ala   | Gly   | Arg   | Gln   | Tyr   | His   | Leu   | Ala   | Met   | Ala   | Ala   | Ser   | Glu   | Phe   | Lys   |      |
|       | 210   |       |       |       |       | 215   |       |       |       |       | 220   |       |       |       |       |      |
| GAG   | ACC   | CCT   | GAA   | CTC   | GAG   | AGC   | GCC   | GTC   | AGG   | GCC   | ATG   | GAA   | GCA   | GCA   | GCC   | 720  |
| Glu   | Thr   | Pro   | Glu   | Leu   | Glu   | Ser   | Ala   | Val   | Arg   | Ala   | Met   | Glu   | Ala   | Ala   | Ala   |      |
| 225   |       |       |       |       | 230   |       |       |       |       | 235   |       |       |       |       | 240   |      |
| AGT   | GTA   | GAC   | CCA   | CTG   | TTC   | CAA   | TCT   | GCA   | CTC   | AGT   | GTG   | TTC   | ATG   | TGG   | CTG   | 768  |
| Ser   | Val   | Asp   | Pro   | Leu   | Phe   | Gln   | Ser   | Ala   | Leu   | Ser   | Val   | Phe   | Met   | Trp   | Leu   |      |
|       |       |       |       | 245   |       |       |       |       | 250   |       |       |       |       | 255   |       |      |
| GAA   | GAG   | AAT   | GGG   | ATT   | GTG   | ACT   | GAC   | ATG   | GCC   | AAC   | TTC   | GCA   | CTC   | AGC   | GAC   | 816  |
| Glu   | Glu   | Asn   | Gly   | Ile   | Val   | Thr   | Asp   | Met   | Ala   | Asn   | Phe   | Ala   | Leu   | Ser   | Asp   |      |
|       |       |       | 260   |       |       |       |       | 265   |       |       |       |       | 270   |       |       |      |
| CCG   | AAC   | GCC   | CAT   | CGG   | ATG   | CGA   | AAC   | TTT   | CTT   | GCA   | AAC   | GCA   | CCA   | CAA   | GCA   | 864  |
| Pro   | Asn   | Ala   | His   | Arg   | Met   | Arg   | Asn   | Phe   | Leu   | Ala   | Asn   | Ala   | Pro   | Gln   | Ala   |      |
|       |       | 275   |       |       |       |       | 280   |       |       |       |       | 285   |       |       |       |      |
| GGT   | AGC   | AAG   | TCT   | CAA   | AGG   | GCC   | AAA   | TAC   | GGG   | ACA   | GCA   | GGC   | TAC   | GGA   | GTG   | 912  |
| Gly   | Ser   | Lys   | Ser   | Gln   | Arg   | Ala   | Lys   | Tyr   | Gly   | Thr   | Ala   | Gly   | Tyr   | Gly   | Val   |      |
|       | 290   |       |       |       |       | 295   |       |       |       |       | 300   |       |       |       |       |      |
| GAG   | GCC   | CGG   | GGC   | CCC   | ACA   | CCA   | GAA   | GAA   | GCA   | CAG   | AGG   | GAA   | AAA   | GAC   | ACA   | 960  |
| Glu   | Ala   | Arg   | Gly   | Pro   | Thr   | Pro   | Glu   | Glu   | Ala   | Gln   | Arg   | Glu   | Lys   | Asp   | Thr   |      |
| 305   |       |       |       |       | 310   |       |       |       |       | 315   |       |       |       |       | 320   |      |
| CGG   | ATC   | TCA   | AAG   | AAG   | ATG   | GAG   | ACC   | ATG   | GGC   | ATC   | TAC   | TTT   | GCA   | ACA   | CCA   | 1008 |
| Arg   | Ile   | Ser   | Lys   | Lys   | Met   | Glu   | Thr   | Met   | Gly   | Ile   | Tyr   | Phe   | Ala   | Thr   | Pro   |      |
|       |       |       |       | 325   |       |       |       |       | 330   |       |       |       |       | 335   |       |      |
| GAA   | TGG   | GTA   | GCA   | CTC   | AAT   | GGG   | CAC   | CGA   | GGG   | CCA   | AGC   | CCC   | GGC   | CAG   | CTA   | 1056 |
| Glu   | Trp   | Val   | Ala   | Leu   | Asn   | Gly   | His   | Arg   | Gly   | Pro   | Ser   | Pro   | Gly   | Gln   | Leu   |      |

|   |   |   |   |   | 340 |   |   |   |   | 345 |   |   |   |   | 350 |   |   |   |
|---|---|---|---|---|---|---|---|---|---|---|---|---|---|---|---|---|---|---|
| AAG | TAC | TGG | CAG | AAC | ACA | CGA | GAA | ATA | CCG | GAC | CCA | AAC | GAG | GAC | TAT |   |   | 1104 |
| Lys | Tyr | Trp | Gln | Asn | Thr | Arg | Glu | Ile | Pro | Asp | Pro | Asn | Glu | Asp | Tyr |   |   |   |
|   |   | 355 |   |   |   |   | 360 |   |   |   |   | 365 |   |   |   |   |   |   |
| CTA | GAC | TAC | GTG | CAT | GCA | GAG | AAG | AGC | CGG | TTG | GCA | TCA | GAA | GAA | CAA |   |   | 1152 |
| Leu | Asp | Tyr | Val | His | Ala | Glu | Lys | Ser | Arg | Leu | Ala | Ser | Glu | Glu | Gln |   |   |   |
|   | 370 |   |   |   |   | 375 |   |   |   |   | 380 |   |   |   |   |   |   |   |
| ATC | CTA | AGG | GCA | GCT | ACG | TCG | ATC | TAC | GGG | GCT | CCA | GGA | CAG | GCA | GAG |   |   | 1200 |
| Ile | Leu | Arg | Ala | Ala | Thr | Ser | Ile | Tyr | Gly | Ala | Pro | Gly | Gln | Ala | Glu |   |   |   |
| 385 |   |   |   |   | 390 |   |   |   |   | 395 |   |   |   |   | 400 |   |   |   |
| CCA | CCC | CAA | GCT | TTC | ATA | GAC | GAA | GTT | GCC | AAA | GTC | TAT | GAA | ATC | AAC |   |   | 1248 |
| Pro | Pro | Gln | Ala | Phe | Ile | Asp | Glu | Val | Ala | Lys | Val | Tyr | Glu | Ile | Asn |   |   |   |
|   |   |   |   | 405 |   |   |   |   | 410 |   |   |   |   | 415 |   |   |   |   |
| CAT | GGA | CGT | GGC | CCA | AAC | CAA | GAA | CAG | ATG | AAA | GAT | CTG | CTC | TTG | ACT |   |   | 1296 |
| His | Gly | Arg | Gly | Pro | Asn | Gln | Glu | Gln | Met | Lys | Asp | Leu | Leu | Leu | Thr |   |   |   |
|   |   |   | 420 |   |   |   |   | 425 |   |   |   |   | 430 |   |   |   |   |   |
| GCG | ATG | GAG | ATG | AAG | CAT | CGC | AAT | CCC | AGG | CGG | GCT | CCA | CCA | AAG | CCC |   |   | 1344 |
| Ala | Met | Glu | Met | Lys | His | Arg | Asn | Pro | Arg | Arg | Ala | Pro | Pro | Lys | Pro |   |   |   |
|   |   | 435 |   |   |   |   | 440 |   |   |   |   | 445 |   |   |   |   |   |   |
| AAG | CCA | AGA | CCC | AAC | GCT | CCA | ACG | CAG | AGA | CCC | CCT | GGT | CGG | CTG | GGC |   |   | 1392 |
| Lys | Pro | Arg | Pro | Asn | Ala | Pro | Thr | Gln | Arg | Pro | Pro | Gly | Arg | Leu | Gly |   |   |   |
|   | 450 |   |   |   |   | 455 |   |   |   |   | 460 |   |   |   |   |   |   |   |
| CGC | TGG | ATC | AGG | ACT | GTC | TCT | GAT | GAG | GAC | CTT | GAG | TGAGGCTCCT |   |   |   |   |   | 1438 |
| Arg | Trp | Ile | Arg | Thr | Val | Ser | Asp | Glu | Asp | Leu | Glu |   |   |   |   |   |   |   |
| 465 |   |   |   |   | 470 |   |   |   |   | 475 |   |   |   |   |   |   |   |   |

GGGAGTCTCC CGACACCACC CGCGCAGGCG TGGACACCAA TTCGGCCTTA CAACATCCCA    1498

AATTGGATCC G    1509

( 2 ) INFORMATION FOR SEQ ID NO:33:

( i ) SEQUENCE CHARACTERISTICS:
        ( A ) LENGTH: 476 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

| Ala | Ser | Pro | Gly | Ile | Leu | Arg | Gly | Ala | His | Asn | Leu | Asp | Cys | Val | Leu |
|---|---|---|---|---|---|---|---|---|---|---|---|---|---|---|---|
| 1 |   |   |   | 5 |   |   |   |   | 10 |   |   |   |   | 15 |   |

| Arg | Glu | Gly | Ala | Thr | Leu | Phe | Pro | Val | Val | Ile | Thr | Thr | Val | Glu | Asp |
|---|---|---|---|---|---|---|---|---|---|---|---|---|---|---|---|
|   |   |   | 20 |   |   |   |   | 25 |   |   |   |   | 30 |   |   |

| Ala | Met | Thr | Pro | Lys | Ala | Leu | Asn | Ser | Lys | Met | Phe | Ala | Val | Ile | Glu |
|---|---|---|---|---|---|---|---|---|---|---|---|---|---|---|---|
|   |   | 35 |   |   |   |   | 40 |   |   |   |   | 45 |   |   |   |

| Gly | Val | Arg | Glu | Asp | Leu | Gln | Pro | Pro | Ser | Gln | Arg | Gly | Ser | Phe | Ile |
|---|---|---|---|---|---|---|---|---|---|---|---|---|---|---|---|
|   | 50 |   |   |   |   | 55 |   |   |   |   | 60 |   |   |   |   |

| Arg | Thr | Leu | Ser | Gly | His | Arg | Val | Tyr | Gly | Tyr | Ala | Pro | Asp | Gly | Val |
|---|---|---|---|---|---|---|---|---|---|---|---|---|---|---|---|
| 65 |   |   |   |   | 70 |   |   |   |   | 75 |   |   |   |   | 80 |

| Leu | Pro | Leu | Glu | Thr | Gly | Arg | Asp | Tyr | Thr | Val | Val | Pro | Ile | Asp | Asp |
|---|---|---|---|---|---|---|---|---|---|---|---|---|---|---|---|
|   |   |   |   | 85 |   |   |   |   | 90 |   |   |   |   | 95 |   |

| Val | Trp | Asp | Asp | Ser | Ile | Met | Leu | Ser | Lys | Asp | Pro | Ile | Pro | Pro | Ile |
|---|---|---|---|---|---|---|---|---|---|---|---|---|---|---|---|
|   |   |   | 100 |   |   |   |   | 105 |   |   |   |   | 110 |   |   |

| Val | Gly | Asn | Ser | Gly | Asn | Leu | Ala | Ile | Ala | Tyr | Met | Asp | Val | Phe | Arg |
|---|---|---|---|---|---|---|---|---|---|---|---|---|---|---|---|
|   |   | 115 |   |   |   |   | 120 |   |   |   |   | 125 |   |   |   |

| Pro | Lys | Val | Pro | Ile | His | Val | Ala | Met | Thr | Gly | Ala | Leu | Asn | Ala | Cys |
|---|---|---|---|---|---|---|---|---|---|---|---|---|---|---|---|
|   | 130 |   |   |   |   | 135 |   |   |   |   | 140 |   |   |   |   |

| Gly | Glu | Ile | Glu | Lys | Ile | Ser | Phe | Arg | Ser | Thr | Lys | Leu | Ala | Thr | Ala |
|---|---|---|---|---|---|---|---|---|---|---|---|---|---|---|---|
| 145 |   |   |   |   | 150 |   |   |   |   | 155 |   |   |   |   | 160 |

| | | | | | | | | | | | | | | |
|---|---|---|---|---|---|---|---|---|---|---|---|---|---|---|
| His | Arg | Leu | Gly | Leu | Lys | Leu | Ala | Gly | Pro | Gly | Ala | Phe | Asp | Val | Asn |
| | | | | 165 | | | | | 170 | | | | | 175 | |
| Thr | Gly | Pro | Asn | Trp | Ala | Thr | Phe | Ile | Lys | Arg | Phe | Pro | His | Asn | Pro |
| | | | 180 | | | | | 185 | | | | | 190 | | |
| Arg | Asp | Trp | Asp | Arg | Leu | Pro | Tyr | Leu | Asn | Leu | Pro | Tyr | Leu | Pro | Pro |
| | | | 195 | | | | | 200 | | | | | 205 | | |
| Asn | Ala | Gly | Arg | Gln | Tyr | His | Leu | Ala | Met | Ala | Ala | Ser | Glu | Phe | Lys |
| | | | 210 | | | | 215 | | | | | 220 | | | |
| Glu | Thr | Pro | Glu | Leu | Glu | Ser | Ala | Val | Arg | Ala | Met | Glu | Ala | Ala | Ala |
| 225 | | | | | 230 | | | | | 235 | | | | | 240 |
| Ser | Val | Asp | Pro | Leu | Phe | Gln | Ser | Ala | Leu | Ser | Val | Phe | Met | Trp | Leu |
| | | | | 245 | | | | | 250 | | | | | 255 | |
| Glu | Glu | Asn | Gly | Ile | Val | Thr | Asp | Met | Ala | Asn | Phe | Ala | Leu | Ser | Asp |
| | | | 260 | | | | | 265 | | | | | 270 | | |
| Pro | Asn | Ala | His | Arg | Met | Arg | Asn | Phe | Leu | Ala | Asn | Ala | Pro | Gln | Ala |
| | | | 275 | | | | 280 | | | | | 285 | | | |
| Gly | Ser | Lys | Ser | Gln | Arg | Ala | Lys | Tyr | Gly | Thr | Ala | Gly | Tyr | Gly | Val |
| | | | 290 | | | | 295 | | | | | 300 | | | |
| Glu | Ala | Arg | Gly | Pro | Thr | Pro | Glu | Glu | Ala | Gln | Arg | Glu | Lys | Asp | Thr |
| 305 | | | | | 310 | | | | | 315 | | | | | 320 |
| Arg | Ile | Ser | Lys | Lys | Met | Glu | Thr | Met | Gly | Ile | Tyr | Phe | Ala | Thr | Pro |
| | | | | 325 | | | | | 330 | | | | | 335 | |
| Glu | Trp | Val | Ala | Leu | Asn | Gly | His | Arg | Gly | Pro | Ser | Pro | Gly | Gln | Leu |
| | | | | 340 | | | | 345 | | | | | 350 | | |
| Lys | Tyr | Trp | Gln | Asn | Thr | Arg | Glu | Ile | Pro | Asp | Pro | Asn | Glu | Asp | Tyr |
| | | | 355 | | | | | 360 | | | | | 365 | | |
| Leu | Asp | Tyr | Val | His | Ala | Glu | Lys | Ser | Arg | Leu | Ala | Ser | Glu | Glu | Gln |
| | | 370 | | | | | 375 | | | | | 380 | | | |
| Ile | Leu | Arg | Ala | Ala | Thr | Ser | Ile | Tyr | Gly | Ala | Pro | Gly | Gln | Ala | Glu |
| 385 | | | | | 390 | | | | | 395 | | | | | 400 |
| Pro | Pro | Gln | Ala | Phe | Ile | Asp | Glu | Val | Ala | Lys | Val | Tyr | Glu | Ile | Asn |
| | | | | 405 | | | | | 410 | | | | | 415 | |
| His | Gly | Arg | Gly | Pro | Asn | Gln | Glu | Gln | Met | Lys | Asp | Leu | Leu | Leu | Thr |
| | | | 420 | | | | | 425 | | | | | 430 | | |
| Ala | Met | Glu | Met | Lys | His | Arg | Asn | Pro | Arg | Arg | Ala | Pro | Pro | Lys | Pro |
| | | 435 | | | | | 440 | | | | | 445 | | | |
| Lys | Pro | Arg | Pro | Asn | Ala | Pro | Thr | Gln | Arg | Pro | Pro | Gly | Arg | Leu | Gly |
| | 450 | | | | | 455 | | | | | 460 | | | | |
| Arg | Trp | Ile | Arg | Thr | Val | Ser | Asp | Glu | Asp | Leu | Glu | | | | |
| 465 | | | | | 470 | | | | | 475 | | | | | |

( 2 ) INFORMATION FOR SEQ ID NO:34:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Infectious bursal disease virus
        ( B ) STRAIN: GLS ( i x ) FEATURE:
        ( A ) NAME/KEY: region
        ( B ) LOCATION: 1..131
        ( D ) OTHER INFORMATION: /note="positions 200-330 of GLS VP2 protein"

( x i ) SEQUENCE DESCRIPTION: SEQ ID NO:34:

| | | | | | | | | | | | | | | |
|---|---|---|---|---|---|---|---|---|---|---|---|---|---|---|
| Leu | Asp | Pro | Lys | Met | Val | Ala | Thr | Cys | Asp | Ser | Ser | Asp | Arg | Pro | Arg |
| 1 | | | | 5 | | | | | 10 | | | | | 15 | |
| Val | Tyr | Thr | Ile | Thr | Ala | Ala | Asp | Asp | Tyr | Gln | Phe | Ser | Ser | Gln | Tyr |
| | | | 20 | | | | | 25 | | | | | 30 | | |
| Gln | Thr | Gly | Gly | Val | Thr | Ile | Thr | Leu | Phe | Ser | Ala | Asn | Ile | Asp | Ala |
| | | 35 | | | | | 40 | | | | | 45 | | | |
| Ile | Thr | Ser | Leu | Ser | Val | Gly | Gly | Glu | Leu | Val | Phe | Lys | Thr | Ser | Val |
| | 50 | | | | | 55 | | | | | 60 | | | | |
| His | Ser | Leu | Val | Leu | Gly | Ala | Thr | Ile | Tyr | Leu | Ile | Gly | Phe | Asp | Gly |
| 65 | | | | | 70 | | | | | 75 | | | | | 80 |
| Ser | Ala | Val | Ile | Thr | Arg | Ala | Val | Ala | Ala | Asn | Asn | Gly | Leu | Thr | Thr |
| | | | | 85 | | | | | 90 | | | | | 95 | |
| Gly | Thr | Asp | Asn | Leu | Met | Pro | Phe | Asn | Leu | Val | Ile | Pro | Thr | Asn | Glu |
| | | | 100 | | | | | 105 | | | | | 110 | | |
| Ile | Thr | Gln | Pro | Ile | Thr | Ser | Ile | Lys | Leu | Glu | Ile | Val | Thr | Ser | Lys |
| | | 115 | | | | | 120 | | | | | 125 | | | |
| Ser | Gly | Gly | | | | | | | | | | | | | |
| | 130 | | | | | | | | | | | | | | |